US006835820B2

(12) United States Patent
Cannon et al.

(10) Patent No.: US 6,835,820 B2
(45) Date of Patent: Dec. 28, 2004

(54) POLYHYDROXYALKANOATE BIOSYNTHESIS ASSOCIATED PROTEINS AND CODING REGION IN BACILLUS MEGATERIUM

(75) Inventors: Maura Cannon, Amherst, MA (US); Francis C. Cannon, Amherst, MA (US); Gabriel J. McCool, Northhampton, MA (US); Henry E. Valentin, Chesterfield, MO (US); Kenneth J. Gruys, Chesterfield, MO (US)

(73) Assignee: The University of Massachusetts, Amherst, MA (US)

( * ) Notice: Subject to any disclaimer, the term of this patent is extended or adjusted under 35 U.S.C. 154(b) by 211 days.

(21) Appl. No.: 09/479,040

(22) Filed: Jan. 7, 2000

(65) Prior Publication Data

US 2002/0182690 A1 Dec. 5, 2002

Related U.S. Application Data

(60) Provisional application No. 60/115,092, filed on Jan. 7, 1999.

(51) Int. Cl.[7] .................. C07H 21/04; C12Q 1/68; C12N 9/06; C12N 15/00; C12N 15/09

(52) U.S. Cl. ................ 536/23.2; 536/22.1; 536/24.1; 435/6; 435/191; 435/320.1

(58) Field of Search .................. 435/6, 191, 320.1; 536/23.2

(56) References Cited

U.S. PATENT DOCUMENTS

| | | | |
|---|---|---|---|
| 5,229,279 A | 7/1993 | Peoples et al. | 435/135 |
| 5,245,023 A | 9/1993 | Peoples et al. | 536/23.2 |
| 5,250,430 A | 10/1993 | Peoples et al. | 435/232 |
| 5,480,794 A | 1/1996 | Peoples et al. | 435/232 |
| 5,512,669 A | 4/1996 | Peoples et al. | 536/23.2 |
| 5,534,432 A | 7/1996 | Peoples et al. | 435/240.4 |
| 5,661,026 A | 8/1997 | Peoples et al. | 435/252.3 |
| 5,663,063 A | 9/1997 | Peoples et al. | 435/135 |
| 5,942,660 A | 8/1999 | Gruys et al. | 800/298 |

FOREIGN PATENT DOCUMENTS

| | | |
|---|---|---|
| WO | WO 92/19747 | 11/1992 |
| WO | WO 98/04713 | 5/1998 |

OTHER PUBLICATIONS

International Search Report for PCT/US00/00364 dated Jun. 14, 2000.
Li, N. and Cannon, M.C., A Molecular Genetic Analysis of Polyhydroxyalkanoate (PHA) Accumulation in *Bacillus megaterium*, 95th General Meeting of the American Society for Microbiology, 95: 547 (1995).
McCool, G. and Cannon, M.C., Identification and Characterization of the *phaBC* Locus from *Bacillus megaterium*, 97th General Meeting of the American Society for Microbiology, 97:288 (1997).
McCool, G. and Cannon, M.C., *Bacillus megaterium* polyhydroxyalkanoate gene cluster, complete sequence, *EMBL Sequence Database*, XP002138871 (1999).
McCool, G. and Cannon, M.C., Polyhydroxyalkanoate Inclusion Body–Associated Proteins and Coding Region in *Bacillus megaterium, Journal of Biotechnology*, 181: 585–592 (1999).
Pettinari, M.J., et al., *trans* activation of the *Escherichia coli ato* structural genes by a regulatory protein from *Bacillus megaterium*: potential use in polyhydroxyalkanoate production, *Appl. Microbiol. Biotechnol.*, 49: 737–742 (1998).
Poirier, Y., et al., Production of Polyhydroxyalkanotes, a Family of Biodegradable Plastics and Elastomers, in Bacteria and Plants, *Bio/Technology*, 13: 142–150 (1995).
Poirier, Y., et al., Progress Toward Biologically Produced Biodegradable Thermoplastics, *Adv. Mater.*, 5: 30–36 (1995).
Valentin, H.E., et al., Metabolic pathway for biosynthesis of poly(3–hydroxybutyrate–co–4–hydroxybutyrate) from 4–hydroxybutyrate by *Alcaligenes eutrophus*, *Eur. J. Biochem.*, 227:43–60 (1995).
DeSmet, M.J., G. Eggink, B. Witholt, J. Kingma, and H. Wynberg. 1983. Characterization of intracellular inclusions formed by *Pseudomonas oleovorans* during growth on octane. *J. Bacteriol.*, 154: 870–878.
Dunlop, W. and A.W. Robards. 1973. Ultrastructural study of poly–β–hydroxybutyrate granules from *Bacillus cereus*. *J. Bacteriol.*, 114: 1271–1280.
Eggink, G., P. de Waard, and G.N.M. Huijberts. 1992. The role of fatty acid biosynthesis and degradation in the supply of substrates for poly(3–hydroxyalkanoate) formation in *Pseudomonas putida*. *FEMS Microbiol. Rev.*, 103: 159–164.
Ellar, D., D.G. Lundgren, K. Okamura, and R.H. Marchessault. 1968. Morphology of poly–β–hydroxbutyrate granules. *J. Mol. Biol.*, 35: 489–502.
Fuller, R.C., J.P. O'Donnell, J Saulnier, T.E. Redlinger, J. Foster, and R.W. Lenz. 1992. The supramolecular architecture of the polyhydroxyalkanoate inclusions in *Pseudomonas oleovorans*. *FEMS Microbiol. Rev.*, 103: 279–288.
Gerngross, T.U., P. Reilly, J. Stubbe, A.J. Sinskey, and O.P. Peoples. 1993. Immunocytochemical analysis of poly–β–hydroxybutyrate (PHB) synthase enzyme at the surface of PHB granules. *J. Bacteriol.*, 175: 5289–5293.

(List continued on next page.)

Primary Examiner—Ethan Whisenant
Assistant Examiner—Arun Kr. Chakrabarti
(74) Attorney, Agent, or Firm—Holland & Knight LLP

(57) ABSTRACT

A 7,916 base pair nucleic acid fragment from *Bacillus megaterium* is disclosed. The fragment encodes five proteins, PhaP, PhaQ, PhaR, PhaB, 09 and PhaC, shown or inferred to be involved in the biosynthesis of polyhydroxyalkanoate materials.

12 Claims, 12 Drawing Sheets

OTHER PUBLICATIONS

Griebel, R., Z. Smith, and M. Merrick. 1968. Metabolism of poly–β–hydroxybutyrate. 1. Purification, composition, and properties of native poly–β–hydroxyburyrate granules from *Bacillus megaterium. Biochem.*, 7: 3676–3681.

Haywood, G.W., A.J. Anderson, L. Chu, and E.A. Dawes. 1988. Characterization of two 3–ketothiolases in the polyhydroxyalkanoate synthesizing organism *Alcaligenes eutrophus. FEMS Microbiol. Lett.*, 52: 91–96.

Huang, A.H.C. 1992. Oil bodies and oleosins in seeds. *Annu. Rev. Plant Physiol. Plant Mol. Biol.*, 43: 177–200.

Lauzier, C., R.H. Marchessault, P. smith, and H. Chanzy. 1992. Structural study of isolated poly(β–hydroxybutyrate) granules. *Polymer*, 33: 823–827.

Lee, S.Y. 1995. Bacterial polyhydroxyalkanoates. *Biotechnology & Engineering*, 49: 1–14.

Lundgren, D.G., R.M. Pfister, and J.M. Merrick. 1964. Structure of poly–β–hydroxybutyric acid granules, *J. Gen. Microbiol.*, 34: 441–446.

McCool, G.J., T. Fernandez, N. Li, and M.C. Cannon. 1996. Polyhydroxyalkanoate inclusion–body growth and proliferation in *Bacillus megaterium. FEMS Microbiol. Lett.*, 137: 41–48.

Pieper–Furst, U., M.H. Madkour, F. Mayer, and A. Steinbüchel. 1994, Purification and characterization of a 14–kilodalton protein that is bound to the surface of polyhydroxyalkanoic acid granules in *Rhodococcus ruber. J. Bacteriol.*, 176: 4328–4337.

Pieper–Furst, U., M.H. Madkour, F. Mayer, and A. Steinbüchel. 1995, Identification of the region of a 14–kilodalton protein of *Rhodococcus ruber* that is responsible for the binding of this Phasin to polyhydroxyalkanoic acid granules. *J. Bacteriol.*, 177: 2513–2523.

Steinbüchel, A., K. Aerts, W. Babel, C. Follner, M. Liebergesell, M.H. Madkour, F. Mayer, U. Pieper–Furst, A. Pries, H.E. Valentin, and R. Wieczorek. 1995. Considerations on the structure and biochemistry of bacterial polyhydroxyalkanoic acid inclusions. *Can. J. Microbiol.*, 41: 94–105.

Steinbüchel, A., E. Hustede, M. Liebergesell, U. Pieper, A. Timm, and H. Valentin. 1992. Molecular basis for biosynthesis and accumulation of polyhydroxyalkanoic acids in bacteria. *FEMS Microbiol. Rev.*, 103: 217–230.

Steinbüchel, A. and H.G. Schlegel. 1991. Physiology and molecular genetics of poly(β–hydroxyalkanoic acid) synthesis in *Alcaligenes eutrophus. Mol. Microbiol.*, 5: 535–542.

Steinbüchel, A. and H.E. Valentin. 1995. Diversity of bacterial polyhydroxyalkanoic acids. *FEMS Microbiol. Lett.*, 128: 219–228.

Wang, W.S. and D.G. Lundgren. 1969. Poly–β–hydroxybutyrate in the chemolithotrophic bacterium *Ferrobacillus ferrooxidans. J. Bacteriol.*, 97: 947–950.

Wieczorek, R., A. Pries, A. Steinbüchel, and F. Mayer. 1995. Analysis of a 24–kilodalton protein associated with the polyhydroxyalkanoic acid granules in *Alcaligenes eutrophus. J. Bacteriol.*, 177: 2425–2435.

Wieczorek, R., A. Steinbüchel, and B. Schmidt. 1996. Occurrence of polyhydroxyalkanoic acid granule–associated proteins related to the *Alcaligenes eutrophus* H16 GA24 protein in other bacteria. *FEMS Microbiol. Lett.*, 135: 23–30.

```
                              -35                      -10      +1              Met
        TTCAAAAATAAACAAAGATTTAGAATTGTTTATTTTGGAAAACGTATTTATAATAGTACATGL...275nt...ATG    PhoR
(SigmaA)                        ttgaca                     tataat
        TGTATTTGAAAGACCTGTTTTAAAGTGTTGACAATTTTTTCATCTAGGTGTAAATTACACATA....39nt...TTG    PhoO
(SigmaA)                        ttgaca                    tataat
        TTTTAGCTCTTCTTCTTCTAAAAAGTCAAAAGAATCAAAAGAGGAAGAAAACGATTAAAGGGA...164nt...ATG   PhoP
(SigmaD)                   ctaaa                          ccgatat
TAATATATAAAAAAGCCCAGCTTCTTGAAAGCTGGCTTTTTTATACTTTCTTGCAAACATTACCA....79nt...ATG    SspD
PhoP
STOP
```

FIGURE 2B

B.meg. AIFYVQ WEK——————— IK —————————MFS ————— YESS ———— FKRA— 31
P.ole. SNKNKI LQRQASENTLGLNPVKGIRRKD LS ARTVLRQAVRQFLHSAKHVAHPGLELKNVLLGKSSLAH SDDRRFNDP WSNNPL YLQT LAW 100

B.meg. ————————EI ———— TEAR EVC T——————————P ———————— B———————————————— IWKKNK 55
P.ole. RKELQDWIGNSDLSPQDISRGQFVINL EAMA TNT SNPAAVKRFFETGGKSLLDGLSNLA DLVNNGGMPSQVNMDAFEVGKNLGTSEG VYRNDV 200

B.meg. AK R VKDN K L VAL P L IC N VE L NRGFDVYLL T GLEDSNM DE YIPK AKE RTSK SV M 155
P.ole. LE Q D TEQV A L V PQ F VF S EK AP I RSQQQIFUS N TKAQREW ST L ALK VDA AITG N A S 299

B.meg. —TMTSIF A N DLPKN IFMT PF FSDTGLYGA L DRYFNLD AVDTFGNIP MIDFGNKM-LK TTNFYGPY LVDRSENQRFVESWK 249
P.ole. ITCTALVGHY K N-KVNA TLLVI VL TTMDNQVA M EQTLEAA R-HSYQAGVL GSEMAKVFAWM NDLJWNY NNYLLGNEPPVFDI- 395

B.meg. MQ VA GPFAGE YRQWIRDFYQ K DNGE- I N RK DI NI AN LNI ASR I AM H VAALMDAYSSED Y LQT VSVVFG KA-V 347
P.ole. F- N TTRLPA- PHGDLIEMFKS F TRPDA N C TPI D QV CD VSL GTN T- W SCYRSAHLFGGKI V SNS QSILN PGNP 491

B.meg. ETYPSIG I—————————— DP S——————————K 362
P.ole. ARFMTG RPGDPVAWQENATICHADSWWLHW GE AGELEKAPTRLGNRAYAAGEASPCTYVHER 559

FIGURE 3

```
PhaC_Bm    MAIPYVQEWEKLIKSMPSEYKSSARRFKRAYEIMTTEAEPEVGLTPKEVIWKKNKAKLYR
PhaC_Tv    -----MRPIDIRPDKLAQEMLDYTSKLGQGMENLLNADAIDTGVSPKEAVYSEDKLVLYR
           ..   .    *   .. *  .   .*.,*** .    *  ***

PhaC_Bm    Y-TPVKDNLHKTPILLVYALINKPYILDLTPGNSLVEYLLNRGPDVYLLDWGTPGLEDSN
PhaC_Tv    YDTPAGVTPQKTPLLIVYALVNRPYMTDIQEDRSTIKGLLATGQDVYLIDWGYPDQADSA
           * **   . ***.*.****.*.**. *.    *  ** * ****.*** *  **

PhaC_Bm    MKLDDYIVDYIPKAAKKVLRTSKSPDLSVLGYCMGGTMTSIPAALNEDLPIKNLIFMTSP
PhaC_Tv    LTLDDYINGYIDSCVDYLCETHEVDQVNILGICQGGAFSLMYASLHPDK-VKNLVTMVTP
           . ***** **  .    *   .** * **. . ..*.*. *  ***. * .*

PhaC_Bm    FDFSDTG-LYGAFLDDRYFNLDKAVDTFGNIPPEMIDPGNKMLKPITNFYGPYVTLVDRS
PhaC_Tv    VDFKTPGNLLSAWVQN--VDIDLAVDTMGNIPGELLNWTFLSLKPFSLTGQKYVNMVDML
           ** *  * .    . *. .* **** **** *..  ***  .  **..**

PhaC_Bm    ENQRFVESWKLMQKWVADGIPPAGEAYRQWIRDFYQQNKLINGELEVRGRKVDLKNIKAN
PhaC_Tv    DDPDKVKNFLRMEKWIFDSPDQAGETFRQFTKDFYQKNGFINGGVKLGGKEIDLKNVDCP.
           .   *  *.** * *  **. *  ****.* ***   .*. .****. .

PhaC_Bm    ILNIAASRDHIAMPHQVAALMDAVSSEDKEYKLLQTGHVSVVPGPKAVKETYPSIGDWLE
PhaC_Tv    VLNIYALQDHLVPPDASKALNPWSAARTYTELAFPGGHIGIYVSGKAQKEVTPAIGKWLN
           .*** * .**. *   **       **. .   ** ** *  *.** **

PhaC_Bm    KRSK
PhaC_Tv    ERS-
           **
```

FIGURE 9

POLYHYDROXYALKANOATE BIOSYNTHESIS ASSOCIATED PROTEINS AND CODING REGION IN *BACILLUS MEGATERIUM*

This patent application is related to U.S. Provisional Application Serial No. 60/115,092, filed on Jan. 7, 1999. The government may own partial rights to the present invention pursuant to grant number MCB 9604450 from the National Science Foundation.

FIELD OF THE INVENTION

The invention relates to nucleic acid and amino acid sequences involved in polyhydroxyalkanoate biosynthesis, and more specifically, to polyhydroxyalkanoate biosynthesis sequences isolated from *Bacillus megaterium*. In particular, nucleic acid sequences phaP, phaQ, phaR, phaB, phaC, and their encoded amino acid sequences are disclosed.

BACKGROUND OF THE INVENTION

Polyhydroxyalkanoic acids (PHA) are a class of aliphatic polyesters that accumulate in inclusion-bodies in many bacteria and archaea (2, 41). Their physiological role in the cell is that of carbon and energy reserves, and as a sink for reducing power. The most studied PHA have repeating subunits of: —[O—CH(R)(CH$_2$)$_x$CO]—, where the most common form is polyhydroxybutyrate (PHB), with R=CH$_3$ and x=1 (45). The PHA biosynthetic pathway has been determined for *Alcaligenes eutrophus* (17, 18, 44). In this organism two molecules of acetyl-Coenzyme A (CoA) are condensed by β-ketothiolase (PhaA), followed by a stereospecific reduction catalyzed by an NADPH dependent acetoacetyl-CoA reductase (PhaB) to produce the monomer D-(-)-β-hydroxybutyryl-CoA, which is polymerized by PHA synthase (PhaC). These 3 pha genes are coded on the phaCAB operon, which is speculated to be constitutively expressed, but PHA is not constitutively synthesized. Alternative pathways for synthesis of the monomer in other organisms have been suggested, most notably in the Pseudomonas species where the side chain, R, is longer than CH$_3$ and its composition is influenced by carbon substrates in the growth medium (7, 45). In addition to *A. eutrophus*, phaC has been cloned from more than twenty different bacteria (26, 43). Other genes associated with PHA synthesis, phaA, phaB, phaZ (PHA depolymerase) and genes for inclusion-body associated proteins and other low molecular weight proteins of unknown function, have also been cloned from some of these bacteria, in many cases by virtue of the fact that they are clustered with phaC.

PHA inclusion-bodies are 0.2 to 0.5μm in diameter, but their structural details are largely unknown. They were described originally for some species of Bacillus (6, 8, 15, 30, 47) and later for many more bacteria including Pseudomonas, Alcaligenes and Rhodococcus (5, 11, 12, 25, 42). Those from *Bacillus megaterium* were shown to contain 97.7% PHA, 1.87% protein and 0.46% lipid with protein and lipid forming an outer layer (15). More recent reports show the presence of a 14 kDa protein (GA14) on PHA inclusion-bodies of *R. ruber* (36, 37), and a 24 kDa protein (GA24) with similarities to GA14 on the inclusion-bodies of *A. eutrophus* (48). These proteins are not essential for PHA accumulation but have been shown to influence the size of PHA inclusion-bodies and the rate of PHA accumulation (37, 48). GA14 and GA24 have been named "phasins" due to some similarities with oleosins, which are proteins on the surface of oil bodies in plant seeds (21). Granule associated proteins are wide-spread in PHA accumulating bacteria (49). The pattern of PHA inclusion-body growth and proliferation throughout the growth cycle of *Bacillus megaterium* has been described (32).

There exists a need for additional nucleic acid and amino acid sequences useful for the production of polymers in biological systems.

SUMMARY OF THE INVENTION

This invention is the result of a study of PHA inclusion-body associated proteins from *Bacillus megaterium* and the cloning and analysis of their coding region. The transcription starts were identified, the functional expression of several of the sequences was confirmed in *Escherichia coli* and in PHA negative mutants of *Bacillus megaterium* and *Pseudomonas putida*, and PhaP and PhaC were localized to PHA inclusion-bodies throughout growth.

A nucleic acid fragment encoding proteins involved in polyhydroxyalkanoate biosynthesis was isolated from *Bacillus megaterium*. Nine nucleic acid sequences and their encoded amino acid sequences are disclosed. Sequences encoding PhaB and PhaC display not insignificant percent identity and similarity to known acetoacetyl-CoA reductase and polyhydroxyalkanoate synthase proteins, while sequences encoding PhaP, PhaQ, and PhaR do not display significant similarity to known sequences. YkoY is similar to known toxic anion resistance proteins; YkoZ is similar to known RNA polymerase sigma factors; YkrM is similar to known Na$^+$-transporting ATP synthase proteins; and SspD matches the known *B. megaterium* spore specific DNA binding protein.

While several PHA related sequences were expressed in two organisms, it is envisioned that the sequences may be expressed in a wide array of organisms, and that the nucleic acid sequences themselves may be modified to change the sequence and properties of the encoded proteins.

DESCRIPTION OF THE FIGURES

The following figures form part of the present specification and are included to further demonstrate certain aspects of the present invention. The invention may be better understood by reference to one or more of these drawings in combination with the detailed description of specific embodiments presented herein.

*subtilis* genome; genes with homology to those of *Bacillus megaterium* in this region are indicted by thick black arrows; non-homologous genes are indicated by thick gray arrows. Gene annotations are horizontal over each gene symbol. Relevant restriction enzyme sites are vertical.

Figure 2A:
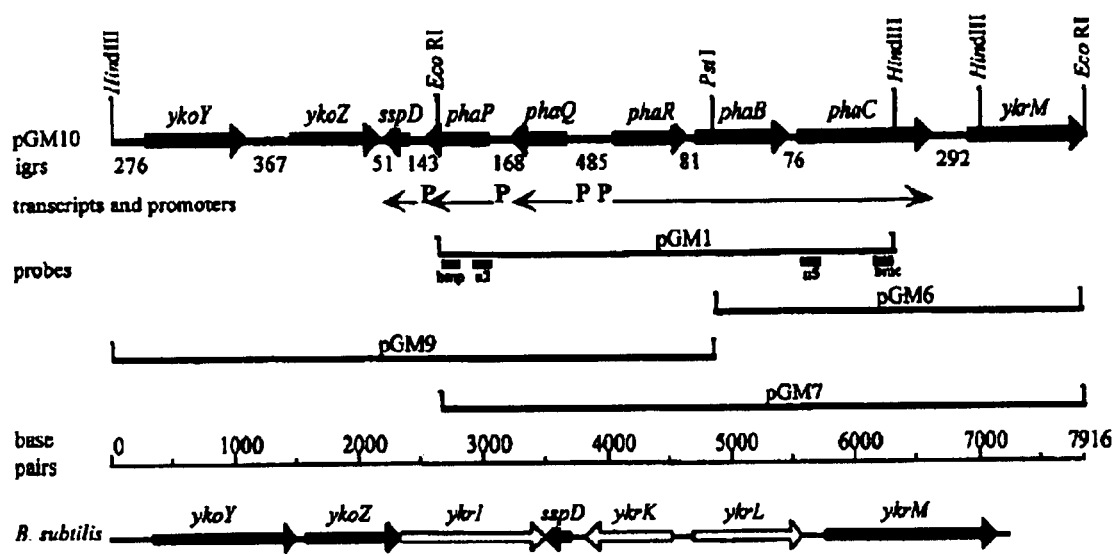
FIG. 2(A): The pha sequence cluster and flanking sequences. Map of cloned fragment in pGM 10 carrying the pha genes (stripped arrows), intergenic regions (igrs) and flanking genes (thick black arrows) from *Bacillus megaterium*. The thin arrows indicate the locations and directions of transcripts; P, indicates promoter positions. pGM1, pGM6, pGM9 and pGM7 indicate the cloned DNA fragments in these plasmids (Table 1). Probes used to identify and clone the pha cluster are indicated by thick short lines under pGM1; n2 and n5 are degenerate probes; bmp and bmc are homologous probes to the ends of the pGM 1 fragment. Ruler of sequence in base pairs is for *Bacillus megaterium* and *B. subtilis*. Map of yko, sspD and ykr region in the *B.*

FIG. 2(B): Putative promoter regions for phaRBC, -Q, -P and sspD. Curved arrows indicate transcription start (+1), −10 and −35 nucleotides. The closest resemblance to known −10 and −35 promoter sequences are in lower case letters below putative pha promoter sequences. Immediately downstream from the PhaP stop codon, the previously described (9) sspD putative promoter is boxed, and putative hairpin structure is underlined.

Figure 2C:
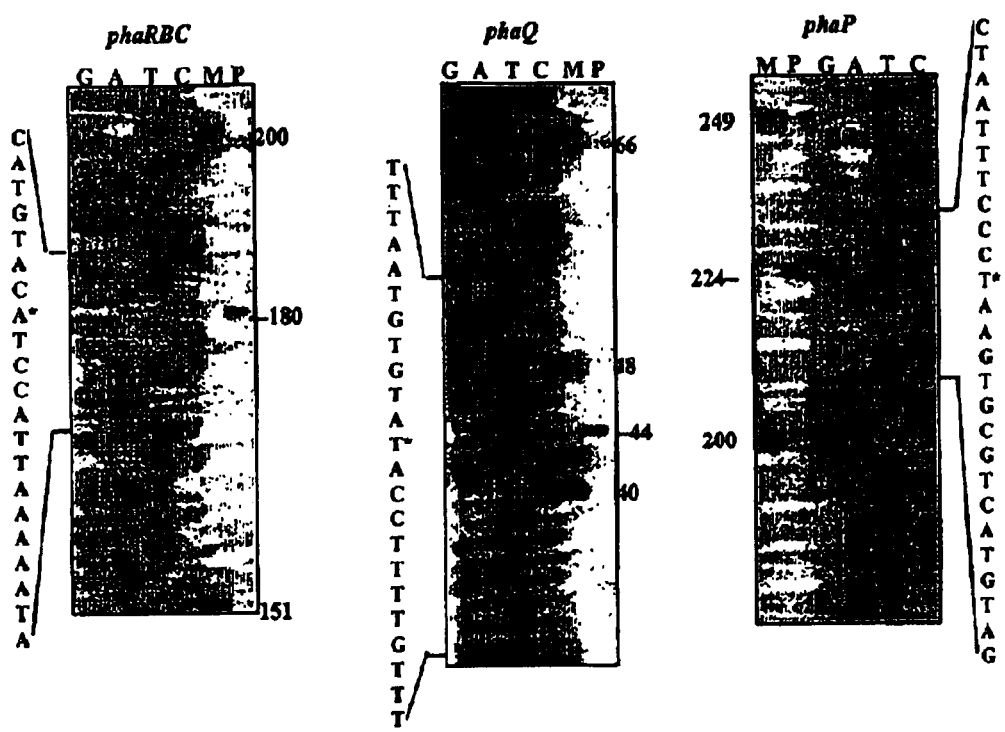

FIG. 2(C): Mapping of the 5' ends of the phaRBC, -Q and -P transcripts (see Example 11). Lanes G, A, T and C show the dideoxy sequencing ladders obtained with the same primers used in primer extension analysis; nucleotide sequences are complementary to the transcripts. Lane P is the primer extension product. Lane M is a DNA molecular size marker measured in nucleotides. The primer extension product is indicated by an arrowhead and the 5' end of the transcript within the sequence is indicated by a star. Only regions of the gel containing extension product bands are shown.

FIG. 3: Pairwise alignment of PhaC from *Bacillus megaterium* (this study) and *P. oleovorans* (SWISS-PROT accession no. P26494); amino acid identities are shown in black. The Clustal method with PAM250 residue weight table was used.

Figure 4:
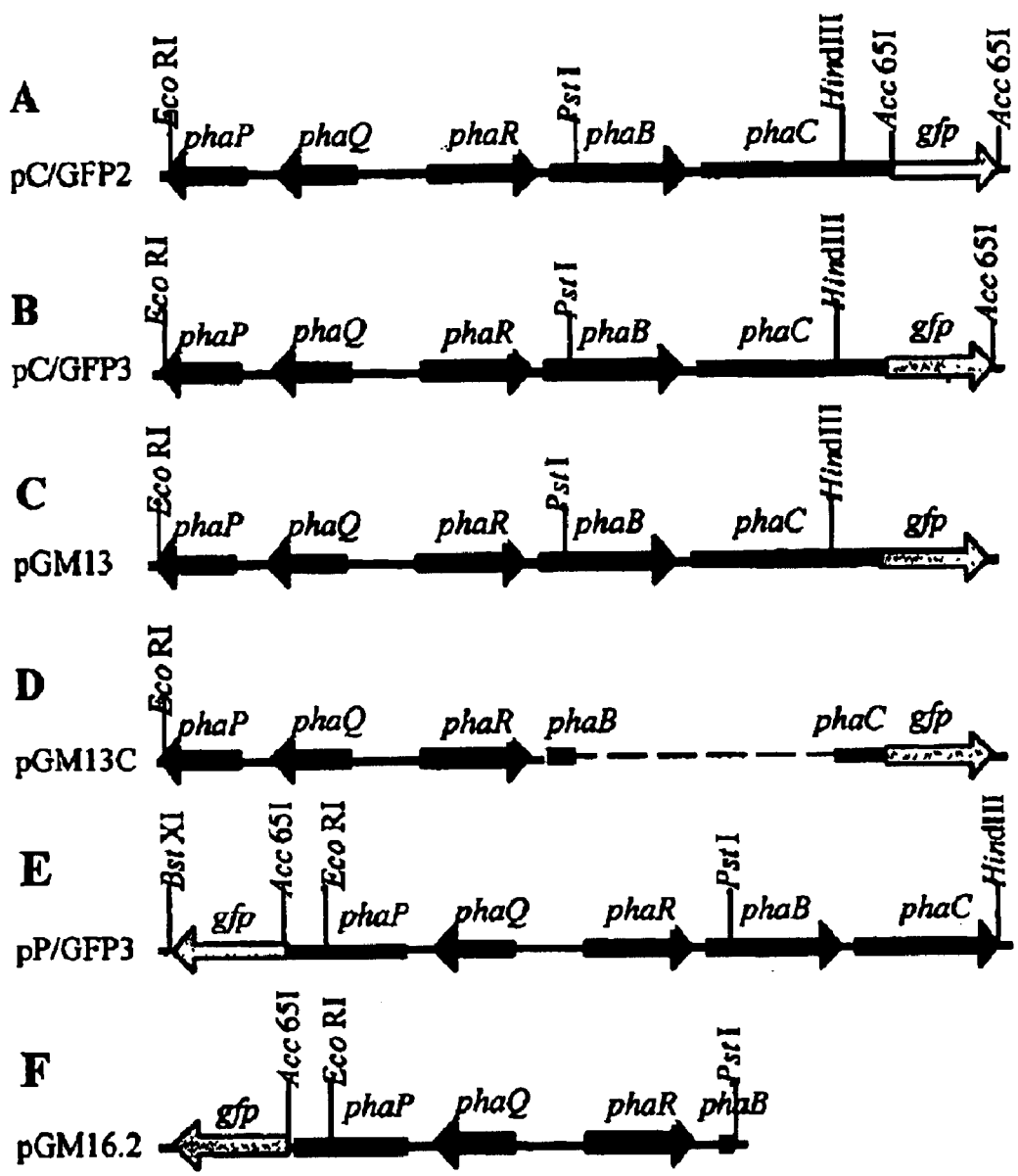

FIG. 4. pha::gfp fusion plasmids and precursors. Only relevant restriction sites are shown. Annotations are as FIG. 2. In all fusions the c-terminus excluding the stop codon, of either phaC or phaP, is fused to the gfp gene by the pGFPuv polylinker. For more details, see Table 1.

Figure 5:
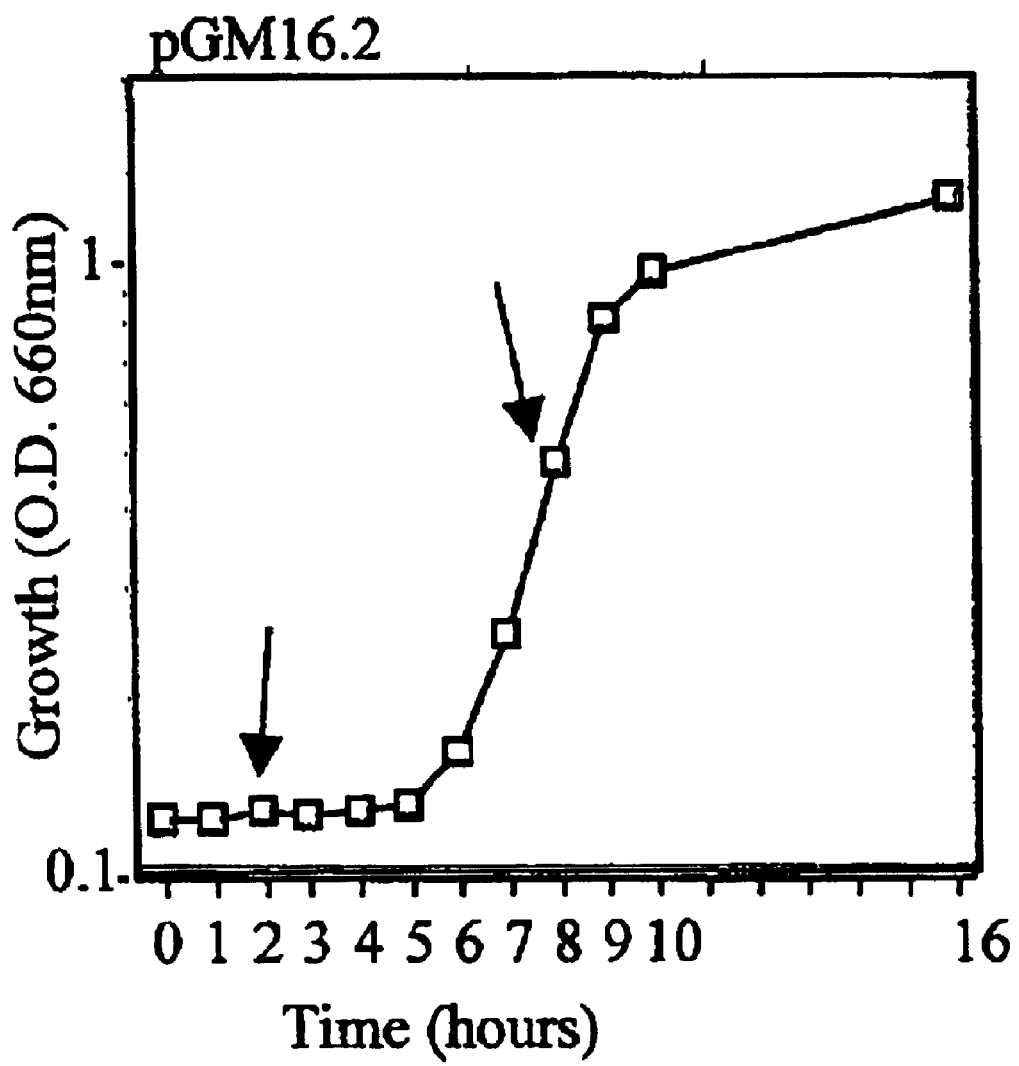

FIG. 5: Growth curve for time-course analysis of *Bacillus megaterium* (pGM16.2); arrowheads indicate a decrease in PhaP::GFP fluorescence.

Figure 6:
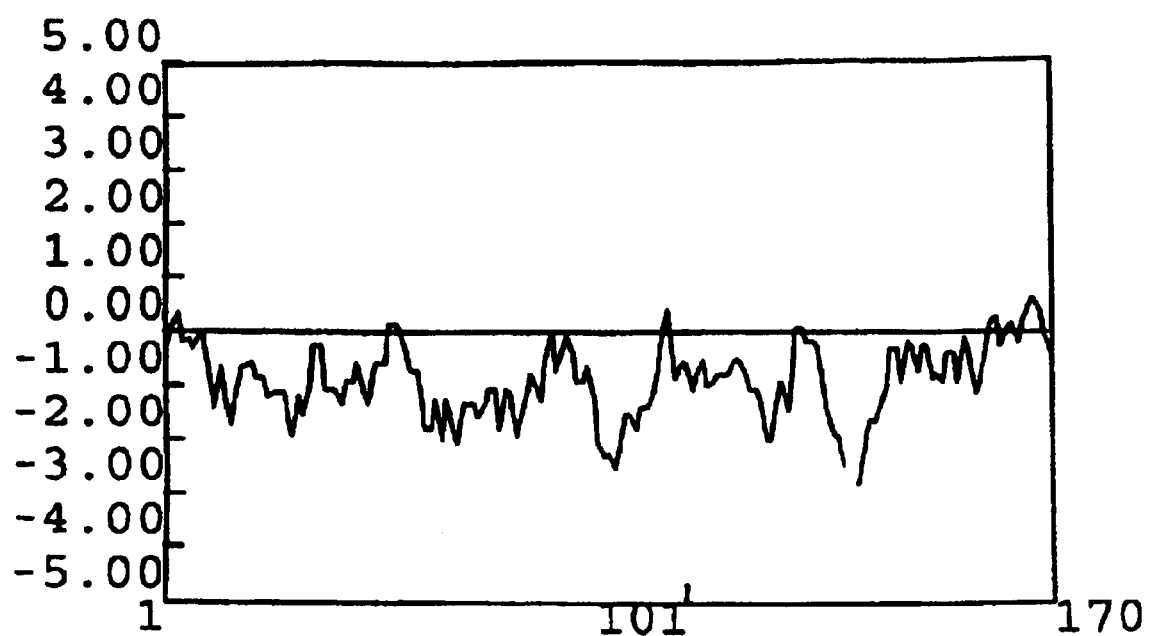

FIG. 6: Hydrophilicity plot of PhaP protein.

Figure 7:
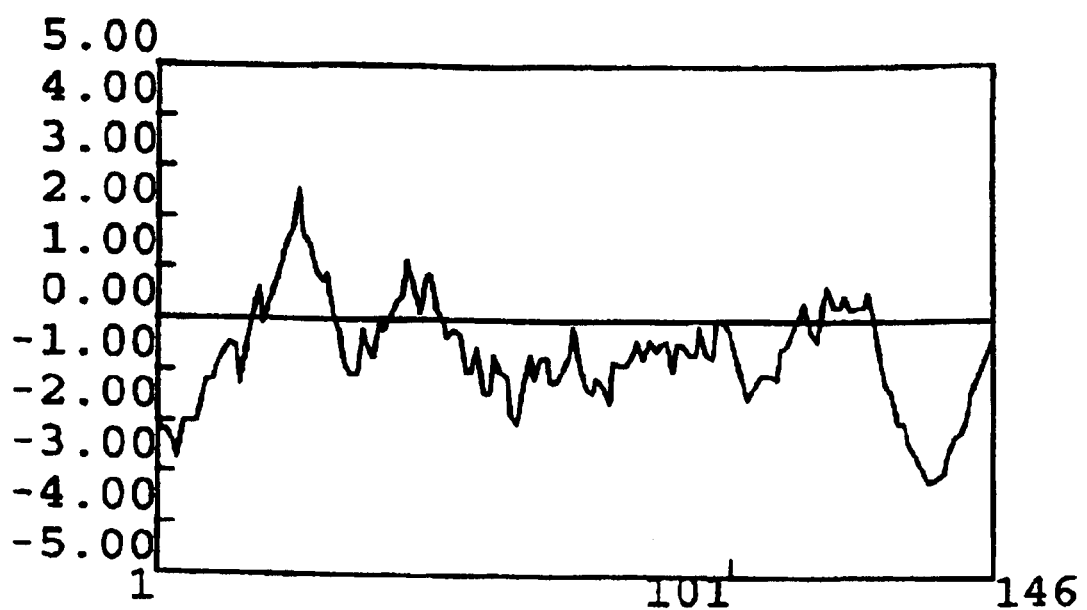

FIG. 7: Hydrophilicity plot of PhaQ protein.

Figure 8:
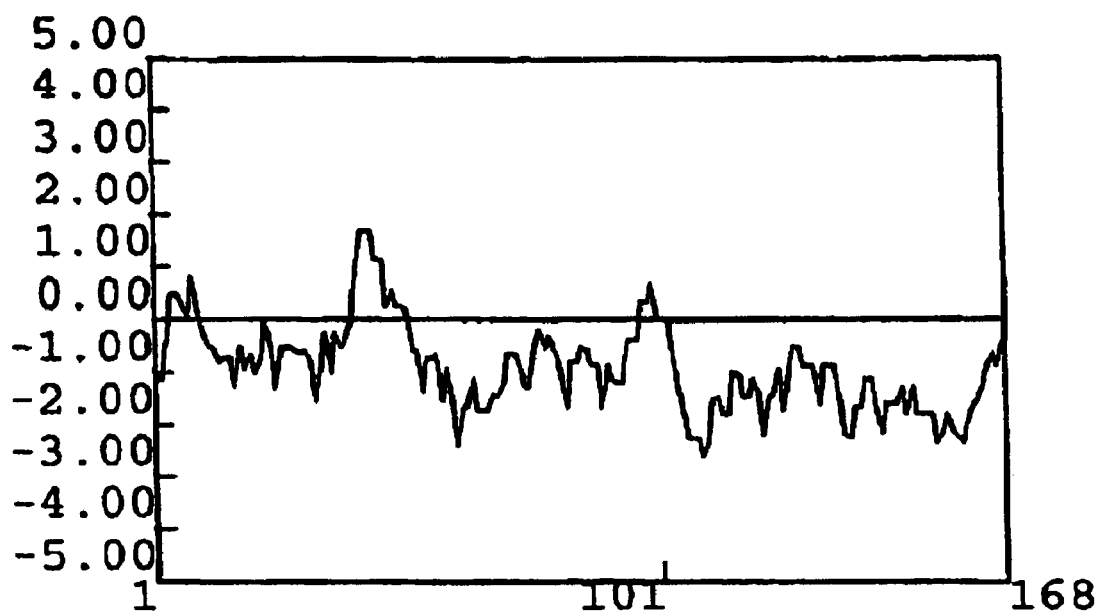

FIG. 8: Hydrophilicity plot of PhaR protein.

FIG. 9: Pairwise alignment of PhaC from *Bacillus megaterium* (this study) and *T violacea* (SWISS-PROT accession no. P45366); amino acid identities are indicated by a star (*), and amino acid similarities are indicated by a period (.) below the sequences. The ClustalW method with PAM350 residue weight table was used.

Figure 10:
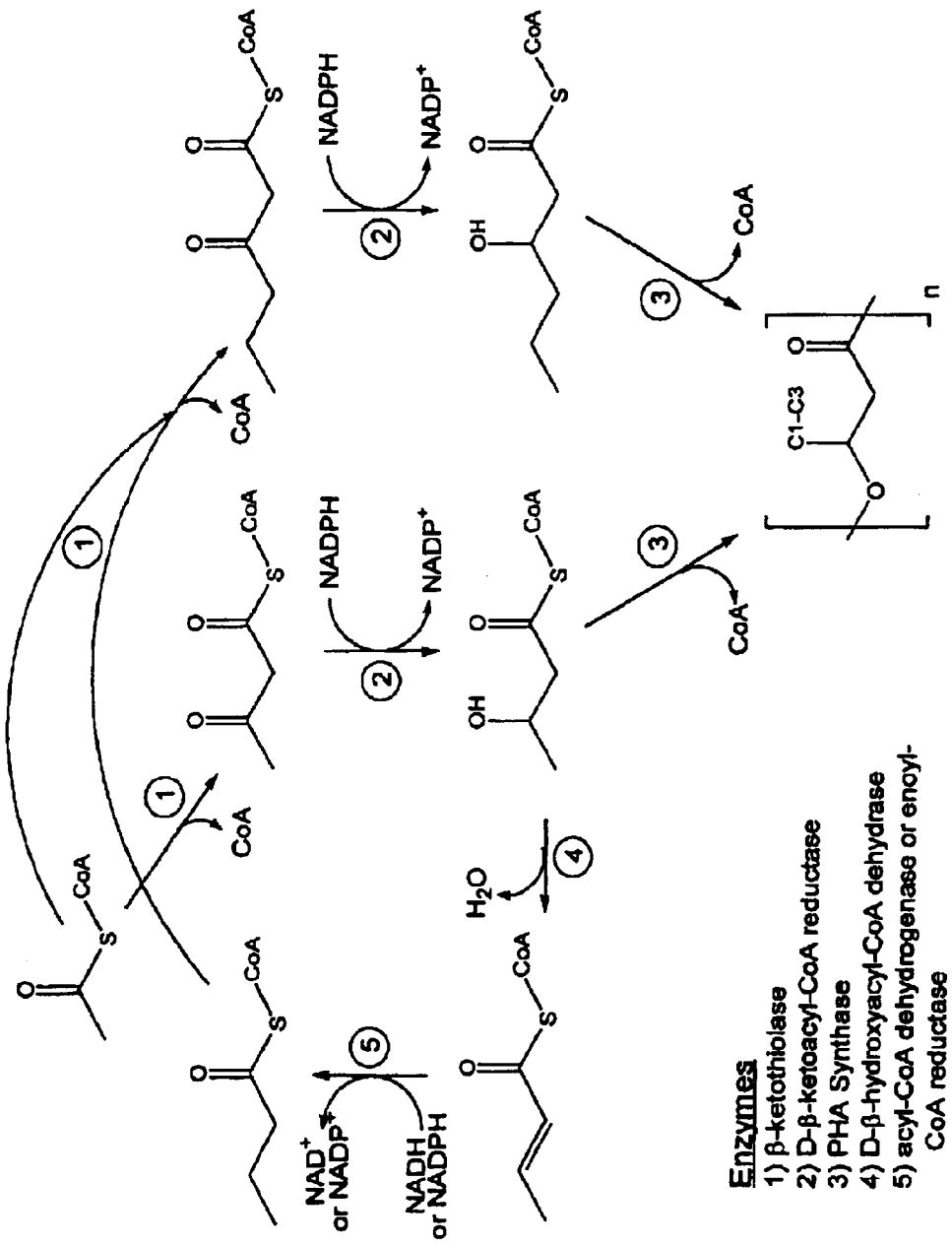

FIG. 10: Proposed biosynthetic pathway for the preparation of C8 copolymers.

DESCRIPTION OF THE SEQUENCE LISTINGS

The following sequence listings form part of the present specification and are included to further demonstrate certain aspects of the present invention. The invention may be better understood by reference to one or more of these sequences in combination with the detailed description of specific embodiments presented herein.

| SEQ ID NO | Description |
| --- | --- |
| 1 | *Bacillus megaterium* 7,916 bp fragment |
| 2 | phaP nucleic acid sequence, 2566–3075 reverse complement |
| 3 | PhaP amino acid sequence, 170 amino acids |

-continued

| SEQ ID NO | Description |
| --- | --- |
| 4 | phaQ nucleic acid sequence, 3247–3684 reverse complement |
| 5 | PhaQ amino acid sequence, 146 amino acids |
| 6 | phaR nucleic acid sequence, 4170–4673 |
| 7 | PhaR amino acid sequence, 168 amino acids |
| 8 | phaB nucleic acid sequence, 4758–5498 |
| 9 | PhaB amino acid sequence, 247 amino acids |
| 10 | phaC nucleic acid sequence, 5578–6663 |
| 11 | PhaC amino acid sequence, 362 amino acids |
| 12 | oligonucleotide probe n2, 39 bases |
| 13 | oligonucleotide probe n5, 30 bases |
| 14 | oligonucleotide probe bmp, 19 bases |
| 15 | oligonucleotide probe bmc, 22 bases |
| 16 | oligonucleotide primer for phaP transcription start, 20 bases |
| 17 | oligonucleotide primer for phaQ transcription start, 19 bases |
| 18 | oligonucleotide primer for phaRBC transcription start, 19 bases |
| 19 | N-terminal amino acid sequence of 14 kDa protein |
| 20 | N-terminal amino acid sequence of 20 kDa protein |
| 21 | N-terminal amino acid sequence of 41 kDa protein |
| 22 | ykoY nucleic acid sequence, 277–1089 |
| 23 | YkoY amino acid sequence, 271 amino acids |
| 24 | ykoZ nucleic acid sequence, 1460–2167 |
| 25 | YkoZ amino acid sequence, 236 amino acids |
| 26 | ykrM nucleic acid sequence, 6959–7916 (partial) |
| 27 | YkrM amino acid sequence, 319 amino acids (partial) |
| 28 | sspD nucleic acid sequence, 2419–2225 reverse complement |
| 29 | SspD amino acid sequence, 65 amino acids |

DEFINITIONS

The following definitions are provided in order to aid those skilled in the art in understanding the detailed description of the present invention.

"C-terminal region" refers to the region of a peptide, polypeptide, or protein chain from the middle thereof to the end that carries the amino acid having a free a carboxyl group (the C-terminus).

"CoA" refers to coenzyme A.

The phrases "coding sequence", "open reading frame", and "structural sequence" refer to the region of continuous sequential nucleic acid triplets encoding a protein, polypeptide, or peptide sequence.

The term "encoding DNA" or "encoding nucleic acid" refers to chromosomal nucleic acid, plasmid nucleic acid, cDNA, or synthetic nucleic acid which codes on expression for any of the proteins or fusion proteins discussed herein.

The term "genome" as it applies to bacteria encompasses both the chromosome and plasmids within a bacterial host cell. Encoding nucleic acids of the present invention introduced into bacterial host cells can therefore be either chromosomally-integrated or plasmid-localized. The term "genome" as it applies to plant cells encompasses not only chromosomal DNA found within the nucleus, but organelle DNA found within subcellular components of the cell. Nucleic acids of the present invention introduced into plant cells can therefore be either chromosomally-integrated or organelle-localized.

"Identity" refers to the degree of similarity between two nucleic acid or protein sequences. An alignment of the two sequences is performed by a suitable computer program. A widely used and accepted computer program for performing sequence alignments is CLUSTALW v1.6 (Thompson, et al. *Nucl. Acids Res.*, 22: 4673–4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between 200 and a 400 amino acid proteins, they are 50 percent identical with respect to the shorter sequence. If the shorter sequence is less than 150 bases or 50 amino acids in length, the number of matches are divided by 150 (for nucleic acids) or 50 (for proteins); and multiplied by 100 to obtain a percent identity.

The terms "microbe" or "microorganism" refer to algae, bacteria, fungi, and protozoa.

"N-terminal region" refers to the region of a peptide, polypeptide, or protein chain from the amino acid having a free amino group to the middle of the chain.

"Nucleic acid" refers to ribonucleic acid (RNA) and deoxyribonucleic acid (DNA).

A "nucleic acid segment" is a nucleic acid molecule that has been isolated free of total genomic DNA of a particular species, or that has been synthesized. Included with the term "nucleic acid segment" are DNA segments, recombinant vectors, plasmids, cosmids, phagemids, phage, viruses, etcetera.

"Overexpression" refers to the expression of a polypeptide or protein encoded by a DNA introduced into a host cell, wherein said polypeptide or protein is either not normally present in the host cell, or wherein said polypeptide or protein is present in said host cell at a higher level than that normally expressed from the endogenous gene encoding said polypeptide or protein.

The term "plastid" refers to the class of plant cell organelles that includes amyloplasts, chloroplasts, chromoplasts, elaioplasts, eoplasts, etioplasts, leucoplasts, and proplastids. These organelles are self-replicating, and contain what is commonly referred to as the "chloroplast genome," a circular DNA molecule that ranges in size from about 120 to about 217 kb, depending upon the plant species, and which usually contains an inverted repeat region (Fosket, Plant growth and Development, Academic Press, Inc., San Diego, Calif., p. 132, 1994).

"Polyadenylation signal" or "polyA signal" refers to a nucleic acid sequence located 3' to a coding region that directs the addition of adenylate nucleotides to the 3' end of the mRNA transcribed from the coding region.

The term "polyhydroxyalkanoate (or PHA) synthase" refers to enzymes that convert hydroxyacyl-CoAs to polyhydroxyalkanoates and free CoA.

The term "promoter" or "promoter region" refers to a nucleic acid sequence, usually found upstream (5') to a coding sequence, that controls expression of the coding sequence by controlling production of messenger RNA (mRNA) by providing the recognition site for RNA polymerase and/or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant vector, as demonstrated by its ability to produce mRNA.

"Regeneration" refers to the process of growing a plant from a plant cell (e.g., plant protoplast or explant).

"Transformation" refers to a process of introducing an exogenous nucleic acid sequence (e.g., a vector, recombinant nucleic acid molecule) into a cell or protoplast in which that exogenous nucleic acid is incorporated into a chromosome or is capable of autonomous replication.

A "transformed cell" is a cell whose nucleic acid has been altered by the introduction of an exogenous nucleic acid molecule into that cell.

A "transformed plant" or "transgenic plant" is a plant whose nucleic acid has been altered by the introduction of an exogenous nucleic acid molecule into that plant, or by the introduction of an exogenous nucleic acid molecule into a plant cell from which the plant was regenerated or derived.

DETAILED DESCRIPTION OF THE INVENTION

This invention was developed in the pursuit of proteins which are associated with polyhydroxyalkanoate inclusion bodies, and in the pursuit of novel nucleic acid and amino acid sequences from the bacteria *Bacillus megaterium*. A 7,916 base pair nucleic acid fragment was isolated and sequenced (SEQ ID NO:1). This fragment was found to contain nine open reading frames, five of which encode proteins suspected of being involved in polyhydroxyalkanoate biosynthesis.

Genomic Fragment

An embodiment of the invention is a nucleic acid segment at least about 80% identical to SEQ ID NO:1. More preferably, the nucleic acid segment is at least about 82%, 84%, 86%, 88%, 90%, 92%, 94%, 96%, 98%, 99%, 99.5%, or 100% identical to SEQ ID NO:1. Alternatively, the nucleic acid segment may be a nucleic acid segment that hybridizes under stringent conditions to SEQ ID NO:1, or to the complement thereof. The nucleic acid segment may be obtained from a natural source, may be mutagenized, may be genetically engineered by mutagenesis or other methods, or may be synthetic.

The invention is further directed to nucleic acid segments, proteins, recombinant vectors, recombinant host cells, genetically transformed plant cells, genetically transformed plants, methods of preparing host cells, methods of preparing plants, fusion proteins, and nucleic acid segments encoding fusion proteins.

phaP and PhaP

A nucleic acid segment may comprise a nucleic acid sequence encoding a polyhydroxyalkanoate inclusion body associated protein, wherein the nucleic acid sequence is selected from the group consisting of: a nucleic acid sequence at least about 80% identical to SEQ ID NO:2; a nucleic acid sequence that hybridizes under stringent conditions to SEQ ID NO:2 or the complement thereof, a nucleic acid sequence encoding a protein at least about 80% identical to SEQ ID NO:3; and a nucleic acid sequence encoding a protein that is immunoreactive with an antibody prepared using SEQ ID NO:3 as an antigen, the antibody being immunoreactive with SEQ ID NO:3. More preferably, the nucleic acid sequence is at least about 82%, 84%, 86%, 88%, 90%, 92%, 94%, 96%, 98%, 99%, 99.5%, or 100% identical to SEQ ID NO:2. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:3.

An isolated polyhydroxyalkanoate inclusion body associated protein may comprise an amino acid sequence selected from the group consisting of: an amino acid sequence at least about 80% identical to SEQ ID NO:3; and an amino acid sequence that is immunoreactive with an antibody prepared using SEQ ID NO:3 as an antigen, the antibody being immunoreactive with SEQ ID NO:3. The protein is preferably at least about 82%, 84%, 86%, 88%, 90%, 92%, 94%, 96%, 98%, 99%, 99.5%, or 100% identical to SEQ ID NO:3

A recombinant vector may comprise in the 5' to 3' direction: a) a promoter that directs transcription of a structural nucleic acid sequence encoding a polyhydroxyalkanoate inclusion body associated protein; b) a structural nucleic acid sequence encoding a polyhydroxyalkanoate inclusion body associated protein; wherein the structural nucleic acid sequence is selected from the group consisting of: a nucleic acid sequence at least about 80% identical to SEQ ID NO:2; a nucleic acid sequence that hybridizes under stringent conditions to SEQ ID NO:2 or the complement thereof; a nucleic acid sequence encoding a protein at least about 80% identical to SEQ ID NO:3; and a nucleic acid sequence encoding a protein that is immunoreactive with an antibody prepared using SEQ ID NO:3 as an antigen, the antibody being immunoreactive with SEQ ID NO:3; and c) a 3' transcription terminator. More preferably, the nucleic acid sequence is at least about 82%, 84%, 86%, 88%, 90%, 92%, 94%, 96%, 98%, 99%, 99.5%, or 100% identical to SEQ ID NO:2. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:3. The promoter may generally be any promoter, and more preferably is a tissue selective or tissue specific promoter. The promoter may be constitutive or inducible. The promoter may be a viral promoter. The promoter may be a CMV35S, enhanced CMV35S, an FMV35S, a Lesquerella hydroxylase, or a 7S conglycinin promoter.

A recombinant host cell may comprise a nucleic acid segment encoding a polyhydroxyalkanoate inclusion body associated protein, wherein the nucleic acid segment is selected from the group consisting of: a nucleic acid sequence at least about 80% identical to SEQ ID NO:2; a nucleic acid sequence that hybridizes under stringent conditions to SEQ ID NO:2 or the complement thereof; a nucleic acid sequence encoding a protein at least about 80% identical to SEQ ID NO:3; and a nucleic acid sequence encoding a protein that is immunoreactive with an antibody prepared using SEQ ID NO:3 as an antigen, the antibody being immunoreactive with SEQ ID NO:3. More preferably, the nucleic acid sequence is at least about 82%, 84%, 86%, 88%, 90%, 92%, 94%, 96%, 98%, 99%, 99.5%, or 100% identical to SEQ ID NO:2. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:3. The host cell may generally be any host cell, and preferably is a bacterial, fungal, mammalian, or plant cell. The bacterial cell is preferably an *Escherichia coli*, Bacillus, Pseudomonas, or *Ralstonia eutropha* cell. The fungal cell is preferably a *Saccharomyces cerevisiae* or *Schizosaccharomyces pombe* cell. The plant cell is preferably a tobacco, wheat, potato, Arabidopsis, and high oil seed plants such as corn, soybean, canola, oil seed rape, sugarbeet, sunflower, flax, peanut, sugarcane, switchgrass, or alfalfa cell.

A genetically transformed plant cell may comprise in the 5' to 3' direction: a) a promoter that directs transcription of a structural nucleic acid sequence encoding a polyhydroxyalkanoate inclusion body associated protein; b) a structural nucleic acid sequence encoding a polyhydroxyalkanoate inclusion body associated protein; wherein the structural nucleic acid sequence is selected from the group consisting of: a nucleic acid sequence at least about 80% identical to SEQ ID NO:2; a nucleic acid sequence that hybridizes under stringent conditions to SEQ ID NO:2 or the complement thereof; a nucleic acid sequence encoding a protein at least about 80% identical to SEQ ID NO:3; and a nucleic acid sequence encoding a protein that is immunoreactive with an antibody prepared using SEQ ID NO:3 as an antigen, the antibody being immunoreactive with SEQ ID NO:3; c) a 3' transcription terminator; and d) a 3' polyadenylation signal sequence that directs the addition of polyadenylate nucleotides to the 3' end of RNA transcribed from the structural nucleic acid sequence. More preferably, the nucleic acid sequence is at least about 82%, 84%, 86%, 88%, 90%, 92%, 94%, 96%, 98%, 99%, 99.5%, or 100% identical to SEQ ID NO:2. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:3. The plant may generally be any plant, and more preferably a monocot, dicot, or conifer. The plant is preferably a tobacco, wheat, potato, Arabidopsis, and high oil seed plants such as corn, soybean, canola, oil seed rape, sugarbeet, sunflower, flax, peanut, sugarcane, switchgrass, or alfalfa plant.

A method of preparing host cells useful to produce a polyhydroxyalkanoate inclusion body associated protein may comprise a) selecting a host cell; b) transforming the selected host cell with a recombinant vector having a structural nucleic acid sequence encoding a polyhydroxyalkanoate inclusion body associated protein, wherein the structural nucleic acid sequence is selected from the group consisting of: a nucleic acid sequence at least about 80% identical to SEQ ID NO:2; a nucleic acid sequence that hybridizes under stringent conditions to SEQ ID NO:2 or the complement thereof; a nucleic acid sequence encoding a protein at least about 80% identical to SEQ ID NO:3; and a nucleic acid sequence encoding a protein that is immunoreactive with an antibody prepared using SEQ ID NO:3 as an antigen, the antibody being immunoreactive with SEQ ID NO:3; and c) obtaining transformed host cells. More preferably, the nucleic acid sequence is at least about 82%, 84%, 86%, 88%, 90%, 92%, 94%, 96%, 98%, 99%, 99.5%, or 100% identical to SEQ ID NO:2. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:3. The host cell may generally be any host cell, and preferably is a bacterial, fungal, mammalian, or plant cell. The bacterial cell is preferably an *Escherichia coli,* Bacillus, Pseudomonas, or *Ralstonia eutropha* cell. The fungal cell is preferably a *Saccharomyces cerevisiae* or *Schizosaccharomyces pombe* cell. The plant cell is preferably a tobacco, wheat, potato, Arabidopsis, and high oil seed plants such as corn, soybean, canola, oil seed rape, sugarbeet, sunflower, flax, peanut, sugarcane, switchgrass, or alfalfa cell.

A method of preparing plants useful to produce a polyhydroxyalkanoate inclusion body associated protein may comprise a) selecting a host plant cell; b) transforming the selected host plant cell with a recombinant vector having a structural nucleic acid sequence encoding a polyhydroxyalkanoate inclusion body associated protein, wherein the structural nucleic acid sequence is selected from the group consisting of: a nucleic acid sequence at least about 80% identical to SEQ ID NO:2; a nucleic acid sequence that hybridizes under stringent conditions to SEQ ID NO:2 or the complement thereof; a nucleic acid sequence encoding a protein at least about 80% identical to SEQ ID NO:3; and a nucleic acid sequence encoding a protein that is immunoreactive with an antibody prepared using SEQ ID NO:3 as an antigen, the antibody being immunoreactive with SEQ ID NO:3; c) obtaining transformed host plant cells; and d) regenerating the transformed host plant cells. More preferably, the nucleic acid sequence is at least about 82%, 84%, 86%, 88%, 90%, 92%, 94%, 96%, 98%, 99%, 99.5%, or 100% identical to SEQ ID NO:2. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:3. The plant (and plant cell) may generally be any plant, and more preferably a monocot, dicot, or conifer. The plant is preferably a tobacco, wheat, potato, Arabidopsis, and high oil seed plants such as corn, soybean, canola, oil seed rape, sugarbeet, sunflower, flax, peanut, sugarcane, switchgrass, or alfalfa plant.

The invention also relates to fusion proteins. A fusion protein may comprise a green fluorescent protein subunit; and a polyhydroxyalkanoate inclusion body associated protein subunit; wherein the polyhydroxyalkanoate inclusion body associated protein subunit comprises an amino acid sequence selected from the group consisting of: an amino acid sequence at least about 80% identical to SEQ ID NO:3; and an amino acid sequence that is immunoreactive with an antibody prepared using SEQ ID NO:3 as an antigen, the antibody being immunoreactive with SEQ ID NO:3. The polyhydroxyalkanoate inclusion body associated protein subunit is preferably at least about 82%, 84%, 86%, 88%, 90%, 92%, 94%, 96%, 98%, 99%, 99.5%, or 100% identical to SEQ ID NO:3.

A nucleic acid segment encoding a fusion protein may comprise a nucleic acid sequence encoding a green fluorescent protein subunit; and a nucleic acid sequence encoding a polyhydroxyalkanoate inclusion body associated protein subunit; wherein the nucleic acid sequence encoding a polyhydroxyalkanoate inclusion body associated protein subunit is selected from the group consisting of: a nucleic acid sequence at least about 80% identical to SEQ ID NO:2; a nucleic acid sequence that hybridizes under stringent conditions to SEQ ID NO:2 or the complement thereof; a nucleic acid sequence encoding a protein at least about 80% identical to SEQ ID NO:3; and a nucleic acid sequence encoding a protein that is immunoreactive with an antibody prepared using SEQ ID NO:3 as an antigen, the antibody being immunoreactive with SEQ ID NO:3. More preferably, the nucleic acid sequence is at least about 82%, 84%, 86%, 88%, 90%, 92%, 94%, 96%, 98%, 99%, 99.5%, or 100% identical to SEQ ID NO:2. The nucleic acid sequence may be obtained from a natural source, may be mutagenized, may be genetically engineered by mutagenesis or other methods, or may be synthetic. The nucleic acid sequence preferably encodes a protein subunit at least about 82%, 84%, 86%, 88%, 90%, 92%, 94%, 96%, 98%, 99%, 99.5%, or 100% identical to SEQ ID NO:3.

phaQ and PhaQ

A nucleic acid segment may comprise a nucleic acid sequence encoding a polyhydroxyalkanoate inclusion body associated protein, wherein the nucleic acid sequence is selected from the group consisting of: a nucleic acid sequence at least about 80% identical to SEQ ID NO:4; a nucleic acid sequence that hybridizes under stringent conditions to SEQ ID NO:4 or the complement thereof; a nucleic acid sequence encoding a protein at least about 80% identical to SEQ ID NO:5; and a nucleic acid sequence encoding a protein that is immunoreactive with an antibody prepared using SEQ ID NO:5 as an antigen, the antibody being immunoreactive with SEQ ID NO:5. More preferably, the nucleic acid sequence is at least about 82%, 84%, 86%, 88%, 90%, 92%, 94%, 96%, 98%, 99%, 99.5%, or 100% identical to SEQ ID NO:4. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:5.

An isolated polyhydroxyalkanoate inclusion body associated protein may comprise an amino acid sequence selected from the group consisting of: an amino acid sequence at least about 80% identical to SEQ ID NO:5; and an amino acid sequence that is immunoreactive with an antibody prepared using SEQ ID NO:5 as an antigen, the antibody being immunoreactive with SEQ ID NO:5. The protein is preferably at least about 82%, 84%, 86%, 88%, 90%, 92%, 94%, 96%, 98%, 99%, 99.5%, or 100% identical to SEQ ID NO:5

A recombinant vector may comprise in the 5' to 3' direction: a) a promoter that directs transcription of a structural nucleic acid sequence encoding a polyhydroxyalkanoate inclusion body associated protein; b) a structural nucleic acid sequence encoding a polyhydroxyalkanoate inclusion body associated protein; wherein the structural nucleic acid sequence is selected from the group consisting of: a nucleic acid sequence at least about 80% identical to SEQ ID NO:4; a nucleic acid sequence that hybridizes under stringent conditions to SEQ ID NO:4 or the complement thereof; a nucleic acid sequence encoding a protein at least about 80% identical to SEQ ID NO:5; and a nucleic acid sequence encoding a protein that is immunoreactive with an antibody prepared using SEQ ID NO:5 as an antigen, the antibody being immunoreactive with SEQ ID NO:5; and c) a 3' transcription terminator. More preferably, the nucleic acid sequence is at least about 82%, 84%, 86%, 88%, 90%, 92%, 94%, 96%, 98%, 99%, 99.5%, or 100% identical to SEQ ID NO:4. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:5. The promoter may generally be any promoter, and more preferably is a tissue selective or tissue specific promoter. The promoter may be constitutive or inducible. The promoter may be a viral promoter. The promoter may be a CMV35S, enhanced CMV35S, an FMV35S, a Lesquerella hydroxylase, or a 7S conglycinin promoter.

A recombinant host cell may comprise a nucleic acid segment encoding a polyhydroxyalkanoate inclusion body associated protein, wherein the nucleic acid segment is selected from the group consisting of: a nucleic acid sequence at least about 80% identical to SEQ ID NO:4; a nucleic acid sequence that hybridizes under stringent conditions to SEQ ID NO:4 or the complement thereof, a nucleic acid sequence encoding a protein at least about 80% identical to SEQ ID NO:5; and a nucleic acid sequence encoding a protein that is immunoreactive with an antibody prepared using SEQ ID NO:5 as an antigen, the antibody being immunoreactive with SEQ ID NO:5. More preferably, the nucleic acid sequence is at least about 82%, 84%, 86%, 88%, 90%, 92%, 94%, 96%, 98%, 99%, 99.5%, or 100% identical to SEQ ID NO:4. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:5. The host cell may generally be any host cell, and preferably is a bacterial, fungal, mammalian, or plant cell. The bacterial cell is preferably an *Escherichia coli*, Bacillus, Pseudomonas, or *Ralstonia eutropha* cell. The fungal cell is preferably a *Saccharomyces cerevisiae* or *Schizosaccharomyces pombe* cell. The plant cell is preferably a tobacco, wheat, potato, Arabidopsis, and high oil seed plants such as corn, soybean, canola, oil seed rape, sugarbeet, sunflower, flax, peanut, sugarcane, switchgrass, or alfalfa cell.

A genetically transformed plant cell may comprise in the 5' to 3' direction: a) a promoter that directs transcription of a structural nucleic acid sequence encoding a polyhydroxyalkanoate inclusion body associated protein; b) a structural nucleic acid sequence encoding a polyhydroxyalkanoate inclusion body associated protein; wherein the structural nucleic acid sequence is selected from the group consisting of: a nucleic acid sequence at least about 80% identical to SEQ ID NO:4; a nucleic acid sequence that hybridizes under stringent conditions to SEQ ID NO:4 or the complement thereof; a nucleic acid sequence encoding a protein at least about 80% identical to SEQ ID NO:5; and a nucleic acid sequence encoding a protein that is immunoreactive with an antibody prepared using SEQ ID NO:5 as an antigen, the antibody being immunoreactive with SEQ ID NO:5; c) a 3' transcription terminator; and d) a 3' polyadenylation signal sequence that directs the addition of polyadenylate nucleotides to the 3' end of RNA transcribed from the structural nucleic acid sequence. More preferably, the nucleic acid sequence is at least about 82%, 84%, 86%, 88%, 90%, 92%, 94%, 96%, 98%, 99%, 99.5%, or 100% identical to SEQ ID NO:4. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:5. The plant may generally be any plant, and more preferably a monocot, dicot, or conifer. The plant is preferably a tobacco, wheat, potato, Arabidopsis, and high oil seed plants such as corn, soybean, canola, oil seed rape, sugarbeet, sunflower, flax, peanut, sugarcane, switchgrass, or alfalfa plant.

A method of preparing host cells useful to produce a polyhydroxyalkanoate inclusion body associated protein may comprise a) selecting a host cell; b) transforming the selected host cell with a recombinant vector having a structural nucleic acid sequence encoding a polyhydroxyalkanoate inclusion body associated protein, wherein the structural nucleic acid sequence is selected from the group consisting of: a nucleic acid sequence at least about 80% identical to SEQ ID NO:4; a nucleic acid sequence that hybridizes under stringent conditions to SEQ ID NO:4 or the complement thereof; a nucleic acid sequence encoding a protein at least about 80% identical to SEQ ID NO:5; and a nucleic acid sequence encoding a protein that is immunoreactive with an antibody prepared using SEQ ID NO:5 as an antigen, the antibody being immunoreactive with SEQ ID NO:5; and c) obtaining transformed host cells. More preferably, the nucleic acid sequence is at least about 82%, 84%, 86%, 88%, 90%, 92%, 94%, 96%, 98%, 99%, 99.5%, or 100% identical to SEQ ID NO:4. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:5. The host cell may generally be any host cell, and preferably is a bacterial, fungal, mammalian, or plant cell. The bacterial cell is preferably an *Escherichia coli*, Bacillus, Pseudomonas, or *Ralstonia eutropha* cell. The fungal cell is preferably a *Saccharomyces cerevisiae* or *Schizosaccharomyces pombe* cell. The plant cell is preferably a tobacco, wheat, potato, Arabidopsis, and high oil seed plants such as corn, soybean, canola, oil seed rape, sugarbeet, sunflower, flax, peanut, sugarcane, switchgrass, or alfalfa cell.

A method of preparing plants useful to produce a polyhydroxyalkanoate inclusion body associated protein may comprise a) selecting a host plant cell; b) transforming the selected host plant cell with a recombinant vector having a structural nucleic acid sequence encoding a polyhydroxyalkanoate inclusion body associated protein, wherein the structural nucleic acid sequence is selected from the group consisting of: a nucleic acid sequence at least about 80% identical to SEQ ID NO:4; a nucleic acid sequence that hybridizes under stringent conditions to SEQ ID NO:4 or the complement thereof; a nucleic acid sequence encoding a protein at least about 80% identical to SEQ ID NO:5; and a nucleic acid sequence encoding a protein that is immunoreactive with an antibody prepared using SEQ ID NO:5 as an antigen, the antibody being immunoreactive with SEQ ID NO:5; c) obtaining transformed host plant cells; and d) regenerating the transformed host plant cells. More preferably, the nucleic acid sequence is at least about 82%, 84%, 86%, 88%, 90%, 92%, 94%, 96%, 98%, 99%, 99.5%, or 100% identical to SEQ ID NO:4. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:5. The plant (and plant cell) may generally be any plant, and more preferably a monocot, dicot, or conifer. The plant is preferably a tobacco, wheat, potato, Arabidopsis, and high oil seed plants such as corn, soybean, canola, oil seed rape, sugarbeet, sunflower, flax, peanut, sugarcane, switchgrass, or alfalfa plant.

The invention also relates to fusion proteins. A fusion protein may comprise a green fluorescent protein subunit; and a polyhydroxyalkanoate inclusion body associated protein subunit; wherein the polyhydroxyalkanoate inclusion body associated protein subunit comprises an amino acid sequence selected from the group consisting of: an amino acid sequence at least about 80% identical to SEQ ID NO:5; and an amino acid sequence that is immunoreactive with an antibody prepared using SEQ ID NO:5 as an antigen, the antibody being immunoreactive with SEQ ID NO:5. The polyhydroxyalkanoate inclusion body associated protein subunit is preferably at least about 82%, 84%, 86%, 88%, 90%, 92%, 94%, 96%, 98%, 99%, 99.5%, or 100% identical to SEQ ID NO:5.

A nucleic acid segment encoding a fusion protein may comprise a nucleic acid sequence encoding a green fluorescent protein subunit; and a nucleic acid sequence encoding a polyhydroxyalkanoate inclusion body associated protein subunit; wherein the nucleic acid sequence encoding a polyhydroxyalkanoate inclusion body associated protein subunit is selected from the group consisting of: a nucleic acid sequence at least about 80% identical to SEQ ID NO:4; a nucleic acid sequence that hybridizes under stringent conditions to SEQ ID NO:4 or the complement thereof; a nucleic acid sequence encoding a protein at least about 80% identical to SEQ ID NO:5; and a nucleic acid sequence encoding a protein that is immunoreactive with an antibody prepared using SEQ ID NO:5 as an antigen, the antibody being immunoreactive with SEQ ID NO:5. More preferably, the nucleic acid sequence is at least about 82%, 84%, 86%, 88%, 90%, 92%, 94%, 96%, 98%, 99%, 99.5%, or 100% identical to SEQ ID NO:4. The nucleic acid sequence may be obtained from a natural source, may be mutagenized, may be genetically engineered by mutagenesis or other methods, or may be synthetic. The nucleic acid sequence preferably encodes a protein subunit at least about 82%, 84%, 86%, 88%, 90%, 92%, 94%, 96%, 98%, 99%, 99.5%, or 100% identical to SEQ ID NO:5.

phaR and PhaR

A nucleic acid segment may comprise a nucleic acid sequence encoding a polyhydroxyalkanoate inclusion body associated protein, wherein the nucleic acid sequence is selected from the group consisting of: a nucleic acid sequence at least about 80% identical to SEQ ID NO:6; a nucleic acid sequence that hybridizes under stringent conditions to SEQ ID NO:6 or the complement thereof; a nucleic acid sequence encoding a protein at least about 80% identical to SEQ ID NO:7; and a nucleic acid sequence encoding a protein that is immunoreactive with an antibody prepared using SEQ ID NO:7 as an antigen, the antibody being immunoreactive with SEQ ID NO:7. More preferably, the nucleic acid sequence is at least about 82%, 84%, 86%, 88%, 90%, 92%, 94%, 96%, 98%, 99%, 99.5%, or 100% identical to SEQ ID NO:6. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:7.

An isolated polyhydroxyalkanoate inclusion body associated protein may comprise an amino acid sequence selected from the group consisting of: an amino acid sequence at least about 80% identical to SEQ ID NO:7; and an amino acid sequence that is immunoreactive with an antibody prepared using SEQ ID NO:7 as an antigen, the antibody being immunoreactive with SEQ ID NO:7. The protein is preferably at least about 82%, 84%, 86%, 88%, 90%, 92%, 94%, 96%, 98%, 99%, 99.5%, or 100% identical to SEQ ID NO:7.

A recombinant vector may comprise in the 5' to 3' direction: a) a promoter that directs transcription of a structural nucleic acid sequence encoding a polyhydroxyalkanoate inclusion body associated protein; b) a structural nucleic acid sequence encoding a polyhydroxyalkanoate inclusion body associated protein; wherein the structural nucleic acid sequence is selected from the group consisting of: a nucleic acid sequence at least about 80% identical to SEQ ID NO:6; a nucleic acid sequence that hybridizes under stringent conditions to SEQ ID NO:6 or the complement thereof; a nucleic acid sequence encoding a protein at least about 80% identical to SEQ ID NO:7; and a nucleic acid sequence encoding a protein that is immunoreactive with an antibody prepared using SEQ ID NO:7 as an antigen, the antibody being immunoreactive with SEQ ID NO:7; and c) a 3' transcription terminator. More preferably, the nucleic acid sequence is at least about 82%, 84%, 86%, 88%, 90%, 92%, 94%, 96%, 98%, 99%, 99.5%, or 100% identical to SEQ ID NO:6. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:7. The promoter may generally be any promoter, and more preferably is a tissue selective or tissue specific promoter. The promoter may be constitutive or inducible. The promoter may be a viral promoter. The promoter may be a CMV35S, enhanced CMV35S, an FMV35S, a Lesquerella hydroxylase, or a 7S conglycinin promoter.

A recombinant host cell may comprise a nucleic acid segment encoding a polyhydroxyalkanoate inclusion body associated protein, wherein the nucleic acid segment is selected from the group consisting of: a nucleic acid sequence at least about 80% identical to SEQ ID NO:6; a nucleic acid sequence that hybridizes under stringent conditions to SEQ ID NO:6 or the complement thereof; a nucleic acid sequence encoding a protein at least about 80% identical to SEQ ID NO:7; and a nucleic acid sequence encoding a protein that is immunoreactive with an antibody prepared using SEQ ID NO:7 as an antigen, the antibody being immunoreactive with SEQ ID NO:7. More preferably, the nucleic acid sequence is at least about 82%, 84%, 86%, 88%, 90%, 92%, 94%, 96%, 98%, 99%, 99.5%, or 100% identical to SEQ ID NO:6. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:7. The host cell may generally be any host cell, and preferably is a bacterial, fungal, mammalian, or plant cell. The bacterial cell is preferably an *Escherichia coli*, Bacillus, Pseudomonas, or *Ralstonia eutropha* cell. The fungal cell is preferably a *Saccharomyces cerevisiae* or *Schizosaccharomyces pombe* cell. The plant cell is preferably a tobacco, wheat, potato, Arabidopsis, and high oil seed plants such as corn, soybean, canola, oil seed rape, sugarbeet, sunflower, flax, peanut, sugarcane, switchgrass, or alfalfa cell.

A genetically transformed plant cell may comprise in the 5' to 3' direction: a) a promoter that directs transcription of a structural nucleic acid sequence encoding a polyhydroxyalkanoate inclusion body associated protein; b) a structural nucleic acid sequence encoding a polyhydroxyalkanoate inclusion body associated protein; wherein the structural nucleic acid sequence is selected from the group consisting of: a nucleic acid sequence at least about 80% identical to SEQ ID NO:6; a nucleic acid sequence that hybridizes under stringent conditions to SEQ ID NO:6 or the complement thereof; a nucleic acid sequence encoding a protein at least about 80% identical to SEQ ID NO:7; and a nucleic acid sequence encoding a protein that is immunoreactive with an antibody prepared using SEQ ID NO:7 as an antigen, the antibody being immunoreactive with SEQ ID NO:7; c) a 3' transcription terminator; and d) a 3' polyadenylation signal sequence that directs the addition of polyadenylate nucleotides to the 3' end of RNA transcribed from the structural nucleic acid sequence. More preferably, the nucleic acid sequence is at least about 82%, 84%, 86%, 88%, 90%, 92%, 94%, 96%, 98%, 99%, 99.5%, or 100% identical to SEQ ID NO:6. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:7. The plant may generally be any plant, and more preferably a monocot, dicot, or conifer. The plant is preferably a tobacco, wheat, potato, Arabidopsis, and high oil seed plants such as corn, soybean, canola, oil seed rape, sugarbeet, sunflower, flax, peanut, sugarcane, switchgrass, or alfalfa plant.

A method of preparing host cells useful to produce a polyhydroxyalkanoate inclusion body associated protein may comprise a) selecting a host cell; b) transforming the selected host cell with a recombinant vector having a structural nucleic acid sequence encoding a polyhydroxyalkanoate inclusion body associated protein, wherein the structural nucleic acid sequence is selected from the group consisting of: a nucleic acid sequence at least about 80% identical to SEQ ID NO:6; a nucleic acid sequence that hybridizes under stringent conditions to SEQ ID NO:6 or the complement thereof; a nucleic acid sequence encoding a protein at least about 80% identical to SEQ ID NO:7; and a nucleic acid sequence encoding a protein that is immunoreactive with an antibody prepared using SEQ ID NO:7 as an antigen, the antibody being immunoreactive with SEQ ID NO:7; and c) obtaining transformed host cells. More preferably, the nucleic acid sequence is at least about 82%, 84%, 86%, 88%, 90%, 92%, 94%, 96%, 98%, 99%, 99.5%, or 100% identical to SEQ ID NO:6. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:7. The host cell may generally be any host cell, and preferably is a bacterial, fungal, mammalian, or plant cell. The bacterial cell is preferably an *Escherichia coli*, Bacillus, Pseudomonas, or *Ralstonia eutropha* cell. The fungal cell is preferably a *Saccharomyces cerevisiae* or *Schizosaccharomyces pombe* cell. The plant cell is preferably a tobacco, wheat, potato, Arabidopsis, and high oil seed plants such as corn, soybean, canola, oil seed rape, sugarbeet, sunflower, flax, peanut, sugarcane, switchgrass, or alfalfa cell.

A method of preparing plants useful to produce a polyhydroxyalkanoate inclusion body associated protein may comprise a) selecting a host plant cell; b) transforming the selected host plant cell with a recombinant vector having a structural nucleic acid sequence encoding a polyhydroxyalkanoate inclusion body associated protein, wherein the structural nucleic acid sequence is selected from the group consisting of: a nucleic acid sequence at least about 80% identical to SEQ ID NO:6; a nucleic acid sequence that hybridizes under stringent conditions to SEQ ID NO:6 or the complement thereof; a nucleic acid sequence encoding a protein at least about 80% identical to SEQ ID NO:7; and a nucleic acid sequence encoding a protein that is immunoreactive with an antibody prepared using SEQ ID NO:7 as an antigen, the antibody being immunoreactive with SEQ ID NO:7; c) obtaining transformed host plant cells; and d) regenerating the transformed host plant cells. More preferably, the nucleic acid sequence is at least about 82%, 84%, 86%, 88%, 90%, 92%, 94%, 96%, 98%, 99%, 99.5%, or 100% identical to SEQ ID NO:6. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:7. The plant (and plant cell) may generally be any plant, and more preferably a monocot, dicot, or conifer. The plant is preferably a tobacco, wheat, potato, Arabidopsis, and high oil seed plants such as corn, soybean, canola, oil seed rape, sugarbeet, sunflower, flax, peanut, sugarcane, switchgrass, or alfalfa plant.

The invention also relates to fusion proteins. A fusion protein may comprise a green fluorescent protein subunit; and a polyhydroxyalkanoate inclusion body associated protein subunit; wherein the polyhydroxyalkanoate inclusion body associated protein subunit comprises an amino acid sequence selected from the group consisting of: an amino acid sequence at least about 80% identical to SEQ ID NO:7; and an amino acid sequence that is immunoreactive with an antibody prepared using SEQ ID NO:7 as an antigen, the antibody being immunoreactive with SEQ ID NO:7. The polyhydroxyalkanoate inclusion body associated protein subunit is preferably at least about 82%,84%,86%,88%, 90%,92%,94%,96%,98%,99%, 99.5%, or 100% identical to SEQ ID NO:7.

A nucleic acid segment encoding a fusion protein may comprise a nucleic acid sequence encoding a green fluorescent protein subunit; and a nucleic acid sequence encoding a polyhydroxyalkanoate inclusion body associated protein subunit; wherein the nucleic acid sequence encoding a polyhydroxyalkanoate inclusion body associated protein subunit is selected from the group consisting of: a nucleic acid sequence at least about 80% identical to SEQ ID NO:6; a nucleic acid sequence that hybridizes under stringent conditions to SEQ ID NO:6 or the complement thereof; a nucleic acid sequence encoding a protein at least about 80% identical to SEQ ID NO:7; and a nucleic acid sequence encoding a protein that is immunoreactive with an antibody prepared using SEQ ID NO:7 as an antigen, the antibody being immunoreactive with SEQ ID NO:7. More preferably, the nucleic acid sequence is at least about 82%, 84%, 86%, 88%, 90%, 92%, 94%, 96%, 98%, 99%, 99.5%, or 100% identical to SEQ ID NO:6. The nucleic acid sequence may be obtained from a natural source, may be mutagenized, may be genetically engineered by mutagenesis or other methods, or may be synthetic. The nucleic acid sequence preferably encodes a protein subunit at least about 82%, 84%, 86%, 88%, 90%, 92%, 94%, 96%, 98%, 99%, 99.5%, or 100% identical to SEQ ID NO:7.

phaB and PhaB

A nucleic acid segment may comprise a nucleic acid sequence encoding a 3-keto-acyl-CoA reductase protein, wherein the nucleic acid sequence is selected from the group consisting of: a nucleic acid sequence at least about 80% identical to SEQ ID NO:8; a nucleic acid sequence that hybridizes under stringent conditions to SEQ ID NO:8 or the complement thereof; a nucleic acid sequence encoding a protein at least about 80% identical to SEQ ID NO:9; and a nucleic acid sequence encoding a protein that is immunoreactive with an antibody prepared using SEQ ID NO:9 as an antigen, the antibody being immunoreactive with SEQ ID NO:9. More preferably, the nucleic acid sequence is at least about 82%, 84%, 86%, 88%, 90%, 92%, 94%, 96%, 98%, 99%, 99.5%, or 100% identical to SEQ ID NO:8. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:9.

An isolated 3-keto-acyl-CoA reductase protein may comprise an amino acid sequence selected from the group consisting of: an amino acid sequence at least about 80% identical to SEQ ID NO:9; and an amino acid sequence that is immunoreactive with an antibody prepared using. SEQ ID NO:9 as an antigen, the antibody being immunoreactive with SEQ ID NO:9. The protein is preferably at least about 82%, 84%, 86%, 88%, 90%, 92%, 94%, 96%, 98%, 99%, 99.5%, or 100% identical to SEQ ID NO:9.

A recombinant vector may comprise in the 5' to 3' direction: a) a promoter that directs transcription of a structural nucleic acid sequence encoding a 3-keto-acyl-CoA reductase protein; b) a structural nucleic acid sequence encoding a 3-keto-acyl-CoA reductase protein; wherein the structural nucleic acid sequence is selected from the group consisting of: a nucleic acid sequence at least about 80% identical to SEQ ID NO:8; a nucleic acid sequence that hybridizes under stringent conditions to SEQ ID NO:8 or the complement thereof; a nucleic acid sequence encoding a protein at least about 80% identical to SEQ ID NO:9; and a nucleic acid sequence encoding a protein that is immunoreactive with an antibody prepared using SEQ ID NO:9 as an antigen, the antibody being immunoreactive with SEQ ID NO:9; and c) a 3' transcription terminator. More preferably, the nucleic acid sequence is at least about 82%, 84%, 86%, 88%, 90%, 92%, 94%, 96%, 98%, 99%, 99.5%, or 100% identical to SEQ ID NO:8. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:9. The promoter may generally be any promoter, and more preferably is a tissue selective or tissue specific promoter. The promoter may be constitutive or inducible. The promoter may be a viral promoter. The promoter may be a CMV35S, enhanced CMV35S, an FMV35S, a Lesquerella hydroxylase, or a 7S conglycinin promoter.

A recombinant host cell may comprise a nucleic acid segment encoding a 3-keto-acyl-CoA reductase protein, wherein the nucleic acid segment is selected from the group consisting of: a nucleic acid sequence at least about 80% identical to SEQ ID NO:8; a nucleic acid sequence that hybridizes under stringent conditions to SEQ ID NO:8 or the complement thereof; a nucleic acid sequence encoding a protein at least about 80% identical to SEQ ID NO:9; and a nucleic acid sequence encoding a protein that is immunoreactive with an antibody prepared using SEQ ID NO:9 as an antigen, the antibody being immunoreactive with SEQ ID NO:9. More preferably, the nucleic acid sequence is at least about 82%, 84%, 86%, 88%, 90%, 92%, 94%, 96%, 98%, 99%, 99.5%, or 100% identical to SEQ ID NO:8. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:9. The host cell may generally be any host cell, and preferably is a bacterial, fungal, mammalian, or plant cell. The bacterial cell is preferably an *Escherichia coli*, Bacillus, Pseudomonas, or *Ralstonia eutropha* cell. The fungal cell is preferably a *Saccharomyces cerevisiae* or *Schizosaccharomyces pombe* cell. The plant cell is preferably a tobacco, wheat, potato, Arabidopsis, and high oil seed plants such as corn, soybean, canola, oil seed rape, sugarbeet, sunflower, flax, peanut, sugarcane, switchgrass, or alfalfa cell.

A genetically transformed plant cell may comprise in the 5' to 3' direction: a) a promoter that directs transcription of a structural nucleic acid sequence encoding a 3-keto-acyl-CoA reductase protein; b) a structural nucleic acid sequence encoding a 3-keto-acyl-CoA reductase protein; wherein the structural nucleic acid sequence is selected from the group consisting of: a nucleic acid sequence at least about 80% identical to SEQ ID NO:8; a nucleic acid sequence that hybridizes under stringent conditions to SEQ ID NO:8 or the complement thereof; a nucleic acid sequence encoding a protein at least about 80% identical to SEQ ID NO:9; and a nucleic acid sequence encoding a protein that is immunoreactive with an antibody prepared using SEQ ID NO:9 as an antigen, the antibody being immunoreactive with SEQ ID NO:9; c) a 3' transcription terminator; and d) a 3' polyadenylation signal sequence that directs the addition of polyadenylate nucleotides to the 3' end of RNA transcribed from the structural nucleic acid sequence. More preferably, the nucleic acid sequence is at least about 82%, 84%, 86%, 88%, 90%, 92%, 94%, 96%, 98%, 99%, 99.5%, or 100% identical to SEQ ID NO:8. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:9. The plant may generally be any plant, and more preferably a monocot, dicot, or conifer. The plant is preferably a tobacco, wheat, potato, Arabidopsis, and high oil seed plants such as corn, soybean, canola, oil seed rape, sugarbeet, sunflower, flax, peanut, sugarcane, switchgrass, or alfalfa plant.

A method of preparing host cells useful to produce a 3-keto-acyl-CoA reductase protein may comprise a) selecting a host cell; b) transforming the selected host cell with a recombinant vector having a structural nucleic acid sequence encoding a 3-keto-acyl-CoA reductase protein, wherein the structural nucleic acid sequence is selected from the group consisting of: a nucleic acid sequence at least about 80% identical to SEQ ID NO:8; a nucleic acid sequence that hybridizes under stringent conditions to SEQ ID NO:8 or the complement thereof; a nucleic acid sequence encoding a protein at least about 80% identical to SEQ ID NO:9; and a nucleic acid sequence encoding a protein that is immunoreactive with an antibody prepared using SEQ ID NO:9 as an antigen, the antibody being immunoreactive with SEQ ID NO:9; and c) obtaining transformed host cells. More preferably, the nucleic acid sequence is at least about 82%, 84%, 86%, 88%, 90%, 92%, 94%, 96%, 98%, 99%, 99.5%, or 100% identical to SEQ ID NO:8. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:9. The host cell may generally be any host cell, and preferably is a bacterial, fungal, mammalian, or plant cell. The bacterial cell is preferably an *Escherichia coli*, Bacillus, Pseudomonas, or *Ralstonia eutropha* cell. The fungal cell is preferably a *Saccharomyces cerevisiae* or *Schizosaccharomyces pombe* cell. The plant cell is preferably a tobacco, wheat, potato, Arabidopsis, and high oil seed plants such as corn, soybean, canola, oil seed rape, sugarbeet, sunflower, flax, peanut, sugarcane, switchgrass, or alfalfa cell.

A method of preparing plants useful to produce a 3-keto-acyl-CoA reductase protein may comprise a) selecting a host plant cell; b) transforming the selected host plant cell with a recombinant vector having a structural nucleic acid sequence encoding a 3-keto-acyl-CoA reductase protein, wherein the structural nucleic acid sequence is selected from the group consisting of: a nucleic acid sequence at least about 80% identical to SEQ ID NO:8; a nucleic acid sequence that hybridizes under stringent conditions to SEQ ID NO:8 or the complement thereof; a nucleic acid sequence encoding a protein at least about 80% identical to SEQ ID NO:9; and a nucleic acid sequence encoding a protein that is immunoreactive with an antibody prepared using SEQ ID NO:9 as an antigen, the antibody being immunoreactive with SEQ ID NO:9; c) obtaining transformed host plant cells; and d) regenerating the transformed host plant cells. More preferably, the nucleic acid sequence is at least about 82%, 84%, 86%, 88%, 90%, 92%, 94%, 96%, 98%, 99%, 99.5%, or 100% identical to SEQ ID NO:8. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:9. The plant (and plant cell) may generally be any plant, and more preferably a monocot, dicot, or conifer. The plant is preferably a tobacco, wheat, potato, Arabidopsis, and high oil seed plants such as corn, soybean, canola, oil seed rape, sugarbeet, sunflower, flax, peanut, sugarcane, switchgrass, or alfalfa plant.

The invention also relates to fusion proteins. A fusion protein may comprise a green fluorescent protein subunit; and a 3-keto-acyl-CoA reductase protein subunit; wherein the 3-keto-acyl-CoA reductase protein subunit comprises an amino acid sequence selected from the group consisting of: an amino acid sequence at least about 80% identical to SEQ ID NO:9; and an amino acid sequence that is immunoreactive with an antibody prepared using SEQ ID NO:9 as an antigen, the antibody being immunoreactive with SEQ ID NO:9. The 3-keto-acyl-CoA reductase protein subunit is preferably at least about 82%, 84%, 86%, 88%, 90%, 92%, 94%, 96%, 98%, 99%, 99.5%, or 100% identical to SEQ ID NO:9

A nucleic acid segment encoding a fusion protein may comprise a nucleic acid sequence encoding a green fluorescent protein subunit; and a nucleic acid sequence encoding a 3-keto-acyl-CoA reductase protein subunit; wherein the nucleic acid sequence encoding a 3-keto-acyl-CoA reductase protein subunit is selected from the group consisting of: a nucleic acid sequence at least about 80% identical to SEQ ID NO:8; a nucleic acid sequence that hybridizes under stringent conditions to SEQ ID NO:8 or the complement thereof; a nucleic acid sequence encoding a protein at least about 80% identical to SEQ ID NO:9; and a nucleic acid sequence encoding a protein that is immunoreactive with an antibody prepared using SEQ ID NO:9 as an antigen, the antibody being immunoreactive with SEQ ID NO:9. More preferably, the nucleic acid sequence is at least about 82%, 84%, 86%, 88%, 90%, 92%, 94%, 96%, 98%, 99%, 99.5%, or 100% identical to SEQ ID NO:8. The nucleic acid sequence may be obtained from a natural source, may be mutagenized, may be genetically engineered by mutagenesis or other methods, or may be synthetic. The nucleic acid sequence preferably encodes a protein subunit at least about 82%, 84%, 86%, 88%, 90%, 92%, 94%, 96%, 98%, 99%, 99.5%, or 100% identical to SEQ ID NO:9.

phaC and PhaC

A nucleic acid segment may comprise a nucleic acid sequence encoding a polyhydroxyalkanoate synthase protein, wherein the nucleic acid sequence is selected from the group consisting of: a nucleic acid sequence at least about 80% identical to SEQ ID NO:10; a nucleic acid sequence that hybridizes under stringent conditions to SEQ ID NO:10 or the complement thereof; a nucleic acid sequence encoding a protein at least about 80% identical to SEQ ID NO:11; and a nucleic acid sequence encoding a protein that is immunoreactive with an antibody prepared using SEQ ID NO:11 as an antigen, the antibody being immunoreactive with SEQ ID NO:11. More preferably, the nucleic acid sequence is at least about 82%, 84%, 86%, 88%, 90%, 92%, 94%, 96%, 98%, 99%, 99.5%, or 100% identical to SEQ ID NO:10. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:11.

An isolated polyhydroxyalkanoate synthase protein may comprise an amino acid sequence selected from the group consisting of: an amino acid sequence at least about 80% identical to SEQ ID NO:11; and an amino acid sequence that is immunoreactive with an antibody prepared using SEQ ID NO:11 as an antigen, the antibody being immunoreactive with SEQ ID NO:11. The protein is preferably at least about 82%, 84%, 86%, 88%, 90%, 92%, 94%, 96%, 98%, 99%, 99.5%, or 100% identical to SEQ ID NO:11.

A recombinant vector may comprise in the 5' to 3' direction: a) a promoter that directs transcription of a structural nucleic acid sequence encoding a polyhydroxyalkanoate synthase protein; b) a structural nucleic acid sequence encoding a polyhydroxyalkanoate synthase protein; wherein the structural nucleic acid sequence is selected from the group consisting of: a nucleic acid sequence at least about 80% identical to SEQ ID NO:10; a nucleic acid sequence that hybridizes under stringent conditions to SEQ ID NO:10 or the complement thereof; a nucleic acid sequence encoding a protein at least about 80% identical to SEQ ID NO:11; and a nucleic acid sequence encoding a protein that is immunoreactive with an antibody prepared using SEQ ID NO:11 as an antigen, the antibody being immunoreactive with SEQ ID NO:11; and c) a 3' transcription terminator. More preferably, the nucleic acid sequence is at least about 82%, 84%, 86%, 88%, 90%, 92%, 94%, 96%, 98%, 99%, 99.5%, or 100% identical to SEQ ID NO:10. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:11. The promoter may generally be any promoter, and more preferably is a tissue selective or tissue specific promoter. The promoter may be constitutive or inducible. The promoter may be a viral promoter. The promoter may be a CMV35S, enhanced CMV35 S, an FMV35 S, a Lesquerella hydroxylase, or a 7S conglycinin promoter.

A recombinant host cell may comprise a nucleic acid segment encoding a polyhydroxyalkanoate synthase protein, wherein the nucleic acid segment is selected from the group consisting of: a nucleic acid sequence at least about 80% identical to SEQ ID NO:10; a nucleic acid sequence that hybridizes under stringent conditions to SEQ ID NO:10 or the complement thereof; a nucleic acid sequence encoding a protein at least about 80% identical to SEQ ID NO:11; and a nucleic acid sequence encoding a protein that is immunoreactive with an antibody prepared using SEQ ID NO:11 as an antigen, the antibody being immunoreactive with SEQ ID NO:11. More preferably, the nucleic acid sequence is at least about 82%, 84%, 86%, 88%, 90%, 92%, 94%, 96%, 98%, 99%, 99.5%, or 100% identical to SEQ ID NO:10. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:11. The host cell may generally be any host cell, and preferably is a bacterial, fungal, mammalian, or plant cell. The bacterial cell is preferably an *Escherichia coli*, Bacillus, Pseudomonas, or *Ralstonia eutropha* cell. The fungal cell is preferably a *Saccharomyces cerevisiae* or *Schizosaccharomyces pombe* cell. The plant cell is preferably a tobacco, wheat, potato, Arabidopsis, and high oil seed plants such as corn, soybean, canola, oil seed rape, sugarbeet, sunflower, flax, peanut, sugarcane, switchgrass, or alfalfa cell.

A genetically transformed plant cell may comprise in the 5' to 3' direction: a) a promoter that directs transcription of a structural nucleic acid sequence encoding a polyhydroxyalkanoate synthase protein; b) a structural nucleic acid sequence encoding a polyhydroxyalkanoate synthase protein; wherein the structural nucleic acid sequence is selected from the group consisting of: a nucleic acid sequence at least about 80% identical to SEQ ID NO:10; a nucleic acid sequence that hybridizes under stringent conditions to SEQ ID NO:10 or the complement thereof, a nucleic acid sequence encoding a protein at least about 80% identical to SEQ ID NO:11; and a nucleic acid sequence encoding a protein that is immunoreactive with an antibody prepared using SEQ ID NO:11 as an antigen, the antibody being immunoreactive with SEQ ID NO:11; c) a 3' transcription terminator; and d) a 3' polyadenylation signal sequence that directs the addition of polyadenylate nucleotides to the 3' end of RNA transcribed from the structural nucleic acid sequence. More preferably, the nucleic acid sequence is at least about 82%, 84%, 86%, 88%, 90%, 92%, 94%, 96%, 98%, 99%, 99.5%, or 100% identical to SEQ ID NO:10. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:11. The plant may generally be any plant, and more preferably a monocot, dicot, or conifer. The plant is preferably a tobacco, wheat, potato, Arabidopsis, and high oil seed plants such as corn, soybean, canola, oil seed rape, sugarbeet, sunflower, flax, peanut, sugarcane, switchgrass, or alfalfa plant.

A method of preparing host cells useful to produce a polyhydroxyalkanoate synthase protein may comprise a) selecting a host cell; b) transforming the selected host cell with a recombinant vector having a structural nucleic acid sequence encoding a polyhydroxyalkanoate synthase protein, wherein the structural nucleic acid sequence is selected from the group consisting of: a nucleic acid sequence at least about 80% identical to SEQ ID NO:10; a nucleic acid sequence that hybridizes under stringent conditions to SEQ ID NO:10 or the complement thereof; a nucleic acid sequence encoding a protein at least about 80% identical to SEQ ID NO:11; and a nucleic acid sequence encoding a protein that is immunoreactive with an antibody prepared using SEQ ID NO:11 as an antigen, the antibody being immunoreactive with SEQ ID NO:11; and c) obtaining transformed host cells. More preferably, the nucleic acid sequence is at least about 82%, 84%, 86%, 88%, 90%, 92%, 94%, 96%, 98%, 99%, 99.5%, or 100% identical to SEQ ID NO:10. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:11. The host cell may generally be any host cell, and preferably is a bacterial, fungal, mammalian, or plant cell. The bacterial cell is preferably an *Escherichia coli*, Bacillus, Pseudomonas, or *Ralstonia eutropha* cell. The fungal cell is preferably a *Saccharomyces cerevisiae* or *Schizosaccharomyces pombe* cell. The plant cell is preferably a tobacco, wheat, potato, Arabidopsis, and high oil seed plants such as corn, soybean, canola, oil seed rape, sugarbeet, sunflower, flax, peanut, sugarcane, switchgrass, or alfalfa cell.

A method of preparing plants useful to produce a polyhydroxyalkanoate synthase protein may comprise a) selecting a host plant cell; b) transforming the selected host plant cell with a recombinant vector having a structural nucleic acid sequence encoding a polyhydroxyalkanoate synthase protein, wherein the structural nucleic acid sequence is selected from the group consisting of: a nucleic acid sequence at least about 80% identical to SEQ ID NO:10; a nucleic acid sequence that hybridizes under stringent conditions to SEQ ID NO:10 or the complement thereof; a nucleic acid sequence encoding a protein at least about 80% identical to SEQ ID NO:11; and a nucleic acid sequence encoding a protein that is immunoreactive with an antibody prepared using SEQ ID NO:11 as an antigen, the antibody being immunoreactive with SEQ ID NO:11; c) obtaining transformed host plant cells; and d) regenerating the transformed host plant cells. More preferably, the nucleic acid sequence is at least about 82%, 84%, 86%, 88%, 90%, 92%, 94%, 96%, 98%, 99%, 99.5%, or 100% identical to SEQ ID NO:10. The nucleic acid segment may be obtained from a natural source, may be mutagenized, may be genetically engineered by mutagenesis or other methods, or may be synthetic. The nucleic acid sequence preferably encodes a protein at least about 82%, 84%, 86%, 88%, 90%, 92%, 94%, 96%, 98%, 99%, 99.5%, or 100% identical to SEQ ID NO:11. The plant (and plant cell) may generally be any plant, and more preferably a monocot, dicot, or conifer. The plant is preferably a tobacco, wheat, potato, Arabidopsis, and high oil seed plants such as corn, soybean, canola, oil seed rape, sugarbeet, sunflower, flax, peanut, sugarcane, switchgrass, or alfalfa plant.

The invention also relates to fusion proteins. A fusion protein may comprise a green fluorescent protein subunit; and a polyhydroxyalkanoate synthase protein subunit; wherein the polyhydroxyalkanoate synthase protein subunit comprises an amino acid sequence selected from the group consisting of: an amino acid sequence at least about 80% identical to SEQ ID NO:11; and an amino acid sequence that is immunoreactive with an antibody prepared using SEQ ID NO:11 as an antigen, the antibody being immunoreactive with SEQ ID NO:11. The polyhydroxyalkanoate synthase protein subunit is preferably at least about 82%, 84%, 86%, 88%, 90%, 92%, 94%, 96%, 98%, 99%, 99.5%, or 100% identical to SEQ ID NO:11.

A nucleic acid segment encoding a fusion protein may comprise a nucleic acid sequence encoding a green fluorescent protein subunit; and a nucleic acid sequence encoding a polyhydroxyalkanoate synthase protein subunit; wherein the nucleic acid sequence encoding a polyhydroxyalkanoate synthase protein subunit is selected from the group consisting of: a nucleic acid sequence at least about 80% identical to SEQ ID NO:10; a nucleic acid sequence that hybridizes under stringent conditions to SEQ ID NO:10 or the complement thereof; a nucleic acid sequence encoding a protein at least about 80% identical to SEQ ID NO:11; and a nucleic acid sequence encoding a protein that is immunoreactive with an antibody prepared using SEQ ID NO:11 as an antigen, the antibody being immunoreactive with SEQ ID NO:11. More preferably, the nucleic acid sequence is at least about 82%, 84%, 86%, 88%, 90%, 92%, 94%, 96%, 98%, 99%, 99.5%, or 100% identical to SEQ ID NO:10. The nucleic acid sequence may be obtained from a natural source, may be mutagenized, may be genetically engineered by mutagenesis or other methods, or may be synthetic. The nucleic acid sequence preferably encodes a protein subunit at least about 82%, 84%, 86%, 88%, 90%, 92%, 94%, 96%, 98%, 99%, 99.5%, or 100% identical to SEQ ID NO:11.

PHA biosynthesis methods: phaB and phaC

A method for the preparation of polyhydroxyalkanoate may comprise: a) obtaining a cell comprising: a nucleic acid sequence encoding a 3-keto-acyl-CoA reductase protein; and a nucleic acid sequence encoding a PHA synthase protein; wherein: the nucleic acid sequence encoding a 3-keto-acyl-CoA reductase protein is not naturally found in the cell; the nucleic acid sequence encoding a PHA synthase protein is not naturally found in the cell; the nucleic acid sequence encoding a 3-keto-acyl-CoA reductase protein is selected from the group consisting of: a nucleic acid sequence at least about 80% identical to SEQ ID NO:8; a nucleic acid sequence that hybridizes under stringent conditions to SEQ ID NO:8 or the complement thereof; a nucleic acid sequence encoding a protein at least about 80% identical to SEQ ID NO:9; and a nucleic acid sequence encoding a protein that is immunoreactive with an antibody prepared using SEQ ID NO:9 as an antigen, the antibody being immunoreactive with SEQ ID NO:9; and the nucleic acid sequence encoding a PHA synthase protein is selected from the group consisting of: a nucleic acid sequence at least about 80% identical to SEQ ID NO:10; a nucleic acid sequence that hybridizes under stringent conditions to SEQ ID NO:10 or the complement thereof; a nucleic acid sequence encoding a protein at least about 80% identical to SEQ ID NO:11; and a nucleic acid sequence encoding a protein that is immunoreactive with an antibody prepared using SEQ ID NO:11 as an antigen, the antibody being immunoreactive with SEQ ID NO:11; and b) culturing the cell under conditions suitable for the preparation of polyhydroxyalkanoate. The nucleic acid sequence encoding a 3-keto-acyl-CoA reductase protein more preferably is at least about 82%, 84%, 86%, 88%, 90%, 92%, 94%, 96%, 98%, 99%, 99.5%, or 100% identical to SEQ ID NO:8. The nucleic acid sequence encoding a 3-keto-acyl-CoA reductase protein may be obtained from a natural source, may be mutagenized, may be genetically engineered by mutagenesis or other methods, or may be synthetic. The nucleic acid sequence encoding a 3-keto-acyl-CoA reductase protein preferably encodes a protein at least about 82%, 84%, 86%, 88%, 90%, 92%, 94%, 96%, 98%, 99%, 99.5%, or 100% identical to SEQ ID NO:9. The nucleic acid sequence encoding a PHA synthase protein more preferably is at least about 82%, 84%, 86%, 88%, 90%, 92%, 94%, 96%, 98%, 99%, 99.5%, or 100% identical to SEQ ID NO:10. The nucleic acid sequence encoding a PHA synthase protein may be obtained from a natural source, may be mutagenized, may be genetically engineered by mutagenesis or other methods, or may be synthetic. The nucleic acid sequence encoding a PHA synthase protein preferably encodes a protein at least about 82%, 84%, 86%, 88%, 90%, 92%, 94%, 96%, 98%, 99%, 99.5%, or 100% identical to SEQ ID NO:11. The cell may generally be any cell, and preferably is a bacterial, fungal, mammalian, or plant cell. The bacterial cell is preferably an *Escherichia coli*, Bacillus, Pseudomonas, or *Ralstonia eutropha* cell. The fungal cell is preferably a *Saccharomyces cerevisiae* or *Schizosaccharomyces pombe* cell. The plant cell is preferably a tobacco, wheat, potato, Arabidopsis, and high oil seed plants such as corn, soybean, canola, oil seed rape, sugarbeet, sunflower, flax, peanut, sugarcane, switchgrass, or alfalfa cell. The polyhydroxyalkanoate may be a homopolymer or copolymer. The polyhydroxyalkanoate may be a polyhydroxybutyrate, polyhydroxyvalerate, polyhydroxyhexanoate, polyhydroxyoctanoate, polyhydroxydecanoate, or copolymers thereof.

A method for the preparation of polyhydroxyalkanoate may comprise: a) obtaining a plant comprising: a nucleic acid sequence encoding a 3-keto-acyl-CoA reductase protein; and a nucleic acid sequence encoding a PHA synthase protein; wherein: the nucleic acid sequence encoding a 3-keto-acyl-CoA reductase protein is not naturally found in the plant; the nucleic acid sequence encoding a PHA synthase protein is not naturally found in the plant; the nucleic acid sequence encoding a 3-keto-acyl-CoA reductase protein is selected from the group consisting of: a nucleic acid sequence at least about 80% identical to SEQ ID NO:8; a nucleic acid sequence that hybridizes under stringent conditions to SEQ ID NO:8 or the complement thereof; a nucleic acid sequence encoding a protein at least about 80% identical to SEQ ID NO:9; and a nucleic acid sequence encoding a protein that is immunoreactive with an antibody prepared using SEQ ID NO:9 as an antigen, the antibody being immunoreactive with SEQ ID NO:9; and the nucleic acid sequence encoding a PHA synthase protein is selected from the group consisting of: a nucleic acid sequence at least about 80% identical to SEQ ID NO:10; a nucleic acid sequence that hybridizes under stringent conditions to SEQ ID NO:10 or the complement thereof; a nucleic acid sequence encoding a protein at least about 80% identical to SEQ ID NO:11; and a nucleic acid sequence encoding a protein that is immunoreactive with an antibody prepared using SEQ ID NO:11 as an antigen, the antibody being immunoreactive with SEQ ID NO:11; and b) growing the plant under conditions suitable for the preparation of polyhydroxyalkanoate. The nucleic acid sequence encoding a 3-keto-acyl-CoA reductase protein more preferably is at least about 82%, 84%, 86%, 88%, 90%, 92%, 94%, 96%, 98%, 99%, 99.5%, or 100% identical to SEQ ID NO:8. The nucleic acid sequence encoding a 3-keto-acyl-CoA reductase protein may be obtained from a natural source, may be mutagenized, may be genetically engineered by mutagenesis or other methods, or may be synthetic. The nucleic acid sequence encoding a 3-keto-acyl-CoA reductase protein preferably encodes a protein at least about 82%, 84%, 86%, 88%, 90%, 92%, 94%, 96%, 98%, 99%, 99.5%, or 100% identical to SEQ ID NO:9. The nucleic acid sequence encoding a PHA synthase protein more preferably is at least about 82%, 84%, 86%, 88%, 90%, 92%, 94%, 96%, 98%, 99%, 99.5%, or 100% identical to SEQ ID NO:10. The nucleic acid sequence encoding a PHA synthase protein may be obtained from a natural source, may be mutagenized, may be genetically engineered by mutagenesis or other methods, or may be synthetic. The nucleic acid sequence encoding a PHA synthase protein preferably encodes a protein at least about 82%, 84%, 86%, 88%, 90%, 92%, 94%, 96%, 98%, 99%, 99.5%, or 100% identical to SEQ ID NO:11. The plant is preferably a tobacco, wheat, potato, Arabidopsis, and high oil seed plants such as corn, soybean, canola, oil seed rape, sugarbeet, sunflower, flax, peanut, sugarcane, switchgrass, or alfalfa plant. The polyhydroxyalkanoate may be a homopolymer or copolymer. The polyhydroxyalkanoate may be a polyhydroxybutyrate, polyhydroxyvalerate, polyhydroxyhexanoate, polyhydroxyoctanoate, polyhydroxydecanoate, or copolymers thereof.

PHA Biosynthesis Methods: phaB

A method for the preparation of polyhydroxyalkanoate may comprise: a) obtaining a cell comprising: a nucleic acid sequence encoding a 3-keto-acyl-CoA reductase protein; and a nucleic acid sequence encoding a PHA synthase protein; wherein: the nucleic acid sequence encoding a 3-keto-acyl-CoA reductase protein is not naturally found in the cell; the nucleic acid sequence encoding a 3-keto-acyl-CoA reductase protein is selected from the group consisting of: a nucleic acid sequence at least about 80% identical to SEQ ID NO:8; a nucleic acid sequence that hybridizes under stringent conditions to SEQ ID NO:8 or the complement thereof; a nucleic acid sequence encoding a protein at least about 80% identical to SEQ ID NO:9; and a nucleic acid sequence encoding a protein that is immunoreactive with an antibody prepared using SEQ ID NO:9 as an antigen, the antibody being immunoreactive with SEQ ID NO:9; and b) culturing the cell under conditions suitable for the preparation of polyhydroxyalkanoate. The nucleic acid sequence encoding a 3-keto-acyl-CoA reductase protein more preferably is at least about 82%, 84%, 86%, 88%, 90%, 92%, 94%, 96%, 98%, 99%, 99.5%, or 100% identical to SEQ ID NO:8. The nucleic acid sequence encoding a 3-keto-acyl-CoA reductase protein may be obtained from a natural source, may be mutagenized, may be genetically engineered by mutagenesis or other methods, or may be synthetic. The nucleic acid sequence encoding a 3-keto-acyl-CoA reductase protein preferably encodes a protein at least about 82%, 84%, 86%, 88%, 90%, 92%, 94%, 96%, 98%, 99%, 99.5%, or 100% identical to SEQ ID NO:9. The cell may generally be any cell, and preferably is a bacterial, fungal, mammalian, or plant cell. The bacterial cell is preferably an *Escherichia coli*, Bacillus, Pseudomonas, or *Ralstonia eutropha* cell. The fungal cell is preferably a *Saccharomyces cerevisiae* or *Schizosaccharomyces pombe* cell. The plant cell is preferably a tobacco, wheat, potato, Arabidopsis, and high oil seed plants such as corn, soybean, canola, oil seed rape, sugarbeet, sunflower, flax, peanut, sugarcane, switchgrass, or alfalfa cell. The polyhydroxyalkanoate may be a homopolymer or copolymer. The polyhydroxyalkanoate may be a polyhydroxybutyrate, polyhydroxyvalerate, polyhydroxyhexanoate, polyhydroxyoctanoate, polyhydroxydecanoate, or copolymers thereof.

A method for the preparation of polyhydroxyalkanoate may comprise: a) obtaining a plant comprising: a nucleic acid sequence encoding a 3-keto-acyl-CoA reductase protein; and a nucleic acid sequence encoding a PHA synthase protein; wherein: the nucleic acid sequence encoding a 3-keto-acyl-CoA reductase protein is not naturally found in the plant; the nucleic acid sequence encoding a 3-keto-acyl-CoA reductase protein is selected from the group consisting of: a nucleic acid sequence at least about 80% identical to SEQ ID NO:8; a nucleic acid sequence that hybridizes under stringent conditions to SEQ ID NO:8 or the complement thereof; a nucleic acid sequence encoding a protein at least about 80% identical to SEQ ID NO:9; and a nucleic acid sequence encoding a protein that is immunoreactive with an antibody prepared using SEQ ID NO:9 as an antigen, the antibody being immunoreactive with SEQ ID NO:9; and b) growing the plant under conditions suitable for the preparation of polyhydroxyalkanoate. The nucleic acid sequence encoding a 3-keto-acyl-CoA reductase protein more preferably is at least about 82%, 84%, 86%, 88%, 90%, 92%, 94%, 96%, 98%, 99%, 99.5%, or 100% identical to SEQ ID NO:8. The nucleic acid sequence encoding a 3-keto-acyl-CoA reductase protein may be obtained from a natural source, may be mutagenized, may be genetically engineered by mutagenesis or other methods, or may be synthetic. The nucleic acid sequence encoding a 3-keto-acyl-CoA reductase protein preferably encodes a protein at least about 82%, 84%, 86%, 88%, 90%, 92%, 94%, 96%, 98%, 99%, 99.5%, or 100% identical to SEQ ID NO:9. The plant may generally be any plant, and preferably is a tobacco, wheat, potato, Arabidopsis, high oil seed plants such as corn, soybean, canola, oil seed rape, sugarbeet, sunflower, flax, peanut, sugarcane, switchgrass, or alfalfa plant. The polyhydroxyalkanoate may be a homopolymer or copolymer. The polyhydroxyalkanoate may be a polyhydroxybutyrate, polyhydroxyvalerate, polyhydroxyhexanoate, polyhydroxyoctanoate, polyhydroxydecanoate, or copolymers thereof.

PHA Biosynthesis Methods: phaC

A method for the preparation of polyhydroxyalkanoate may comprise: a) obtaining a cell comprising: a nucleic acid sequence encoding a 3-keto-acyl-CoA reductase protein; and a nucleic acid sequence encoding a PHA synthase protein; wherein: the nucleic acid sequence encoding a PHA synthase protein is not naturally found in the cell; the nucleic acid sequence encoding a PHA synthase protein is selected from the group consisting of: a nucleic acid sequence at least about 80% identical to SEQ ID NO:10; a nucleic acid sequence that hybridizes under stringent conditions to SEQ ID NO:10 or the complement thereof; a nucleic acid sequence encoding a protein at least about 80% identical to SEQ ID NO:11; and a nucleic acid sequence encoding a protein that is immunoreactive with an antibody prepared using SEQ ID NO:11 as an antigen, the antibody being immunoreactive with SEQ ID NO:11; and b) culturing the cell under conditions suitable for the preparation of polyhydroxyalkanoate. The nucleic acid sequence encoding a PHA synthase protein more preferably is at least about 82%, 84%, 86%, 88%, 90%, 92%, 94%, 96%, 98%, 99%, 99.5%, or 100% identical to SEQ ID NO:10. The nucleic acid sequence encoding a PHA synthase protein may be obtained from a natural source, may be mutagenized, may be genetically engineered by mutagenesis or other methods, or may be synthetic. The nucleic acid sequence encoding a PHA synthase protein preferably encodes a protein at least about 82%, 84%, 86%, 88%, 90%, 92%, 94%, 96%, 98%, 99%, 99.5%, or 100% identical to SEQ ID NO:11. The cell may generally be any cell, and preferably is a bacterial, fungal, mammalian, or plant cell. The bacterial cell is preferably an *Escherichia coli*, Bacillus, Pseudomonas, or *Ralstonia eutropha* cell. The fungal cell is preferably a *Saccharomyces cerevisiae* or *Schizosaccharomyces pombe* cell. The plant cell is preferably a tobacco, wheat, potato, Arabidopsis, and high oil seed plants such as corn, soybean, canola, oil seed rape, sugarbeet, sunflower, flax, peanut, sugarcane, switchgrass, or alfalfa cell. The polyhydroxyalkanoate may be a homopolymer or copolymer. The polyhydroxyalkanoate may be a polyhydroxybutyrate, polyhydroxyvalerate, polyhydroxyhexanoate, polyhydroxyoctanoate, polyhydroxydecanoate, or copolymers thereof.

A method for the preparation of polyhydroxyalkanoate may comprise: a) obtaining a plant comprising: a nucleic acid sequence encoding a 3-keto-acyl-CoA reductase protein; and a nucleic acid sequence encoding a PHA synthase protein; wherein: the nucleic acid sequence encoding a PHA synthase protein is not naturally found in the plant; the nucleic acid sequence encoding a PHA synthase protein is selected from the group consisting of: a nucleic acid sequence at least about 80% identical to SEQ ID NO:10; a nucleic acid sequence that hybridizes under stringent conditions to SEQ ID NO:10 or the complement thereof; a nucleic acid sequence encoding a protein at least about 80% identical to SEQ ID NO:11; and a nucleic acid sequence encoding a protein that is immunoreactive with an antibody prepared using SEQ ID NO:11 as an antigen, the antibody being immunoreactive with SEQ ID NO:11; and b) growing the plant under conditions suitable for the preparation of polyhydroxyalkanoate. The nucleic acid sequence encoding a PHA synthase protein more preferably is at least about 82%, 84%, 86%, 88%, 90%, 92%, 94%, 96%, 98%, 99%, 99.5%, or 100% identical to SEQ ID NO:10. The nucleic acid sequence encoding a PHA synthase protein may be obtained from a natural source, may be mutagenized, may be genetically engineered by mutagenesis or other methods, or may be synthetic. The nucleic acid sequence encoding a PHA synthase protein preferably encodes a protein at least about 82%, 84%, 86%, 88%, 90%, 92%, 94%, 96%, 98%, 99%, 99.5%, or 100% identical to SEQ ID NO:11. The plant may generally be any plant, and preferably is a tobacco, wheat, potato, Arabidopsis, high oil seed plants such as corn, soybean, canola, oil seed rape, sugarbeet, sunflower, flax, peanut, sugarcane, switchgrass, or alfalfa plant. The polyhydroxyalkanoate may be a homopolymer or copolymer. The polyhydroxyalkanoate may be a polyhydroxybutyrate, polyhydroxyvalerate, polyhydroxyhexanoate, polyhydroxyoctanoate, polyhydroxydecanoate, or copolymers thereof.

Methods for Preparing Higher Polyhydroxyalkanoates

Polyhydroxyalkanoate may be prepared by a method comprising: a) obtaining a recombinant host cell comprising: a nucleic acid sequence encoding a β-ketothiolase protein; a nucleic acid sequence encoding a 3-ketoacyl-CoA reductase protein; a nucleic acid sequence encoding a polyhydroxyalkanoate synthase protein; a nucleic acid sequence encoding a β-hydroxyacyl-CoA dehydrase; and a nucleic acid sequence encoding an acyl-CoA dehydrogenase protein or an enoyl-CoA reductase protein; and b) culturing the recombinant host cell under conditions suitable for the preparation of polyhydroxyalkanoate; wherein: the polyhydroxyalkanoate comprises C6, C8, or C10 monomer subunits; the nucleic acid sequence encoding a 3-keto-acyl-CoA reductase protein is selected from the group consisting of: a nucleic acid sequence at least about 80% identical to SEQ ID NO:8; a nucleic acid sequence that hybridizes under stringent conditions to SEQ ID NO:8 or the complement thereof; a nucleic acid sequence encoding a protein at least about 80% identical to SEQ ID NO:9; and a nucleic acid sequence encoding a protein that is immunoreactive with an antibody prepared using SEQ ID NO:9 as an antigen, the antibody being immunoreactive with SEQ ID NO:9.

Primers, Probes, and Antibodies

The sequences disclosed in the sequence listing may also be used to prepare primers, probes, and monoclonal or polyclonal antibodies.

SEQ ID NOS:1, 2, 4, 6, 8, 10, 22, 24, 26, and 28, and the their complementary strands may be used to design oligonucleotide primers and probes. Primers and probes are typically at least 15 nucleotides in length, and more preferably are at least 20, 22, 24, 26, 28, 30, 40, or 50 nucleotides in length. Contiguous nucleotide sequences from a given sequence are chosen based upon favorable hybridization conditions, including minimization of hairpin or other detrimental sequences. The identification of suitable primer or probe sequences is well known to those of skill in the art, and is facilitated by commercially available software such as MacVector (Oxford Molecular Group) and Xprimer (http://alces.med.umn.edu/rawprimer.html). Primers and probes may be used for the screening of libraries, for PCR amplification, and other routine molecular biological applications. Primers and probes may also be used for antisense applications.

SEQ ID NOS:3, 5, 7, 9, 11, 23, 25, 27, and 29 may be used for the generation of monoclonal or polyclonal antibodies. The entire sequences may be used, or antigenic fragments thereof. Alternatively, portions of the full length sequences may be synthesized and covalently attached to antigenic proteins such as keyhole limpet hemocyanin (KLH). Portions of the full length sequences may be used for the preparation of multi-antigenic peptides (52). The generation of monoclonal and polyclonal antibodies is well known to those of skill in the art.

The following Examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Bacterial Strains and Plasmids

TABLE 1

Strains

| Strains | Relevant characteristics[a] | Source or Reference |
|---|---|---|
| E. coli DH5α | deoR endA1 gyrA96 hsdR17 ($r_k^-m_k^+$) recA1 relA1 supE44 thi-1 AE(lacZYA-argFV169) φ80lacZAEM15 F⁻λ⁻. Cloning host and for expression of pha genes | Clontech |
| B. megaterium 11561 | Wild type, used to clone pha genes | ATCC[b] |

TABLE 1-continued

Strains

| Strains | Relevant characteristics[a] | Source or Reference |
|---|---|---|
| B. megaterium PHA05 | phaP, –Q, –R, –B and –C deletion derivative of B. megaterium 11561 | This Application |
| P. oleovorans 29347 | PHA positive control | ATCC |
| P. putida GPp104 | PHA negative mutant obtained by chemical mutagenesis | (22) |

TABLE 2

Plasmids

| Plasmids | Relevant characteristics[a] | Source or Reference |
|---|---|---|
| pBluescriptIISK | Cloning vector, ColEl oriV[c], Amp[r] | Stratagene |
| pGFPuv | Source of gfp gene, ColEl oriV, Amp[r] | Clontech |
| pHPS9 | Bacillus-Escherichia coli shuttle vector, ColEl and pTA1060 oriV, Em[r], Cm[r] | (16) |
| pSUP104 | Pseudomonas-Escherichia coli shuttle vector, Q-type and mini15 oriV, Em[r], Tc[r] | (40) |
| pGM1 | EcoRI in phaP to HindIII in phaC, cloned into the EcoRI-HindIII sites of pBluescriptIISK, Amp[r] | This application |
| pGM6 | PstI in phaB to EcoRI in ykrM, cloned into the PstI-EcoRI sites of pBluescriptIISK, Amp[r] | This application |
| pGM7 | EcoRI in phaP to EcoRI in ykrM, cloned into the EcoRI site of pBluescriptIISK, Amp[r] | This application |
| pGM9 | HindIII upstream of ykoY to PstI in phaB, cloned into the HindIII -PstI sites of pBluescriptIISK, Amp[r] | This application |
| pGM10 | HindIII upstream of ykoY to EcoRI in ykrM, cloned into the HindIII -EcoRI sites of pBluescriptIISK, Amp[r] | This application |
| pGM7H | EcoRI in phaP to EcoRI in ykrM, cloned into the EcoRI site of pHPS9, Cm[r] | This application |
| pC/GFP2 | PhaC::GFP out-of-frame fusion plasmid. Fragment shown in FIG. 4A cloned in pBluescriptIISK, Amp[r] | This application |
| pC/GFP3 | PhaC::GFP in-frame fusion plasmid. | This |
| pGM13 | PhaC::GFP in-frame fusion plasmid. Fragment shown in FIG. 4C cloned in pHPS9, Em[r]Lm[r] | This application |
| pGM13C | GFP localization control plasmid. Part of phaB and phaC deleted. Fragment shown in FIG. 4D cloned in pHPS9, Em[r]Lm[r] | This application |
| pP/GFP3 | PhaP::GFP in-frame fusion plasmid. Fragment shown in FIG. 4E cloned in pBluescriptIISK, Amp[r] | This application |
| pGM16.2 | PhaP::GFP in-frame fusion plasmid. Fragment shown in FIG. 4F cloned in pHPS9, Em[r]Lm[r] | This application |
| pGM107 | EcoRI in phaP to EcoRI in ykrM, cloned as a BamHI-SalI fragment from pGM7, into the BamHI and SalI sites of pSUP104, Cm[r] | This application |
| pDR1 | PstI in phaB to EcoRI in ykrM, cloned as a SmaI-EcoRV fragment from pGM6 into the two DraI sites of pSUP104 in same orientation as the Cm gene, with phaC expressed from the Cm promoter, Tc[r] | This application |
| pGM61 | Derived from pGM13. It carries an in-frame 594 bp deletion in phaR, extending from 96 bp upstream of the phaR initiation codon through codon 144. | This Application |
| pGM73 | Derived from pGM61. Carries a transcriptional fusion between the promoter of phaP and the coding region plus translation signals of phaR. A 663 bp DNA fragment harboring phaR was cloned into the SnaBI site in phaP in the sense orientation. | This Application |

[a]Em[r], erythromycin resistant; Lm[r], lincomycin resistant; Cm[r], chloramphenicol resistant; Amp[r], ampicillin resistant; Tc[r], Tetracycline resistant. [b]ATCC, American Type Culture Collection. [c]Origin of replication.

Example 2

Media and Growth Conditions

Cultures were grown at 37° C. (unless otherwise stated) in liquid media, aerated by rotation at 250 rpm in either Luria-Bertani (LB) broth (33) or M9 Minimal Salts (Life Technologies, Bethesda, Md.) with 1% (w/v) glucose. For growth on plates, the above media with 1.5% agar (Sigma, A4550) was used. For plasmid selections, the appropriate antibiotics were included in the media: ampicillin (200 $\mu$g/mL [AMP$^{200}$]), chloramphenicol (25 $\mu$g/mL [CM$^{25}$]), erythromycin (200 $\mu$g/mL [EM$^{200}$]), or tetracycline (12.5 $\mu$g/mL [TC$^{125}$]) for plasmid selection in Escherichia coli; chloramphenicol (12 $\mu$g/mL [CM$^{12}$]), or erythromycin (1 $\mu$g/mL [EM$^{1}$]) plus lincomycin (25 $\mu$g/mL [LM$^{25}$]) for plasmid selection in Bacillus megaterium; chloramphenicol (160 $\mu$g/mL [CM$^{160}$]), or tetracycline (30 $\mu$g/mL [TC$^{30}$]) for selection in Pseudomonas.

Example 3

Transformations

Escherichia coli and Pseudomonas putida were transformed by electroporation of competent cells using an electroporator (Eppendorf) and following the manufacturers instructions. *Bacillus megaterium* was transformed using a biolistic transformation procedure (39).

Example 4

Microscopy

For phase contrast microscopy, wet mounts of cultures were visualized at ×1,000 magnification in a light microscope with phase contrast attachments (Labophot-2 Microscope, Nikon, Inc.). To view PHA inclusion-bodies, samples were heat fixed, stained with 1% (w/v) Nile Blue A (Sigma) for 15 minutes at 55° C., destained for 30 seconds in 8% (v/v) acetic acid, water washed, air dried, and viewed at ×1000 magnification under fluorescence using filters; excitation, 446/10 nm; barrier filter, 590 nm; dichroic mirror, 580 nm. To view GFP, wet mounts of cultures with or without 1% (w/v) agarose were viewed at ×1000 magnification under fluorescence using filters; excitation, 390–450 nm; barrier filter, 480–520 nm; dichroic mirror, 470 nm.

Example 5

Codon Usage in *Bacillus megaterium*

*Bacillus megaterium* uses three codons as start codons in protein coding sequences. ATG, TTG, and GTG all encode methionine when present at the start of a coding region. TTG and GTG encode leucine and valine when present within a coding region, respectively. *Bacillus megaterium* uses TGA, TAA, and TAG as stop codons.

*Bacillus megaterium* sequences starting with TTG or GTG may require mutagenesis to ATG if the sequences are to be expressed in organisms that use ATG exclusively as a start codon.

Example 6

Separation of Polypeptides Associated with PHA Inclusion-Bodies.

Figure 1:
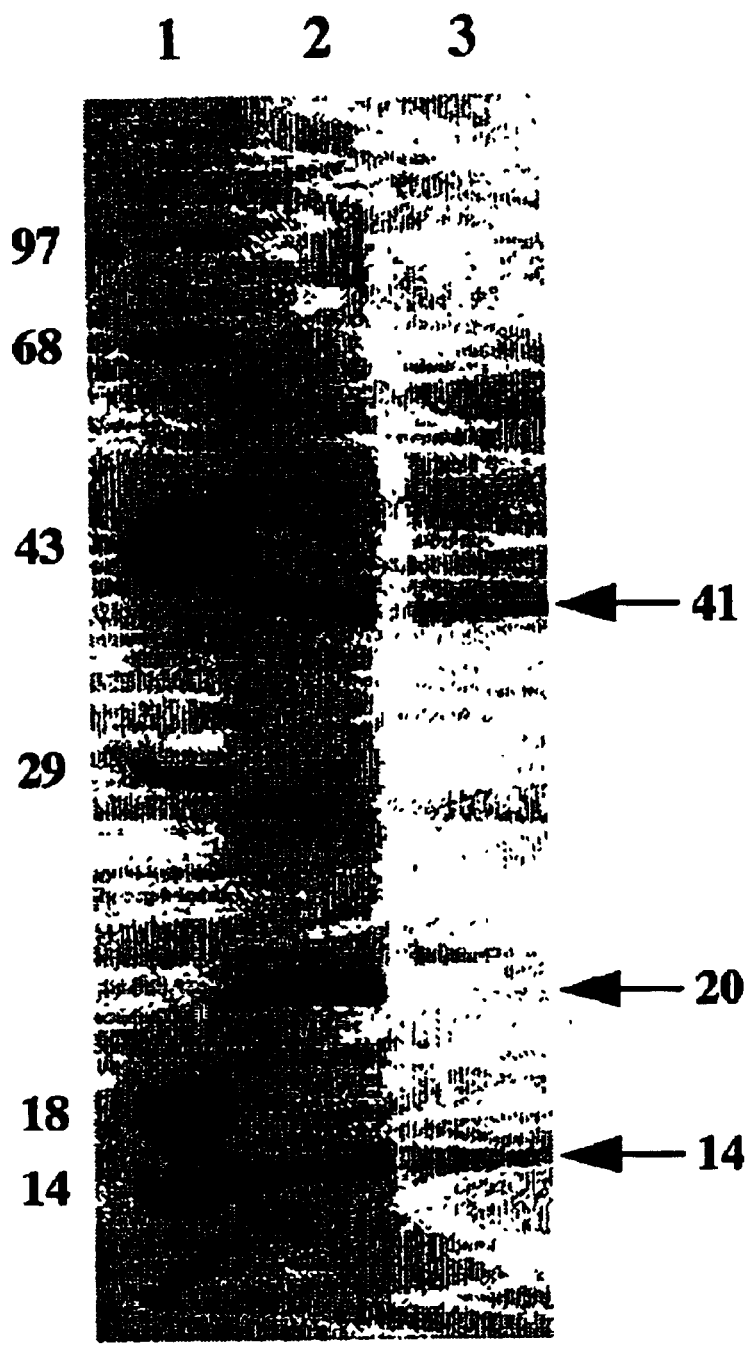
FIG. 1. PHA inclusion-body associated proteins. SDS-polyacrylamide gel electrophoresis of proteins released from purified PHA inclusion-bodies. Lane 1, molecular weight markers in kDa, 14, 18, 29, 43, 68 and 97. Lane 2, proteins from inclusion-bodies of cells harvested at late exponential growth phase. Lane 3, same as lane 2 except this part of the gel was stained following 45 minutes transfer of proteins (seen in lane 2) to PVDF membrane. The bands were visualized by staining with Coomassie Blue.

In an attempt to determine their relevance, proteins that co-purify with PHA inclusion-bodies were separated by electrophoreses on an SDS-polyacrylamide gel (FIG. 1).

Inclusion-bodies were purified (32) followed by suspension in TE buffer (10 mM Tris-HCl pH 8, 1 mM EDTA) with 2% (w/v) SDS. An equal volume of 2× sample buffer (100 mM Tris-HCI (pH 6.8), 4% SDS, 4 mM EDTA, 20% glycerol, 2% 2-mercaptoethanol, 0.1% bromophenol blue) was added prior to boiling for 5 minutes and samples were centrifuged for 3 minutes to pellet PHA; the supernatant was loaded on a 12% SDS-polyacrylamide gel and run at 8 mA overnight at 4° C. to separate proteins. The gel was stained with Coomassie Blue for 5 minutes prior to transfer of proteins to a polyvinylidene difluoride membrane using a semi-dry electroblotter at 400 mA for 45 minutes.

There were at least thirteen such proteins present in various quantities. Some or all of these proteins could be intrinsic structural components of PHA inclusion-bodies, enzymes involved with PHA metabolism or possibly scaffolding components involved in inclusion-body assembly. Alternatively, they could have been acquired by the inclusion-bodies during the purification procedure. The three most abundant proteins had molecular weights of approximately 14, 20 and 41 kDa.

The N-terminal amino acid sequence for the three most prevalent proteins were determined. Membrane carrying the proteins of interest was cut for use in N-terminal amino acid sequence determination by Edman Degradation using a minimum quantity of 200 pmols of each protein. The N-terminal amino acid sequence of the 14 kDa protein was KVFGRXELAAAMKRXGL (SEQ ID NO:19), the 20 kDa protein was NTVKYXTVIXAMXXQ (SEQ ID NO:20), and the 41 kDa proteins was AIPYVQEXEKL (SEQ ID NO:21). A BLASTp search ((1), performed with NCBI Entrez database; http://www.ncbi.nlm.nih.gov/Entrez/) revealed that the 14 kDa protein was lysozyme and the other two N-terminal sequences were novel. It was concluded that the lysozyme used in the cell lysis procedure had co-purified with the PHA inclusion bodies. This result confirms that not necessarily all of the proteins that co-purify with PHA inclusion-bodies are associated with them in vivo, as was also shown for *Chromatium vinosum* (27).

Example 7

Cloning the pha Region

Purification of genomic and plasmid DNA, Southern blot, hybridization and cloning were by standard procedures (38). To clone the DNA sequences that coded for the two most abundant proteins on purified PHA inclusion-bodies, degenerate oligonucleotide probes based on their N-terminal amino acid sequences were used. The probes were: AAY-ACRGTNAAATAYNNNACRGT-NATYNNNGCDATGATG (n2, SEQ ID NO:12) and GCDATYCCDTAYGTNCARGAAGGHTTYAAA (n5, SEQ ID NO:13) for the 20 kDa and 41 kDa proteins, respectively (FIG. 1).

Both probes, used in separate 38° C. Southern blotting hybridization experiments, identified a 6.4 kb HindIII, a 5.2 kb EcoRI, and a 3.7 kb HindIII to EcoRI DNA fragment of DNA, indicating that the 5' ends of the coding regions for both of these proteins were located less than 3.7 kb apart in the genome. The three fragments were purified from agarose following electrophoresis, and cloned into plasmid pBluescriptIISK.

Positive clones were identified by hybridization to the same degenerate probes, thus yielding plasmid pGM1 containing the 3.7 kb fragment. Sequences contiguous with and overlapping this primary cloned fragment were cloned in a similar manner except that probes based on the ends of the sequenced DNA fragment were used, and hybridization was performed at 55° C. The probes used were GCTTCAT-GCGTGCGGTTTG (bmp, SEQ ID NO:14) and GGAC-CGTTCGGAAAATCAGCGG (bmc, SEQ ID NO:15), yielding respectively, pGM9 and pGM6 (FIG. 2).

DNA fragments of pGM1, pGM6 and pGM9 were subcloned into pBluescriptIISK, and sequenced, from both ends using universal primers and internally by primer walking on both strands, using dye terminator chemistry, cycle sequencing and an ABI Prism 377 sequencer (Applied Biosystems). Sequence assembly and analysis was performed using Lasergene (DNAStar, Inc.), and Gapped BLAST and PSI BLAST (1).

The 3.7 kb fragment contained 5 ORFs (FIG. 2), whose predicted amino acid sequences encode PhaP (20 kDa protein), PhaQ, PhaR, PhaB and PhaC (41 kDa protein). The 20 and 41-kDa proteins were identified by their N-terminal amino acid sequences. Since the C-terminus for each of these two proteins extended beyond the boundaries of pGM1, the remaining sequence were obtained from plasmids pGM6 and pGM9.

Example 8

The pha Locus.

The 7,916 bp region (SEQ ID NO:1) containing pha genes from *Bacillus megaterium* was cloned, sequenced and characterized. It was shown to carry 8 complete and 1 incomplete open reading frame (FIG. 2, Tables 3 and 4). Coding sequences in this region were assigned on the basis of homology to known sequences, N-terminal amino acid sequences, putative ribosome binding sites and operon location. The complement and arrangement of genes flanking the pha genes in *Bacillus megaterium* are very similar to a region of *Bacillus subtilis* 168 (FIG. 2). This strain is negative for PHA and no known pha genes or sequences occur in its genome, for which the complete sequence is available (24). In place of pha genes in this region of *B. subtilis* are ykrI, ykrK and ykrL, which, respectively, code for putative proteins similar to two unknown proteins, and a probable heat shock protein.

TABLE 3

Sequence analysis results

| Sequence | Number of amino acids | Mol mass Daltons | Isoelectric point |
|---|---|---|---|
| ykoY | 271 | 29,996 | 6.89 |
| ykoZ | 236 | 27,662 | 9.36 |
| sspD | 65 | 7,027 | 8.58 |
| phaP | 170 | 19,906 | 5.29 |
| phaQ | 146 | 16,686 | 5.09 |
| phaR | 168 | 19,150 | 5.10 |
| phaB | 247 | 26,098 | 7.39 |
| phaC | 362 | 41,463 | 8.31 |
| ykrM | 318[a] | ND | ND |

[a]Partial protein.

since they are involved in determining inclusion-body size and shape, and are present in quantities up to 5% of total protein in the case of PHA producing *A. eutrophus* (48). It is an interesting observation that the amino acid sequences of phasin proteins are so dissimilar, even in closely related bacteria. Some similarity between such proteins would be expected in closely related bacteria, were they to have a role in inclusion-body biogenesis, however, conservation of sequence would be entirely unnecessary should they have a role as storage proteins.

The deduced amino acid sequences of PhaQ and PhaR also revealed small hydrophilic proteins with no significant identifiable similarity to known proteins (FIGS. 7 and 8). FIG. 1 (lane 2) shows that purified inclusion-bodies have proteins represented by bands of the approximate sizes of PhaQ (17 kDa) and PhaR (19 kDa), but the roles of these proteins are unknown. They may be non-orthologous replacements for the small putative gene products, whose roles are also unknown, coded in known pha gene clusters. The deduced amino acid sequence of PhaB, is similar in size and amino acid sequence to known phaB and fabG gene products (Table 2). The deduced amino acid sequence of PhaC shows that while it has low homology overall to known PhaC proteins, it is most similar to that of *T. violacea*, Synechocystis and *C. vinosum*. PhaC proteins from these three bacterial strains, respectively, have 355, 378, and 355 amino acids while PhaC from *Bacillus megaterium* has 362 amino acids. All other PhaC proteins studied are larger in size, and range from 559 amino acids for that of *P. oleovorans* (22) to 636 amino acids for that of *Rhizobium etli* (3). Alignment studies of sequences of all previously known

TABLE 4

Sequence homologies

| Sequence | Homologies to known and putative genes (accession no.)[a] | Identity | Similarity | Function or putative function |
|---|---|---|---|---|
| ykoY | YkoY, *B. subtilis* (Z99110) | 64% | 73% | Toxic anion resistance protein (24) |
| ykoZ | YkoZ, *B. subtilis* (Z99111) | 57% | 74% | RNA polymerase sigma factor (24) |
| sspD | SspD, *Bacillus megaterium* (P10572) | 100% | | Spore specific, DNA binding protein (4, 10) |
|  | SspD, *B. subtilis* (P04833) | 73% | 87% | |
| phaP | None | | | PHA inclusion-body structure, shape and size (49) |
| phaQ | None | | | Unknown |
| phaR | None | | | Unknown |
| phaB | FabG, Synechocystis (D90907) | 50% | 66% | Fatty acid biosynthesis (23) |
|  | PhaB, *C. vinosum* D (P45375) | 48% | 64% | 3-ketoacyl-CoA reductase (28) |
|  | FabG, *B. subtilis* (P51831) | 47% | 67% | Fatty acid biosynthesis (35) |
| phaC | PhaC, *T. violacea* (P45366) | 38% | 59% | PHA synthase (29, 23, 28) |
|  | PhaC, Synechocystis (D90906) | 37% | 56% | |
|  | PhaC, *C. vinosum* (P45370) | 35% | 55% | |
| ykrM | YkrM, *B. subtilis* (Z99111) | 55% | 71% | $Na^+$-transporting ATP synthase (24) |

[a]Accession numbers are SWISS-PROT, EMBL or DDBJ; [b]None, No discernible similarity to known sequences.

Example 9

The pha Nucleic Acid and Encoded Protein Sequences

The deduced amino acid sequence of PhaP shows a 20 kDa extremely hydrophilic product with no obvious similarity to known sequences (FIG. 6). Inclusion-body associated low molecular weight proteins (phasins) have been described in many bacteria (49), but where sequences were available no similarities of identifiable significance with PhaP of *Bacillus megaterium* were found.

Low molecular weight, PHA inclusion-body abundant proteins play an important role in PHA producing cells, PhaC proteins show that the synthases are either large single subunit enzymes (PhaC) or smaller two subunit enzymes (PhaC and PhaE). The *Bacillus megaterium* PhaC protein aligns poorly with large, single subunit enzymes such as the *P. oleovorans* PhaC (FIG. 3).

Example 10

Functionality of the pha Gene Cluster

It has been demonstrated that the phaP, -Q -R, -B and -C gene cluster can complement a deletion mutant of *B. megaterium*. This mutant PHA05 was constructed by a gene substitution technique. A plasmid (based on pGM10) in which the pha genes were substituted by the erythromycin gene, was propagated in *B. megaterium* 11561. Selection on erythromycin allowed isolation of the PHA05 mutant that was negative for PHA synthesis. Complementation with the phaP, -Q, -R, -B and -C gene cluster was obtained when pGM7H or pGM13 was introduced into the PHA05 strain.

Experiments introducing a phaR deletion of pGM13 (pGM61) into PHA05 suggests that the presence of phaR may be preferred for PHA synthesis. This result was confirmed by the recloning of phaR into pGM61 (pGM73) as it was isolated from PHA05(pGM61) strain, followed by the introduction of pGM73 into PHA05. Accumulation of PHA in PHA05(pGM73) confirmed the preference for phaR. It has been previously demonstrated that the small type PhaCs (see Example 17) is not sufficient for PHA synthesis; another peptide, PhaE of approximate size 30 kDa, is also required (51). These complementation studies suggest that it is preferable to combine PhaC of *B. megaterium* (also a small type PhaC) and phaR (19 kDa), however there is no sequence similarity between phaR of *B. megaterium* and phaE of other organisms.

Example 11

Mapping Transcription Starts

The transcription start points were mapped in the region from the EcoRI restriction site in phaP to the HindIII site in ykrM by primer extension analysis, using the Promega system for primer extension on RNA templates. DNA oligonucleotide primers, 17 to 20 nucleotides in length, were synthesized to match target sequences, initially at approximately 500 base pair intervals and subsequently at about 50 to 250 nucleotides down-stream from the predicted transcription start points. The $^{32}P$ 5' end-labeled primers were extended with reverse transcriptase using total RNA (10 μg per reaction) purified from *Bacillus megaterium* (31). The fragment length initially, and transcription start nucleotides subsequently, were determined by running the cDNA on a 8% denaturing polyacrylamide gel along-side the products of sequencing reactions, which were generated using the same 5'-end labeled primers. The primers used to identify the transcription start nucleotides for the phaP, phaQ, and phaRBC promoters were, respectively, CCCCTTTGTC-CATTGTTCCC (SEQ ID NO:16); CCATGTAGATTCCAC-CCTC (SEQ ID NO:17); and CTCCATCTCCTTTCTTGTG (SEQ ID NO:18).

Primer extension products showed a single band from each reaction, indicating one transcript, while control reactions in which RNA was omitted showed no bands. The extension products run alongside sequencing reaction products obtained with the same primer (FIG. 2C), identified the 5' ends of the transcripts thus allowing the putative promoter sequences at approximately −10 and −35-bp for phaP, -Q and -R to be identified. The arrangement of genes in the pha cluster of *Bacillus megaterium* is unique among those already published and phaA is notably absent. The phaP, -Q, -R, -B and -C genes were shown to be in a 4,104-bp region, with phaP and -Q transcribed in one orientation, each from a separate promoter, while phaR, -B and -C were divergently transcribed from a promoter in front of phaR. The putative promoters responsible for transcription of phaQ and phaR, phaB and phaC show strong similarity to both *Bacillus subtilis* Sigma A type (34) and *Escherichia coli*, Sigma 70 type promoters (14), which can express constitutively. This is in keeping with previous data for *Alcaligenes eutrophus* showing that phaC is constitutively synthesized, but PHA is not constitutively accumulated (19). The third putative promoter in this region, the phaP promoter, resembles a Sigma D (SigD) type promoter known to control the expression of a regulon of genes associated with flagellar assembly, chemotaxis and motility (13, 20, 46). In *Bacillus subtilis* Sigma D is expressed in the exponential phase and peaks in late exponential phase of growth. This parallels the pattern of PHA accumulation previously described for *Bacillus megaterium* 11561 (32). However, further experiments are required to test the hypothesis that PHA accumulation in regulated by sigma D or products of its resulting transcripts. The phaP gene has 18-bp duplicate sequences that could base-pair to form a rho-independent terminator close to its translational stop codon (FIG. 2B). The fact that the −35 promoter region of sspD is within this putative hairpin structure, suggests that transcription of phaP and sspD could be mutually exclusive, thus allowing the expression of phaP to play a regulatory role in the expression of sspD (spore specific storage protein).

Example 12

Expression of *Bacillus megaterium* pha Genes in *Escherichia coli* and *Pseudomonas putida*

Functionality of the *Bacillus megaterium* putative pha gene cluster was tested in *Escherichia coli*, which is naturally PHA negative, and *Pseudomonas putida* GPp104, a phaC⁻ mutant. Plasmids carrying one or more of these genes were introduced and the resulting transformants were tested for PHA accumulation following growth on LB or M9 medium with various carbon sources and the appropriate antibiotic for plasmid selection.

Triplicate 500 mL cultures, were grown in 2 liter flasks at 30° C., rotating at 250, using 1% inocula of 16 hour cultures, which had been grown in LB, centrifuged and resuspended in equal volumes of 0.9% saline. At 48 hours samples were removed for microscopy and cells were harvested, washed once in $dH_2O$ and lyophilized. For PHA extraction, lyophilized cells were suspended in 10 volumes of 5% (w/v) bleach, shaken at 65° C. for 1 hour and centrifuged. The pellet was resuspended in 10 volumes of 5% bleach and centrifuged followed by sequentially washing in water and 95% ethanol. The amount of PHA is expressed as percent PHA per mass of vacuum dried cells (w/w).

*Escherichia coli* carrying pGM7 or pGM 10 accumulated low levels of PHA while *Escherichia coli* carrying pGM1 or pGM6 accumulated no PHA. Fluorescence microscopy of Nile Blue A stained cells showed approximately 1 cell in 20 had one or several inclusion-bodies and the quantity of PHA produced was approximately 5% of cell dry weight. Since *Escherichia coli* does not have PhaA, a low level or no PHA is the expected result. However, in Pseudomonas where PhaA is not known to be required, *Pseudomonas putida* GPp104 (pGM107) accumulated PHA on rich as well as minimal medium with various carbon sources to >50% of cell dry weight, and 90 to 100% of cells appeared full of PHA (Table 5). The positive control *P. oleovorans*, (equivalent to wild-type *Pseudomonas putida*) accumulated PHA only when grown on longer chain carbon sources, and not on LB. No PHA was accumulated by the negative control or by *Pseudomonas putida* carrying phaC alone (pDR1). These results showed that this *Bacillus megaterium* gene cluster is functional in both *Escherichia coli* and *Pseudomonas putida*. It is not known if the negative results obtained with pDR1 was due to PhaC alone being insufficient to complement PhaC⁻ *Pseudomonas putida* or to synthesize PHA in *Escherichia coli*, or if the expression of phaC on pDR1 was not successful in producing protein.

TABLE 5

Cells with PHA as a percent[1] of total cells following growth on different carbon sources

| Substrates (no. C atoms) | Source of genes: Bacillus megaterium | Positive control: P. oleovorans | Negative control, vector only: Pseudomonas putida GPp104 (pSUP104) | phaP[n]QRBC: Pseudomonas putida GPp104 (pGM107) | phaC: Pseudomonas putida GPp104 (pDR1) |
|---|---|---|---|---|---|
| LB | 100 | 0 | 0 | 90 | 0 |
| LB/Glucose, 1% | 100 | 0 | 0 | 92 | 0 |
| M9/Caproate, 12 mM (C6) | no growth | 88 | 0 | 100* | 0 |
| M9/Octanoate, 12 mM (C8) | no growth | 90 | 0 | 92 | 0 |

[1]100%, PHA in all cells; 0%, no PHA in any cell; data averaged from >5 fields of each of 3 different cultures, error less than 5%. [n]N-terminus only present. *Cell shape distorted by large quantity of PHA.

These results suggest that the *B. megaterium* gene cluster, phaP, -Q, -R, -B, and -C, is functional in both *E. coli* and *P. putida* in so far as accumulation of PHA polymer. It is not known if the negative results obtained with pDR1 were due to PhaC alone being insufficient to complement the PhaC mutant of *P. putida* or to synthesize PHA in *E. coli*.

Example 13

Localization of PhaP and PhaC Proteins

Proteins associated with purified PHA inclusion-bodies may not accurately reflect the localization of the these proteins within the growing cell. Visualization of pha::gfp gene product fusion proteins in living cells throughout culture growth is a useful method for determining both the localization of the pha gene products and their comparative levels in growing cells. PhaP and PhaC, as fusion proteins (FIG. 4), localized to PHA inclusion-bodies at all time points tested throughout growth of *Bacillus megaterium* 11561. The negative control (pHPS9) showed no fluorescence at any time point. The localization control (pGM13C) showed non-localized green fluorescence at all time points. The profiles of PHA accumulation in these two control strains were similar to that of the wild-type, where the quantity of PHA decreased during the lag phase, increased during exponential phase, and continued to increase at a lower steady state rate in stationary phase growth (32).

At time 0, cultures of *Bacillus megaterium* carrying, pGM16.2, pGM13, pGM13C or pHPS9, grown in LB with LM[25] EM[1] for 24 hours at 35° C., were inoculated (5% v/v) into 75 mL of fresh media of the same composition, in 300 mL Naphelco flasks, and growth was continued at 27° C., 250 rpm. Optical densities of cultures were monitored and samples were removed for microscopy at time points starting at time 0, for up to 24 hours. One part of each sample was immediately observed for green fluorescence by embedding in 1% low melting point agarose for viewing in phase contrast and under fluorescence for GFP, magnification ×1000. Another part of each sample was stained for PHA and viewed under light microscopy and by fluorescence for PHA inclusion bodies, magnification ×1000. Images were recorded using identical parameters for all samples to allow comparison of fluorescence and light intensities (f-stop, 1/15; brightness, 0.6; sharpness, 1.0; contrast, 0.8; color, 0.3; see also methods and materials). Results are shown in FIG. 5.

PhaP, monitored as a PhaP::GFP fusion protein in pGM16.2 decreased significantly during the first half (2 hours) of lag phase growth, increased during late lag phase and early to mid-exponential phase, decreased in mid to late exponential phase and increased during stationary phase growth. A possible explanation for the rapid decrease of PhaP in lag phase is that PhaP may be a storage protein that is degraded as a source of amino acids. The profile of PHA accumulation in these cells (carrying pGM16.2) followed a similar pattern to that of PhaP except that PHA decreased only in the lag phase and continued to accumulate throughout other phases of culture growth. This data is consistent with PHA inclusion-bodies being a source of carbon, reducing equivalents and amino acids when the organism is first provided with fresh medium. Possible explanations as to why the level of PhaP and not PHA decreased at mid to late exponential phase are that either PhaP was synthesized at a slower rate than that of PHA, or PhaP was used as a source of amino acids at this phase of growth or both scenarios may apply.

PhaC, monitored as a PhaC::GFP fusion protein in pGM13 showed a similar profile of expression to that of PhaP with one exception: PhaC did not reduce in level during lag phase growth. It did, however, reduce in level in mid to late exponential phase growth, as did PhaP. The profile of PHA accumulation in these cells carrying PhaC::GFP was similar to that of cells carrying PhaP::GFP, except that the PHA level did not reduce during lag phase growth. The increased quantity of PhaC in the cell is a likely explanation since PhaC remained functional in the fusion protein PhaC::GFP. This was indicated by the fact that *Escherichia coli* DH5α (pC/GFP3) and *Escherichia coli* DH5α (pGM7) accumulated PHA to equivalent low levels, while the host strain alone, or carrying pGFPuv accumulated no PHA, as visualized by fluorescence microscopy of Nile Blue A stained cells. The reduction in level of PhaC in mid to late exponential phase, as was also seen with PhaP, is consistent with both PhaC and PhaP being synthesized at a slower rate than that of PHA.

In cells of all growth phases, inclusion-bodies were rarely visible under light in stained heat fixed cells while larger inclusion-bodies were visible in phase contrast of living cells. In older cultures (2 days and older) some cells were lysed, and showed PhaP::GFP and PhaC::GFP localized to free PHA inclusion-bodies. Both free and intracellular inclusion-bodies had doughnut shaped localization of GFP at some focal planes while at other focal planes the same inclusion-bodies appeared completely covered in GFP. We interpret this data as a difference in quantity of GFP that is visible when viewed through the edge or the center of the inclusion-bodies.

Example 14

Analysis of Bacillus megaterium 3-ketoacyl-CoA Reductase PhaB

Stereospecificity assays were conducted on the *Bacillus megaterium* reductase using various chain length enoyl-CoA esters (C4–C8, Table 6). The assay was done using crotonase from Sigma (L-hydroxy acids) or hydratase from *Rhodosprillum rubrum* (D-hydroxy acids) to form the 3-hydroxyacyl-CoA compounds from the enoyl-CoA esters. Acetoacetyl-CoA reductase activity was monitored spectrophotometrically as the reduction of $NADP^+$ while 3-hydroxyacyl-CoAs were oxidized. Based on the assay results (Table 6) the *Bacillus megaterium* reductase is a D-specific enzyme with a preference for C6 carbon chains. Enzyme reactions using NADH as electron donor for 3-ketoacyl-CoA reduction did not indicate significant enzyme activity with this cofactor.

TABLE 6

Analysis for stereo-specificity of the *Bacillus megaterium* 3-ketoacyl-CoA reductase.

| Clone #[a] | D-stereoisomer (hydratase) | Spec. act. U/mg | Clone # | L-stereoisomer (crotonase) | Spec. act. U/mg |
|---|---|---|---|---|---|
| B1-30 | Crotonyl CoA | 0.155 | B1-30 | Crotonyl CoA | 0.014 |
| B1-30 | C5 | 0.15 | B1-30 | C5 | 0.009 |
| B1-30 | C6 | 0.39 | B1-30 | C6 | 0.017 |
| B1-30 | C8 | 0.014 | B1-30 | C8 | 0.039 |
| B5-20 | Crotonyl CoA | 0.077 | B5-20 | Crotonyl CoA | 0.004 |
| B5-20 | C5 | 0.074 | B5-20 | C5 | 0.01 |
| B5-20 | C6 | 0.219 | B5-20 | C6 | 0.012 |
| B5-20 | C8 | 0.003 | B5-20 | C8 | 0.001 |
| Negative | Crotonyl CoA | 0.02 | Negative | Crotonyl CoA | 0.001 |
| Negative | C5 | 0.011 | Negative | C5 | 0.003 |
| Negative | C6 | 0.006 | Negative | C6 | 0.008 |
| Negative | C8 | 0.033 | Negative | C8 | 0.003 |

[a]Clone B1-30 contains pMON48213; clone B5-20 contains pMON48214.

Example 15

Verification of the Bacillus megaterium 3-ketoacyl-CoA Reductase for PHA Accumulation The functionality of the *Bacillus megaterium* sequence for PHA accumulation in a recombinant system was assayed. *Escherichia coli* DH5α harboring either pMON48222 (phaA$_{Re}$, phaB$_{Bm}$, phaC$_{Re}$) only, or two of the following plasmids: pJM9238 ΔAB (phaA and phaB deleted by FseI digest and religation) or pJM9117 ΔAB (phaA and phaB deleted by FseI digest and religation) and pMON48220 (phaA$_{Re}$, phaB$_{Bm}$,) was grown in LB+mannitol in concentrations of 1 or 2% (w/v), respectively. Cultures were induced for PHA accumulation at $OD_{600}$=0.6. Percentage PHA (Table 7) and enzyme activity (Table 8) were determined. Plasmid pMON48213 contains the same pha sequences as pMON48220, but was constructed with pSE380 (Invitrogen, Carlsbad, Calif.), a high level expression vector. Plasmid pMON48221 contains the same pha sequences as pMON48220, but lacks a small fragment of the multicloning site between phaA$_{Re}$ and phaB$_{Bm}$.

3-Ketoacyl-CoA reductase was monitored in a total volume of 1 mL containing 100 mM potassium phosphate buffer pH 7.0, 50 μM acetoacetyl-CoA and 150 μM NADPH. The reaction mixture contained between 5 and 50 μL cell extract. Assays were monitored spectrophotometrically at 340 nm.

TABLE 7

Application of the *Bacillus megaterium* 3-ketoacyl-CoA reductase for PHA formation in *Escherichia coli*

| Vectors | | % PHA | Standard deviation |
|---|---|---|---|
| pMON48222-4 | | 12.9 | |
| pMON48222-8 | | 19.2 | |
| | Average | 16.1 | ±4.5 |
| pJM9238 ΔAB | pMON48220 | 23.7 | |
| pJM9238 ΔAB | pMON48220 | 18.9 | |
| | Average | 21.3 | ±3.4 |
| pJM9238 ΔAB | Average | 1.5 | ±1.5 |
| pJM9117 ΔAB | pMON48220 | 12.5 | |
| pJM9117 ΔAB | pMON48220 | 3.9 | |
| | Average | 8.2 | ±6.1 |
| pJM9117 ΔAB | Average | 0.7 | ±0.1 |

TABLE 8

Enzyme activity of the *Bacillus megaterium* 3-ketoacyl-CoA reductase using pMON48220 and pMON48213

| Vector | acetoacetyl-CoA reductase[U/mg] |
|---|---|
| Negative control | 0.08 |
| pMON48220-2 | 0.24 |
| | 0.15 |
| pMON48220-9 | 0.22 |
| | 0.23 |
| Average | 0.21 ± 0.04 |
| pMON48213 | 4.0 |

TABLE 9

Verification of the *Bacillus megaterium* 3-ketoacyl-CoA reductase functionality

| *E. coli* DH5α containing plasmids | Relevant genotype | PHB content % CDW |
|---|---|---|
| pJM9238ΔAB, pMON34610 | phaC$_{Re}$ | nd |
| pJM9238ΔAB, pMON34575 | phaC$_{Re}$, phaA$_{Re}$ | 1.2 ± 0.4 |
| pJM9238ΔAB, pMON48221 | phaC$_{Re}$, phaA$_{Re}$, phaB$_{Bm}$ | 22.2 ± 4.7 | nd = not detectable

Example 16

Additional Sequences in Genomic Fragment

The 7,916 base pair genomic fragment (SEQ ID NO:1) additionally contained three complete open reading frames and one incomplete open reading frame encoding proteins in addition to PhaP, PhaQ, PhaR, PhaB, and PhaC. As indicated in Tables 3 and 4, sequence comparisons suggest that ykoY (SEQ ID NO:22) encodes toxic anion resistance protein YkoY (SEQ ID NO:23), ykoZ (SEQ ID NO:24) encodes RNA polymerase sigma factor protein YkoZ (SEQ ID NO:25), and ykrM (SEQ ID NO:26) encodes a portion of the $Na^+$-transporting ATP synthase protein YkrM (SEQ ID NO:27). Sequence sspD (SEQ ID NO:28) matches the known *Bacillus megaterium* sequence (4, 10) encoding SspD (SEQ ID NO:29). While the activity of the proteins is identified by is their similarity to other known proteins, it is possible that the proteins may have additional functionality involved in polyhydroxyalkanoate biosynthesis.

These nucleic acid and amino acid sequences may be used in nucleic acid segments, recombinant vectors, transgenic host cells, and transgenic plants.

Example 17

One and Two Subunit PHA Synthase Proteins

PHA synthases have been identified to be either one or two subunit enzymes (51). Single subunit enzymes have only the PhaC protein, while two subunit enzymes have PhaC and PhaE protein subunits. Nucleic acid sequences encoding PhaE subunits have been found to be located adjacent to the nucleic acid sequences encoding PhaC.

TABLE 10

One and two subunit PHA synthases

| Source organism (Reference) | Subunits | PhaC Amino acids |
|---|---|---|
| T. violacea (P45366, D48376) | 2 | 355 |
| C. vinosum (P45370, S29274) | 2 | 355 |
| T. pfennigii (WO 96/08566) | 2 | 357 |
| Synechocystis sp. PCC6803 (50, D90906, S77327) | 2 | 378 |
| P. oleovorans (22, A38604) | 1 | 559 |
| P. aeruginosa (S29305) | 1 | 559 |
| R. ruber (S25725) | 1 | 562 |
| R. eutropha (A34371) | 1 | 589 |
| A. caviae (D88825) | 1 | 594 |
| P. denitrificans (JC6023) | 1 | 624 |
| R. etli (3, U30612) | 1 | 636 |
| B. megaterium (SEQ ID NO:11) |  | 362 |

Based on the number of amino acids in the deduced sequence and homology to known PhaC proteins, the *B. megaterium* would be expected to be part of a two subunit synthase. However, the nucleic acid sequences adjacent to phaC in the 7,916 base pair genomic fragment show no significant similarity to a phaE sequence. Upstream of phaC is phaB, and downstream is ykrM, a suspected Na$^+$ transporting ATP synthase (Table 4). In combination with the observation that the *B. megaterium* sequences were able to complement *P. putida* GPp104 to accumulate PHA, this suggests that the *B. megaterium* phaC may encode a novel class of PHA synthase, i.e. a single subunit synthase with a molecular weight in the range of two subunit PhaC proteins.

Example 18

Pathway for the Production of C4/C6/C8/C 10 PHA Copolymers

FIG. 10 outlines a proposed biosynthetic pathway for the production of PHA copolymers incorporating C4 and/or C6 monomer units. Produced polymers may include C4-co-C6, C4-co-C8, C4-co-C6-co-C8, C6-co-C8, C6, and C8. A recombinant host cell or plant may be constructed to contain the nucleic acid sequences encoding the required enzymes.

The β-ketothiolase is preferably BktB (53, WO 98/00557). The β-ketothiolase can condense two molecules of acetyl-CoA to form acetoacetyl-CoA. This product may be reduced to 3HB-CoA by the *Bacillus megaterium* 3-ketoacyl-CoA reductase protein. 3HB-CoA may be converted to crotonyl-CoA by a hydratase such as that from *Aeromonas caviae* (54). Subsequent reduction to butyryl-CoA is performed by a butyryl-CoA dehydrogenase such as that cloned from *Clostridium acetobutylicum* (55). This product may be condensed with acetyl-CoA by the β-ketothiolase to afford 3-ketohexanoyl-CoA. This is the preferred substrate of the *Bacillus megaterium* reductase, leading to the production of 3-hydroxyhexanoyl-CoA. This product may be incorporated into C6 polymers or copolymers (e.g. C4-co-C6) by a PHA synthase having a broad substrate specificity (e.g. (56)). An additional round of condensation may lead to production of the C8 monomer, allowing the introduction of C8 into PHA polymers or copolymers. A further additional round of condensation may lead to production of the C10 monomer, allowing the introduction of C10 into PHA polymers or copolymers.

Example 19

Nucleic Acid Mutation and Hybridization

Variations in the nucleic acid sequence encoding a protein may lead to mutant protein sequences that display equivalent or superior enzymatic characteristics when compared to the sequences disclosed herein. This invention accordingly encompasses nucleic acid sequences which are similar to the sequences disclosed herein, protein sequences which are similar to the sequences disclosed herein, and the nucleic acid sequences that encode them. Mutations may include deletions, insertions, truncations, substitutions, fusions, shuffling of subunit sequences, and the like.

Mutations to a nucleic acid sequence may be introduced in either a specific or random manner, both of which are well known to those of skill in the art of molecular biology. A myriad of site-directed mutagenesis techniques exist, typically using oligonucleotides to introduce mutations at specific locations in a nucleic acid sequence. Examples include single strand rescue (Kunkel, T. *Proc. Natl. Acad. Sci. U.S.A.*, 82: 488–492, 1985), unique site elimination (Deng and Nickloff, *Anal. Biochem.* 200: 81, 1992), nick protection (Vandeyar, et al. *Gene* 65: 129–133, 1988), and PCR (Costa, et al. *Methods Mol. Biol.* 57: 31–44, 1996). Random or non-specific mutations may be generated by chemical agents (for a general review, see Singer and Kusmierek, *Ann. Rev. Biochem.* 52: 655–693, 1982) such as nitrosoguanidine (Cerda-Olmedo et al., *J. Mol. Biol.* 33: 705–719, 1968; Guerola, et al. *Nature New Biol.* 230: 122–125, 1971) and 2-aminopurine (Rogan and Bessman, *J. Bacteriol.* 103: 622–633, 1970), or by biological methods such as passage through mutator strains (Greener et al. *Mol. Biotechnol.* 7: 189–195, 1997).

Nucleic acid hybridization is a technique well known to those of skill in the art of DNA manipulation. The hybridization properties of a given pair of nucleic acids is an indication of their similarity or identity. Mutated nucleic acid sequences may be selected for their similarity to the disclosed nucleic acid sequences on the basis of their hybridization to the disclosed sequences. Low stringency conditions may be used to select sequences with multiple mutations. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed sequences. Conditions employed may include about 0.02 M to about 0.15 M sodium chloride, about 0.5% to about 5% casein, about 0.02% SDS and/or about 0.1% N-laurylsarcosine, about 0.001 M to about 0.03 M sodium citrate, at temperatures between about 50° C. and about 70° C. More preferably, high stringency conditions are 0.02 M sodium chloride, 0.5% casein, 0.02% SDS, 0.001 M sodium citrate, at a temperature of 50° C.

Example 20

Determination of Homologous and Degenerate Nucleic Acid Sequences

Modification and changes may be made in the sequence of the proteins of the present invention and the nucleic acid segments which encode them and still obtain a functional molecule that encodes a protein with desirable properties. The following is a discussion based upon changing the amino acid sequence of a protein to create an equivalent, or possibly an improved, second-generation molecule. The amino acid changes may be achieved by changing the codons of the nucleic acid sequence, according to the codons given in Table 11.

TABLE 11

Codon degeneracies of amino acids

| Amino acid | One letter | Three letter | Codons |
|---|---|---|---|
| Alanine | A | Ala | GCA GCC GCG GCT |
| Cysteine | C | Cys | TGC TGT |
| Aspartic acid | D | Asp | GAC GAT |
| Glutamic acid | E | Glu | GAA GAG |
| Phenylalanine | F | Phe | TTC TTT |
| Glycine | G | Gly | GGA GGC GGG GGT |
| Histidine | H | His | CAC CAT |
| Isoleucine | I | Ile | ATA ATC ATT |
| Lysine | K | Lys | AAA AAG |
| Leucine | L | Leu | TTA TTG CTA CTC CTG CTT |
| Methionine | M | Met | ATG |
| Asparagine | N | Asn | AAC AAT |
| Proline | P | Pro | CCA CCC CCG CCT |
| Glutamine | Q | Gln | CAA CAG |
| Arginine | R | Arg | AGA AGG CGA CGC CGG CGT |
| Serine | S | Ser | AGC AGT TCA TCC TCG TCT |
| Threonine | T | Thr | ACA ACC ACG ACT |
| Valine | V | Val | GTA GTC GTG GTT |
| Tryptophan | W | Trp | TGG |
| Tyrosine | Y | Tyr | TAC TAT |

Certain amino acids may be substituted for other amino acids in a protein sequence without appreciable loss of enzymatic activity. It is thus contemplated that various changes may be made in the peptide sequences of the disclosed protein sequences, or their corresponding nucleic acid sequences without appreciable loss of the biological activity.

In making such changes, the hydropathic index of amino acids may be considered. The importance of the hydropathic amino acid index in conferring interactive biological function on a protein is generally understood in the art (Kyte and Doolittle, *J. Mol. Biol.*, 157: 105–132, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics. These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

It is also understood in the art that the substitution of like amino acids may be made effectively on the basis of hydrophilicity. U.S. Pat. No. 4,554,101 (Hopp, T. P., issued Nov. 19, 1985) states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4).

It is understood that an amino acid may be substituted by another amino acid having a similar hydrophilicity score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

As outlined above, amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine, and isoleucine. Changes which are not expected to be advantageous may also be used if these resulted in functional fusion proteins.

Plant Vectors

In plants, transformation vectors capable of introducing nucleic acid sequences encoding polyhydroxyalkanoate biosynthesis enzymes are easily designed, and generally contain one or more nucleic acid coding sequences of interest under the transcriptional control of 5' and 3' regulatory sequences. Such vectors generally comprise, operatively linked in sequence in the 5' to 3' direction, a promoter sequence that directs the transcription of a downstream heterologous structural nucleic acid sequence in a plant; optionally, a 5' non-translated leader sequence; a nucleic acid sequence that encodes a protein of interest; and a 3' non-translated region that encodes a polyadenylation signal which functions in plant cells to cause the termination of transcription and the addition of polyadenylate nucleotides to the 3' end of the mRNA encoding the protein. Plant transformation vectors also generally contain a selectable marker. Typical 5'-3' regulatory sequences include a transcription initiation start site, a ribosome binding site, an RNA processing signal, a transcription termination site, and/or a polyadenylation signal. Vectors for plant transformation have been reviewed in Rodriguez et al. (Vectors: A Survey of Molecular Cloning Vectors and Their Uses, Butterworths, Boston., 1988), Glick et al. (Methods in Plant Molecular Biology and Biotechnology, CRC Press, Boca Raton, Fla., 1993), and Croy (Plant Molecular Biology Labfax, Hames and Rickwood (Eds.), BIOS Scientific Publishers Limited, Oxford, UK., 1993).

Plant Promoters

Plant promoter sequences can be constitutive or inducible, environmentally- or developmentally-regulated, or cell- or tissue-specific. Often-used constitutive promoters include the CaMV 35S promoter (Odell, J. T. et al., *Nature* 313: 810–812, 1985), the enhanced CaMV 35S promoter, the Figwort Mosaic Virus (FMV) promoter (Richins et al., *Nucleic Acids Res.* 20: 8451–8466, 1987), the mannopine synthase (mas) promoter, the nopaline synthase (nos) promoter, and the octopine synthase (ocs) promoter. Useful inducible promoters include promoters induced by salicylic acid or polyacrylic acids (PR-1, Williams, S. W. et al, *Biotechnology* 10: 540–543, 1992), induced by application of safeners (substituted benzenesulfonamide herbicides, Hershey, H. P. and Stoner, T. D., *Plant Mol. Biol.* 17: 679–690, 1991), heat-shock promoters (Ou-Lee et al., *Proc. Natl. Acad. Sci U.S.A.* 83: 6815–6819, 1986; Ainley et al., *Plant Mol. Biol.* 14: 949–967, 1990), a nitrate-inducible promoter derived from the spinach nitrite reductase gene (Back et al., *Plant Mol. Biol.* 17: 9–18, 1991), hormone-inducible promoters (Yamaguchi-Shinozaki, K. et al., *Plant Mol. Biol.* 15: 905–912, 1990; Kares et al., *Plant Mol. Biol.* 15: 225–236, 1990), and light-inducible promoters associated with the small subunit of RuBP carboxylase and LHCP gene families (Kuhlemeier et al., *Plant Cell* 1: 471, 1989; Feinbaum, R. L. et al., *Mol. Gen. Genet.* 226: 449–456, 1991; Weisshaar, B. et al., *EMBO J.* 10: 1777–1786, 1991; Lam, E. and Chua, N. H., *J. Biol. Chem.* 266: 17131–17135, 1990; Castresana, C. et al., *EMBO J.* 7: 1929–1936, 1988; Schulze-Lefert et al., *EMBO J.* 8: 651, 1989). Examples of useful tissue-specific, developmentally-regulated promoters include the β-conglycinin 7S promoter (Doyle, J. J. et al., *J. Biol. Chem.* 261: 9228–9238, 1986; Slighton and Beachy, *Planta* 172: 356–363, 1987), and seed-specific promoters (Knutzon, D. S. et al., *Proc. Natl. Acad. Sci U.S.A.* 89: 2624–2628, 1992; Bustos, M. M. et al., *EMBO J.* 10: 1469–1479, 1991; Lam and Chua, *Science* 248: 471, 1991; Stayton et al., *Aust. J. Plant. Physiol.* 18: 507, 1991). Plant functional promoters useful for preferential expression in seed plastids include those from plant storage protein genes and from genes involved in fatty acid biosynthesis in oilseeds. Examples of such promoters include the 5' regulatory regions from such genes as napin (Kridl et al., *Seed Sci. Res.* 1: 209–219, 1991), phaseolin, zein, soybean trypsin inhibitor, ACP, stearoyl-ACP desaturase, and oleosin. Seed-specific gene regulation is discussed in EP 0 255 378. Promoter hybrids can also be constructed to enhance transcriptional activity (Comai, L. and Moran, P. M., U.S. Pat. No. 5,106,739, issued Apr. 21, 1992), or to combine desired transcriptional activity and tissue specificity. A developing seed selective promoter may be obtained from the fatty acid hydroxylase gene of Lesquerella (P-lh) (Broun, P. and C. Somerville. *Plant Physiol.* 113: 933–942, 1997).

Plant Transformation and Regeneration

A variety of different methods can be employed to introduce such vectors into plant protoplasts, cells, callus tissue, leaf discs, meristems, etcetera, to generate transgenic plants, including Agrobacterium-mediated transformation, particle gun delivery, microinjection, electroporation, polyethylene glycolmediated protoplast transformation, liposome-mediated transformation, etcetera (reviewed in Potrykus, I. *Ann. Rev. Plant Physiol. Plant Mol. Biol.* 42: 205–225, 1991). In general, transgenic plants comprising cells containing and expressing DNAs encoding polyhydroxyalkanoate biosynthesis proteins can be produced by transforming plant cells with a DNA construct as described above via any of the foregoing methods; selecting plant cells that have been transformed on a selective medium; regenerating plant cells that have been transformed to produce differentiated plants; and selecting a transformed plant which expresses the protein-encoding nucleotide sequence.

Specific methods for transforming a wide variety of dicots and obtaining transgenic plants are well documented in the literature (Gasser and Fraley, *Science* 244: 1293–1299, 1989; Fisk and Dandekar, *Scientia Horticulturae* 55: 5–36, 1993; Christou, *Agro Food Industry Hi Tech, p. 17*, 1994; and the references cited therein).

Successful transformation and plant regeneration have been reported in the monocots as follows: asparagus (*Asparagus officinalis*; Bytebier et al., *Proc. Natl. Acad. Sci. U.S.A.* 84: 5345–5349, 1987); barley (*Hordeum vulgarae*; Wan and Lemaux, *Plant Physiol.* 104: 37–48, 1994); maize (*Zea mays*; Rhodes, C. A. et al., *Science* 240: 204–207, 1988; Gordon-Kamm et al., *Plant Cell* 2: 603–618, 1990; Fromm, M. E. et al., *Bio/Technology* 8: 833–839, 1990; Koziel et al., *Bio/Technology* 11: 194–200, 1993); oats (*Avena sativa;* Somers et al., *Bio/Technology* 10: 1589–1594, 1992); orchardgrass (*Dactylis glomerata*; Horn et al., *Plant Cell Rep.* 7: 469–472, 1988); rice (*Oryza sativa*, including indica and japonica varieties; Toriyama et al., *Bio/Technology* 6: 10, 1988; Zhang et al., *Plant Cell Rep.* 7: 379–384, 1988; Luo and Wu, *Plant Mol. Biol. Rep.* 6: 165–174, 1988; Zhang and Wu, *Theor. Appl. Genet.* 76: 835–840, 1988; Christou et al., *Bio/Technology* 9: 957–962, 1991); rye (*Secale cereale;* De la Pena et al., *Nature* 325: 274–276, 1987); sorghum (*Sorghum bicolor*; Casas, A. M. et al., *Proc. Natl. Acad. Sci. U.S.A.* 90: 11212–11216, 1993); sugar cane (*Saccharum* spp.; Bower and Birch, *Plant J.* 2: 409–416, 1992); tall fescue (*Festuca arundinacea*; Wang, Z. Y. et al., *Bio/Technology* 10: 691–696, 1992); turfgrass (*Agrostis palustris*; Zhong et al., *Plant Cell Rep.* 13: 1–6, 1993); wheat (*Triticum aestivum*; Vasil et al., *Bio/Technology* 10: 667–674, 1992; Weeks, T. et al., *Plant Physiol.* 102: 1077–1084, 1993; Becker et al., *Plant J.* 5: 299–307, 1994), and alfalfa (Masoud, S. A. et al., *Transgen. Res.* 5: 313, 1996).

Host Plants

Particularly useful plants for polyhydroxyalkanoate production include those that produce carbon substrates, including tobacco, wheat, potato, Arabidopsis, and high oil seed plants such as corn, soybean, canola, oil seed rape, sugarbeet, sunflower, flax, peanut, sugarcane, switchgrass, and alfalfa.

Example 21

Plastid Transformation

Alternatively, polyhydroxyalkanoate biosynthesis enzymes facilitating the increase in oil content of plants and/or herbicide resistance discussed herein can be expressed in situ in plastids by direct transformation of these organelles with appropriate recombinant expression constructs. Constructs and methods for stably transforming plastids of higher plants are well known in the art (Svab, Z. et al., *Plant Mol. Biol.* 14(2): 197–205, 1990; Svab et al., *Proc. Natl. Acad. Sci. USA.* 90(3): 913–917, 1993; Staub et al., *EMBO J.* 12(2): 601–606, 1993; Maliga et al., U.S. Pat. No. 5,451,513; PCT International Publications WO 95/16783, WO 95/24492, and WO 95/24493). These methods generally rely on particle gun delivery of DNA containing a selectable or scorable marker in addition to introduced DNA sequences for expression, and targeting of the DNA to the plastid genome through homologous recombination. Transformation of a wide variety of different monocots and dicots by particle gun bombardment is routine in the art (Hinchee et al., 1994; Walden and Wingender, 1995). The plastid may be transformed by using protoplast and PEG (polyethylene glycol) (Koop, et al., *Physiol. Plant.* 85: 339, 1992; Golds et al., *Bio/Technol.* 11: 95–97, 1993), cocultivation of protoplasts and Agrobacteria carrying transformation vectors (De Block et al., *EMBO J.* 4: 1367–1372, 1985), and by electroporation (Kin-Ying et al., *Plant J.* 4: 737, 1996).

Nucleic acid constructs for plastid transformation generally comprise a targeting segement comprising flanking nucleic acid sequences substantially homologous to a predetermined sequence of a plastid genome, which targeting segment enables insertion of nucleic acid coding sequences of interest into the plastid genome by homologous recombination with the predetermined sequence; a selectable marker sequence, such as a sequence encoding a form of plastid 16S ribosomal RNA that is resistant to spectinomycin or streptomycin, or that encodes a protein which inactivates spectinomycin or streptomycin (such as the aadA gene), disposed within the targeting segment, wherein the selectable marker sequence confers a selectable phenotype upon plant cells, substantially all the plastids of which have been transformed with the nucleic acid construct; and one or more nucleic acid coding sequences of interest disposed within the targeting segment relative to the selectable marker sequence so as not to interfere with conferring of the selectable phenotype. In addition, plastid expression constructs also generally include a plastid promoter region and a transcription termination region capable of terminating transcription in a plant plastid, wherein the regions are operatively linked to the nucleic acid coding sequences of interest.

A further refinement in chloroplast transformation/expression technology that facilitates control over the timing and tissue pattern of expression of introduced nucleic acid coding sequences in plant plastid genomes has been described in PCT International Publication WO 95/16783. This method involves the introduction into plant cells of constructs for nuclear transformation that provide for the expression of a viral single subunit RNA polymerase and targeting of this polymerase into the plastids via fusion to a plastid transit peptide. Transformation of plastids with nucleic acid constructs comprising a viral single subunit RNA polymerase-specific promoter specific to the RNA polymerase expressed from the nuclear expression constructs operably linked to nucleic acid coding sequences of interest permits control of the plastid expression constructs in a tissue and/or developmental specific manner in plants comprising both the nuclear polymerase construct and the plastid expression constructs. Expression of the nuclear RNA polymerase coding sequence can be placed under the control of either a constitutive promoter, or a tissue- or developmental stage-specific promoter, thereby extending this control to the plastid expression construct responsive to the plastid-targeted, nuclear-encoded viral RNA polymerase. The introduced nucleic acid coding sequence can be a single encoding region, or may contain a number of consecutive encoding sequences to be expressed as an engineered or synthetic operon. The latter is especially attractive where, as in the present invention, it is desired to introduce multigene biochemical pathways into plastids. This approach is more complex using standard nuclear transformation techniques since each gene introduced therein must be engineered as a monocistron, including an encoded transit peptide and appropriate promoter and terminator signals. Individual gene expression levels may vary widely among different cistrons, thereby possibly adversely affecting the overall biosynthetic process. This can be avoided by the chloroplast transformation approach.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

REFERENCES

The following references, to the extent that they provide exemplary procedural or other details supplementary to those set forth herein, are specifically incorporated herein by reference.

1. Altschul, S. F., T. L. Madden, A. A. Schaffer, J. Zhang, Z. Zhang, W. Miller, and D. J. Lipman. 1997. Gapped BLAST and PSI BLAST: a new generation of protein database search programs. *Nucleic Acids Res.*, 25: 3389–3402.
2. Anderson, A. and E. A. Dawes. 1990. Occurrence, metabolism, metabolic role, and industrial uses of bacterial polyhydroxyalkanoates. *Microbiol Rev.*, 54: 450–472.
3. Cevallos, M. A., S. Encarnacion, A. Leija, Y. Mora, and J. Mora. 1996. Genetic and physiological characterization of a *Rhizobium etli* mutant strain unable to synthesize poly-beta-hydroxybutyrate. *J. Bacteriol.*, 178: 1646–1654.
4. Connors, M. J., J. M. Mason, and P. Setlow. 1986. Cloning and nucleotide sequencing of genes for three small, acid soluble proteins *Bacillus subtilis* spores. *J. Bacteriol.*, 166: 417–425.
5. deSmet, M. J., G. Eggink, B. Witholt, J. Kingma, and H. Wynberg. 1983. Characterization of intracellular inclusions formed by *Pseudomonas oleovorans* during growth on octane. *J. Bacteriol.*, 154: 870–878.

6. Dunlop, W. and A. W. Robards. 1973. Ultrastructural study of poly-β-hydroxybutyrate granules from *Bacillus cereus*. *J Bacteriol.*, 114: 1271–1280.

7. Eggink, G., P. de Waard, and G. N. M. Huijberts. 1992. The role of fatty acid biosynthesis and degradation in the supply of substrates for poly(3-hydroxyalkanoate) formation in *Pseudomonas putida*. *FEMS Microbiol. Rev.*, 103: 159–164.

8. Ellar, D., D. G. Lundgren, K. Okamura, and R. H. Marchessault. 1968. Morphology of poly-β-hydroxybutyrate granules. *J. Mol. Biol.*, 35: 489–502.

9. Fliss, E. R., A. C. Loshon, and P. Setlow. 1986. Genes for *Bacillus megaterium* small, acid-soluble spore proteins: Cloning and nucleotide sequence of three additional genes from this multigene family. *J. Bacteriol.*, 165: 467–473.

10. Fliss, E. R. and P. Setlow. 1984. *Bacillus megaterium* spore protein C-3: nucleotide sequence of its gene and the amino acid sequence at its spore cleavage site. *Gene*, 30: 167–172.

11. Fuller, R. C., J. P. O'Donnell, J Saulnier, T. E. Redlinger, J. Foster, and R. W. Lenz. 1992. The supramolecular architecture of the polyhydroxyalkanoate inclusions in *Pseudomonas oleovorans*. *FEMS Microbiol. Rev.*, 103: 279–288.

12. Gemgross, T. U., P. Reilly, J. Stubbe, A. J. Sinskey, and O. P. Peoples. 1993. Immunocytochemical analysis of poly-β-hydroxybutyrate (PHB) synthase enzyme at the surface of PHB granules. *J. Bacteriol.*, 175: 5289–5293.

13. Gilman, M. Z., J. L. Wings, and M. J. Chamberlin. 1981. Nucleotide sequence of two *Bacillus subtilis* promoters used by *Bacillus subtilis* sigma-28 RNA polymerase. *Nucleic Acids Res.*, 9: 5991–6000.

14. Gitt, M. A., L. F. Wang, and R. H. Doi. 1985. A strong sequence homology exists between RNA polymerase sigma factors of *Bacillus subtilis* and *Escherichia coli*. *J. Biol. Chem.*, 260: 7178–7185.

15. Griebel, R., Z. Smith, and M. Merrick. 1968. Metabolism of poly-β-hydroxybutyrate. 1. Purification, composition, and properties of native poly-β-hydroxyburyrate granules from *Bacillus megaterium*. *Biochem.*, 7: 3676–3681.

16. Haima, P., D. van Sinderen, H. Scholting, S. Bron, and G. Venema. 1990. Development of β-galactosidase α-complementation system for molecular cloning in *Bacillus subtilis*. *Gene*, 86: 63–69.

17. Haywood, G. W., A. J. Anderson, L. Chu, and E. A. Dawes. 1988. The role of NADH- and NADPH-linked acetoacetyl-CoA reductases in the poly-3-hydroxybutyrate synthesizing organism *Alcaligenes eutrophus*. *FEMS Microbiol. Lett.*, 52: 259–264.

18. Haywood, G. W., A. J. Anderson, L. Chu, and E. A. Dawes. 1988. Characterization of two 3-ketothiolases in the polyhydroxyalkanoate synthesizing organism *Alcaligenes eutrophus*. *FEMS Microbiol. Lett.*, 52: 91–96.

19. Haywood, G. W., A. J. Anderson, and E. A. Dawes. 1989. The importance of PHB-synthase substrate specificity in polyhydroxyalkanoate synthesis by *Alcaligenes eutrophus*. *FEMS Microbiol. Lett.*, 57: 1–6.

20. Helmann, J. D. 1991. Alternative sigma factors and the regulation of flagellar gene expression. *Mol. Microbiol.*, 5: 2875–2882.

21. Huang, A. H. C. 1992. Oil bodies and oleosins in seeds. *Annu. Rev. Plant Physiol. Plant Mol. Biol.*, 43: 177–200.

22. Huisman, G. W., E. Wonink, R. Meima, B. Kazemier, P. Terpstra, and B. Witholt. 1991. Metabolism of poly(3-hydroxyalkanoates) (PHAs) by *Pseudomonas oleovorans*. *J. Biol. Chem.*, 266: 2191–2198.

23. Kaneko, T. et al. 1996. Sequence analysis of the genome of the unicellular cyanobacterium Synechocystis sp. strain PCC6803. II. Sequence determination of the entire genome and assignment of potential protein-coding regions. *DNA Res.*, 3: 109–136.

24. Kunst, N. et al. 1997. The complete genome sequence of the Gram-positive bacterium *Bacillus subtilis*. *Nature*, 390: 249–256.

25. Lauzier, C., R. H. Marchessault, P. Smith, and H. Chanzy. 1992. Structural study of isolated poly(β-hydroxybutyrate) granules. *Polymer*, 33: 823–827.

26. Lee, S. Y. 1995. Bacterial polyhydroxyalkanoates. *Biotechnology & Engineering*, 49: 1–14.

27. Liebergesell, M., B. Schmidt, and A. Steinbüchel. 1992. Isolation and identification of granule-associated proteins relevant for poly(hydroxyalkanoic acid) biosynthesis in *Chromatium vinosum* D. *FEMS Microbiol. Lett.*, 99: 227–232.

28. Liebergesell, M. and A. Steinbüchel. 1992. Cloning and nucleotide sequences of genes relevant for biosynthesis of poly(3-hydroxybutyric acid) in *Chromatium vinosum* strain D. *Eur. J. Biochem.*, 209: 135–150.

29. Liebergesell, M. and A. Steinbüchel. 1993. Cloning and molecular analysis of the poly (3-hydroxybutyric acid) biosynthetic genes of *Thiocystis violacea*. *Appl. Microbiol. Biotechnol.*, 38: 493–501.

30. Lundgren, D. G., R. M. Pfister, and J. M. Merrick. 1964. Structure of poly-β-hydroxybutyric acid granules. *J. Gen. Microbiol.*, 34: 441–446.

31. Magni, C., P. Marini, and D. de Mendoza. 1995. Extraction of RNA from gram-positive bacteria. *Biotechniques*, 19: 882–884.

32. McCool, G. J., T. Fernandez, N. Li, and M. C. Cannon. 1996. Polyhydroxyalkanoate inclusion-body growth and proliferation in *Bacillus megaterium*. *FEMS Microbiol. Lett.*, 137: 41–48.

33. Miller, J. H. 1972. Experiments in molecular genetics. Cold Spring Harbor Laboratory, Cold Spring Harbor, N.Y.:

34. Moran, C. P. Jr., N. Lang, S. F. J. LeGrice, G. Lee, M. Stephens, A. L. Sonnenshein, J. Pero, and R. Losick. 1982. Nucleotide sequences that signal the initiation of transcription and translation in *Bacillus subtilis*. *Mol. Gen. Genet.*, 186: 339–346.

35. Morbidoni, H. R., D. de Mendoza, and J. E. Cronan. 1996. *Bacillus subtilis* acyl carrier protein is encoded in a cluster of lipid biosynthesis genes. *J. Bacteriol.*, 178: 4794–4800.

36. Pieper-Furst, U., M. H. Madkour, F. Mayer, and A. Steinbüchel. 1994. Purification and characterization of a 14-kilodalton protein that is bound to the surface of polyhydroxyalkanoic acid granules in *Rhodococcus ruber*. *J. Bacteriol.*, 176: 4328–4337.

37. Pieper-Furst, U., M. H. Madkour, F. Mayer, and A. Steinbüchel. 1995. Identification of the region of a 14-kilodalton protein of *Rhodococcus ruber* that is responsible for the binding of this Phasin to polyhydroxyalkanoic acid granules. *J. Bacteriol.*, 177: 2513–2523.

38. Sambrook, J., E. F. Fritsch & T. Maniatis. 1989. Molecular Cloning: A Laboratory Manual., 2nd ed. Cold Spring Harbor Laboratory Press, Cold Spring Harbor, N.Y.

39. Shark, K. B., F. D. Smith, P. R. Harpending, and J. L. Rasmussen. 1991. Biolistic transformation of a procaryote, *Bacillus megaterium*. *Appl. Environ. Microbiol.*, 57: 480–485.

40. Simon, R., Priefer, U. & Pühler, A. 1983. In A. Pühler (Ed.), Molecular genetics of the bacteria-plant interaction. Springer, Berlin. p. 98–106.
41. Steinbüchel, A. 1991. Polyhydroxyalkanoic acids. p. 123–213. In D. Byrom (Ed.), Biomaterials, novel materials from biological sources. Macmillan Publishers Ltd., Basingstoke, England.
42. Steinbüchel, A., K. Aerts, W. Babel, C. Follner, M. Liebergesell, M. H. Madkour, F. Mayer, U. Pieper-Furst, A. Pries, H. E. Valentin, and R. Wieczorek. 1995. Considerations on the structure and biochemistry of bacterial polyhydroxyalkanoic acid inclusions. *Can. J. Microbiol.,* 41: 94–105.
43. Steinbüchel, A., E. Hustede, M. Liebergesell, U. Pieper, A. Timm, and H. Valentin. 1992. Molecular basis for biosynthesis and accumulation of polyhydroxyalkanoic acids in bacteria. *FEMS Microbiol. Rev.,* 103: 217–230.
44. Steinbüchel, A. and H. G. Schlegel. 1991. Physiology and molecular genetics of poly(β-hydroxyalkanoic acid) synthesis in *Alcaligenes eutrophus. Mol. Microbiol.,* 5: 535–542.
45. Steinbüchel, A. and H. E. Valentin. 1995. Diversity of bacterial polyhydroxyalkanoic acids. *FEMS Microbiol. Lett.,* 128: 219–228.
46. Vary, P. 1993. The genetic map of *Bacillus megaterium,* p. 475–481. In A. L. Sonenshein, J. A. Hoch & R. Losich (Eds.), *Bacillus subtilis* and other gram positive bacteria. American Society for Microbiology, Washington, D.C.
47. Wang, W. S. and D. G. Lundgren. 1969. Poly-β-hydroxybutyrate in the chemolithotrophic bacterium *Ferrobacillus ferrooxidans. J. Bacteriol.,* 97: 947–950.
48. Wieczorek, R., A. Pries, A. Steinbüchel, and F. Mayer. 1995. Analysis of a 24-kilodalton protein associated with the polyhydroxyalkanoic acid granules in *Alcaligenes eutrophus. J. Bacteriol.,* 177: 2425–2435.
49. Wieczorek, R., A. Steinbüchel, and B. Schmidt. 1996. Occurrence of polyhydroxyalkanoic acid granule-associated proteins related to the *Alcaligenes eutrophus* H16 GA24 protein in other bacteria. *FEMS Microbiol. Lett.,* 135: 23–30.
50. Hein, S., Tran, H., and A. Steinbüchel. 1998. Synechocystis sp. PCC6803 possesses a two-component polyhydroxyalkanoic acid synthase similar to that of anoxygenic purple sulfur bacteria. *Arch. Microbiol.,* 170 (3): 162–70.
51. Steinbüchel, A., Hustede, E., Liebergesell, M., Pieper, U., Timm, A., and H. Valentin. 1992. Molecular basis for biosynthesis and accumulation of polyhydroxyalkanoic acids in bacteria. *FEMS Microbiol. Rev.* 103: 217–230.
52. Basak, A., Boudreault, A., Chen, A., Chretien, M., Seidah, N. G., and C. Lazure. 1995. Application of the multiple antigenic peptides (MAP) strategy to the production of prohormone convertases antibodies: synthesis, characterization and use of 8-branched immunogenic peptides. *J. Pept. Sci.* 1(6): 385–95.
53. Slater, S., K. L. Houmiel, M. Tran, T. A. Mitsky, T. B. Taylor, S. R. Padgette, and K. J. Gruys. 1998. Multiple β-ketothiolases mediate poly(β-hydroxyalkanoate) copolymer synthesis in *Ralstonia eutropha. J. Bacteriol.* 180: 1979–1987.
54. Fukui, T., N. Shiomi, and Y. Doi. 1998. Expression and characterization of (R)-specific enoyl coenzyme A hydratase involved in polyhydroxyalkanoate biosynthesis in *Aeromonas caviae. J. Bacteriol.* 180: 667–6673.
55. Boynton, Z. L., G. N. Bennett, and F. B. Rudolph. 1996. Cloning, sequencing, and expression of clustered genes encoding b-hydroxybutyryl-coenzyme A (CoA) dehydrogenase, crotonase, and butyryl-CoA dehydrogenase from *Clostridium acetobutylicum* ATCC 824. *J. Bacteriol.* 178: 3015–3024.
56. Liebergesell, M., F. Mayer, and A. Steinbüchel. 1993. Analysis of polyhydroxyalkanoic acid-biosynthesis genes of anoxygenic phototrophic bacteria reveals synthesis of a polyester exhibiting an unusual composition. *Appl. Microbiol. Biotechnol.* 40:292–300.

What is claimed is:

1. An isolated or purified nucleic acid segment comprising a nucleic acid sequence encoding a 3-keto-acyl-CoA reductase protein, wherein the nucleic acid sequence is a nucleic acid sequence at least about 80% identical to SEQ ID NO:8 that hybridizes under stringent conditions to SEQ ID NO:8 or the complement thereof, and encodes a protein at least about 80% identical to SEQ ID NO:9, and has 3-keto-acyl-CoA reductase activity higher for D-isomers of C6 carbon chains than for C4 carbon chains.

2. A recombinant vector comprising in the 5' to 3' direction:

a) a promoter that directs transcription of a structural nucleic acid sequence encoding a 3-keto-acyl-CoA reductase protein;

b) a structural nucleic acid sequence encoding a 3-keto-acyl-CoA reductase protein; wherein the structural nucleic acid sequence is a nucleic acid sequence at least about 80% identical to SEQ ID NO:8; that hybridizes under stringent conditions to SEQ ID NO:8 or the complement thereof; and encodes a protein at least about 80% identical to SEQ ID NO:9 and that has 3-keto-acyl-CoA reductase activity higher for for D-isomers of C6 carbon chains that for C4 carbon chains; and c) a 3' transcription terminator.

3. A recombinant cell comprising a nucleic acid segment encoding a 3-keto-acyl-CoA reductase protein, wherein the nucleic acid segment is a nucleic acid sequence at least about 80% identical to SEQ ID NO:8 that hybridizes under stringent conditions to SEQ ID NO:8 or the complement thereof; and encodes a protein at least about 80% identical to SEQ ID NO:9 and that has 3-keto-acyl-CoA reductase activity higher for for D-isomers of C6 carbon chains than for C4 carbon chains.

4. A genetically transformed plant cell comprising in the 5' to 3' direction:
a) a promoter that directs transcription of a structural nucleic acid sequence encoding a 3-keto-acyl-CoA reductase protein;
b) a structural nucleic acid sequence encoding a 3-keto-acyl-CoA reductase protein; wherein the structural nucleic acid sequence is a nucleic acid sequence at least about 80% identical to SEQ ID NO:8 that hybridizes under stringent conditions to SEQ ID NO:8 or the complement thereof; and
encodes a protein at least about 80% identical to SEQ ID NO:9 and that has 3-keto-acyl-CoA reductase activity higher for for D-isomers of C6 carbon chains than for C4 carbon chains;
c) a 3' transcription terminator; and
d) a 3' polyadenylation signal sequence that directs the addition of polyadenylate nucleotides to the 3' end of RNA transcribed from the structural nucleic acid sequence.

5. A genetically transformed plant comprising in the 5' to 3' direction:
(a) a promoter that directs transcription of a structural nucleic acid sequence encoding a 3-keto-acyl-CoA reductase protein;
b) a structural nucleic acid sequence encoding a 3-keto-acyl-CoA reductase protein; wherein the structural nucleic acid sequence is a nucleic acid sequence at least about 80% identical to SEQ ID NO:8 that hybridizes under stringent conditions to SEQ ID NO:8 or the complement thereof; and
encode a protein at least about 80% identical to SEQ ID NO:9 and that has 3-keto-acyl-CoA reductase activity higher for for D-isomers of C6 carbon chains than for C4 carbon chains;
c) a 3' transcription terminator; and
d) a 3' polyadenylation signal sequence that directs the addition of polyadenylate nucleotides to the 3' end of RNA transcribed from the structural nucleic acid sequence.

6. An isolated or purified nucleic acid segment comprising a nucleic acid sequence encoding a polyhydroxyalkanoate synthase protein, wherein the nucleic acid segment is a nucleic acid sequence at least about 80% identical to SEQ ID NO:10 that hybridizes under stringent conditions to SEQ ID NO:10 or the complement thereof; and encodes a protein at least about 80% identical to SEQ ID NO:11 and that has polyhydroxyalkanoate synthase activity.

7. A recombinant vector comprising in the 5' to 3' direction:
a) a promoter that directs transcription of a structural nucleic acid sequence encoding a polyhydroxyalkanoate synthase protein;
b) a structural nucleic acid sequence encoding a polyhydroxyalkanoate synthase protein; wherein the structural nucleic acid sequence is a nucleic acid sequence at least about 80% identical to SEQ ID NO:10 that hybridizes under stringent conditions to SEQ ID NO:10 or the complement thereof; and
encodes a protein at least about 80% identical to SEQ ID NO:11 and that has polyhydroxyalkanoate synthase activity; and
c) a 3' transcription terminator.

8. A recombinant host cell comprising a nucleic acid segment encoding a polyhydroxyalkanoate synthase protein, wherein the nucleic acid segment is a nucleic acid sequence at least about 80% identical to SEQ ID NO:10 that hybridizes under stringent conditions to SEQ ID NO:10 or the complement thereof; and encodes a protein at least about 80% identical to SEQ ID NO:11 and that has polyhydroxyalkanoate synthase activity.

9. A genetically transformed plant cell comprising in the 5' to 3' direction:
a) a promoter that directs transcription of a structural nucleic acid sequence encoding polyhydroxyalkanoate synthase protein;
b) a structural nucleic acid sequence encoding polyhydroxyalkanoate synthase protein; wherein the structural nucleic acid sequence is a nucleic acid sequence at least about 80% identical to SEQ ID NO:10 that hybridizes under stringent conditions to SEQ ID NO:10 or the complement thereof; and
encodes a protein at least about 80% identical to SEQ ID NO:11 and that has polyhydroxyalkanoate synthase activity;
c) a 3' transcription terminator; and
d) a 3' polyadenylation signal sequence that directs the addition of polyadenylate nucleotides to the 3' end of RNA transcribed from the structural nucleic acid sequence.

10. A genetically transformed plant comprising in the 5' to 3' direction:
a) a promoter that directs transcription of a structural nucleic acid sequence encoding a polyhydroxyalkanoate synthase protein;
b) a structural nucleic acid sequence encoding a polyhydroxyalkanoate synthase protein; wherein the structural nucleic acid sequence is a nucleic acid sequence at least about 80% identical to SEQ ID NO:10 that hybridizes under stringent conditions to SEQ ID NO:10 or the complement thereof; and
encodes a protein at least about 80% identical to SEQ ID NO:11 and that has polyhydroxyalkanoate synthase activity;
c) 3transcription terminator; and
d) a 3polyadenylation signal sequence that directs the addition of polyadenylate nucleotides to the 3' end of RNA transcribed from the structural nucleic acid sequence.

11. The nucleic acid segment, vector, or cell of claims 1, 3, 4, or 5, wherein the nucleic acid sequence is SEQ ID NO:8.

12. The nucleic acid segment, vector, or cell of claims 6, 7, 8, 9, or 10 wherein the nucleic acid sequence is SEQ ID NO:10.

* * * * *

UNITED STATES PATENT AND TRADEMARK OFFICE
CERTIFICATE OF CORRECTION

PATENT NO. : 6,835,820 B2
APPLICATION NO. : 09/479040
DATED : December 28, 2004
INVENTOR(S) : Maura Cannon et al.

It is certified that error appears in the above-identified patent and that said Letters Patent is hereby corrected as shown below:

Claim 2, Column 81, line 1, replace "that" with --than--.
Claim 3, Column 81, line 12, replace "for for" with --for--.
Claim 3, Column 81, line 27, replace "for for" with --for--.
Claim 5, Column 81, line 45, replace "encode" with --encodes--.
Claim 10, Column 82, line 53, replace "3transcription" with --3' transcription--.
Claim 10, Column 82, line 54, replace "3polyadenylation" with --3' polyadenylation--.

Signed and Sealed this

Seventeenth Day of July, 2007

JON W. DUDAS
*Director of the United States Patent and Trademark Office*

SEQUENCE LISTING

<160> NUMBER OF SEQ ID NOS: 29

<210> SEQ ID NO 1
<211> LENGTH: 7916
<212> TYPE: DNA
<213> ORGANISM: Bacillus megaterium

<400> SEQUENCE: 1

```
aagcttaaca aaaggttaga gggcttttaa ttgacttatt aatgaacctt ttataaaata      60
aaaacaactt aatacattta cttcttacgg agtaaagggg agtagcgtca gggaaacctg     120
aaacaaagtc gtcattacat ggagtattcc atcggctttg ttggcataat gattatgctt     180
agcaagacct ttgccatatt tggcaaaggt cttttttgtgt tttattccgg taatgaggat     240
aaataaactt atacaaagaa acgagagggg atttttatgg atgcatcact tttgttagag     300
tatggatggg tattgctagt gctggttgca ttagaaggaa ttttggcggc ggataatgct     360
cttgtgatgg ctattatggt caaacattta ccggaagaaa aacgcaagaa ggcattattt     420 tacgattag ccggtgcctt tatttttaga tttggttcgt tgttcttgat ttcatttta     480 gtcgacgtat ggcagcttca agctatagga gccatttact tattgttcat ttccattaat     540
catattgtga agcgatatgt gaaaaagac gatcatgaaa aagtgaaaga agcagacgag     600
```

```
aaaaagggct caggtttctg gatgacggtt ttaaaagtag aaatagcaga cattgctttt      660
gccgttgatt caattttggc cgctgtggct ctcgccgtta cgttgccaac aacaaatctt      720
cctcaaattg gcggactcga cggcggacaa ttcttggtga tcttcgccgg aggaattatg      780
ggattaatta ttatgcgttt tgctgcaact tggttcgtca agctattaaa tacgcgccca      840
ggcctagaaa cggcggcttt tgctattgta ggctgggtag gagttaagtt agcggtctat      900
acccttgctc atccagagtt aggtattatt aatgaacatt tccctgaatc aaaagtgtgg      960
aaaattacgt tttggattgt gttacttggc atagctgctt caggctggtt tctatctaaa     1020
aataaagaac aaactgatct tgaaggctca gagaaagaaa agaatcgtt aaaaaaaatt      1080
gaaaatcaat aataaaaaaa acgcgccttc aatgttaatt gaaggcgcgt tttttatagg     1140
gggataaaat acctagttta gattgtttaa ataaagggta aagaattaa ttactgttta      1200
attactgtat atccgaatgt tttgcttttt cgttcatatt ctgtagagaa cagagccgtg     1260
agtaattcag ttcaatgaag tttatttcag tttataaaca tatatttcaa atgtatgtta     1320
attggtaaaa ttgagctatt atgggttata ataaaggaaa attaaaagga gcagagcgct     1380
tctcaaccct gttcgtcatc aaaagaatgg atattaacat ggtataaagc aactgagtat     1440
agtaaaagag gtgaagccaa tgctcacaaa agttcaaacg cctccatcgc ttgaaacgct     1500
tgtactgacg attcagcaag gggataaaca attacataat gaaatgattc aacaatataa     1560
accgtttatt gctaaagttg tttcagctgt atgtaaacgt tatataagtg aagctgacga     1620
tgaatttagc attggtctga ttgcatttaa tgaagccatt gaaaattaca caatccaaaa     1680
aggacgatct cttcttgcat ttgcggaact tattattaaa agaagagtaa tcgactatat     1740
tcgaaaagaa aagcgaaatc aaacgctgct ctataaccga attgaaaatg aaggttttat     1800
tcaaggtaag gtagaaaggg atatatcgct ttctaactat aaaaggcaaa gtgaaacttc     1860
atatattcaa gaggaaatga cttatttttg tcaggcgcta aaattgttta aattaactct     1920
tgaagacatt attaacacgt ctcctaaaca taaggatgca aggggaaatg cagtggaagt     1980
tgcatctttt atcgtcaatg aaaaagaatt aaaagataag ctgttttaa agcggcagct      2040
tcctattcgc ttgattgaaa acatgtcaa agtaagccgg aaaacaattg aaagaaaccg      2100
taaatatatt atcgcgatgg ttattatatt agcgggggac tacgtgtatt taaaagacta     2160
tattatgtaa gaaaaaggca cacgcaggtg ccttttttta gccatgttat gaaattatgt     2220
tttatttttg tgtgctgccg cttaagtgag cttgagcttg ttgcaccaag cgttttgtga     2280
tttctccgcc tactgaaccg ttgctgcgtg cagcagtgtc agaacctaga gttaccccaa     2340
attcttgagc gatttcatat ttatattgat ctaaaaattg ttctactcct ggtgttaata     2400
gtttatttgt tctagccatg attagtcatc tccttttta gtggtacagc agttcactgc      2460
tgtacctgta ttatttgttg tttcctattt tgcatactgg taatggtttg caagaaagta     2520
taaaaaagcc cagctttcaa agaagctggg cttttttata tattatttta caactgcata     2580
ttgctcaaga gactgagcaa atgacttttg aagagatttt acttgttcta cgtatgcatc     2640
agatacgtgt tggaattctt ggcgcgtttt cttttgctct tctactaatt gtgttactac     2700
ttgatgatat tgttcttgcg cttgctttac taaagaatag cttgatttgc tttggttaaa     2760
aaaagctct tgtaattat ttaatgcttc atgcgtgcgg tttgtccatt cttcataaga      2820
atcggcaaca gcgttccag ctgtttacg taagttttca actgtttttt gttgaaggtc       2880
ttccaattca gctttccatt gtttgtctgt tgcttgaagt tgttcaactg cttttgttac     2940
```

```
aaattcttgc tgttgctcaa gtgcttttaa cgtccattgc tcaatttgtt tgtttccgtc   3000
tgcaatgttt tgtaaccect tgtccattg ttcccacatt gcatcaatta ctgtatcata   3060
ctttactgtt gacataatca aattcctcct tgaataattt ggtctggcga acagttatcg   3120
taatgaacaa aacgttaaag aagaaattcg tagttgtgtg ataaacctaa cattccgcgc   3180
tcgctggttg accgtgaaat ttaacattat attaggaaac gcagatgtac tgcgtgaatc   3240
cctttaatcg ttttcttcct cttttgattc ttttgacttt ttagaagaag aagagctaaa   3300
agggaacaac atgtcggtat acatgtgaaa aaatgaatct aacatgtttt gatactgttc   3360
aagtgaatta gcccacatac ttaaatattg ttcgccggca tctgttaatg aataaatccg   3420
gcgtgcaggt ccttcagctg acgtatccca ttgcgatgta atcaagttgt cttttcaag    3480 ctgtctcagc gtgcggtaga catttccctg atcaactgat gtgaatccaa agctcattag   3540
ttgctgaatg agcttgtaac catgtagatt ccaccctctt aaacttaaaa gaagaaaagg   3600
aaccatcaag ttttttggtg caccgctaat cgattttcct aagttgtttg aattagaggt   3660
gttatctttt tcacttgatc ccaaggtaat caccccttcg aaaaagaga atttgttttc    3720 catatgtgta atttacacct agatgaaaaa attgtcaaca ctttaaaaca ggtctttcaa   3780
atacaggaaa aaagaacgat ttttggatt tcgacaaaaa gcgtcaaaaa aattcaaaaa    3840
taaacaaaga tttagaattg tttattttgg aaaacgtatt tataatagta catgtaggta   3900 attttttataa catttataat ttgttggtaa gtgaattgtg aaaagattta cattatccaa   3960
taaataaacg caaaattggt tgcgtttact tagagcttct aatatgtcgc ttgtcacatt   4020
aagtgtccat attgaaagcc atcacttttta acgtacacaa gaaggagat ggagttttgg    4080 aacagcaaaa agtatttgat ccgtttcaag catggaaaga cgtatatgac aaaaccgaat   4140
cttactgggg taaagttatt ggggacaata tgaatcgtga agaattttcc cagctcatgg   4200
gaaatgtgct aaatatgaac cttcaatatc aacaagcagt aaatgaagta acggggcgct   4260
atctgcacca agtaaatgta ccaacaaaag aagatgtagc aaacgttgcg tcattagtca   4320
tcaatgtgga agaaaaagta gaattattag aagagcaatt tgacgatcgt tttgatgaat   4380
tagaagcaca gcaagaaagt gcatctgctt tgaaaaaaga tgtcactaag ctgaaatctg   4440
atgtcaaatc gttagacaaa aaactcgata agttttatc tcttcttgaa gggcagcaaa    4500
aaacacaaga cgagttaaaa gaaacgattc aaaaacaaat taaaactcaa ggtgagcagc   4560
ttcaggctca gctgttagaa aaacaagaaa aattagctga aaagccaaag gcagaagcta   4620
aatctgaagc aaaaccatca aacgctcaaa aaactgagca gccggctcgc aagtaaggta   4680
tcggagattt tataacaaca ttaactgctg tatttacagt aaaaatcatc gctgaagaag   4740 caaggggggaa attttttcatg acaacattac aaggtaaagt agcaatcgta acaggcggat   4800
ctaaaggtat cggggcagca attacacgtg agcttgcttc taatggagta aaagtagcag   4860
taaactataa cagcagtaaa gaatctgcag aagcaattgt aaaagaaatt aaagacaacg   4920
gcggagaagc tattgcggtt caagctgacg tgtcttatgt agatcaagca aaacacctaa   4980
tcgaagaaac aaaagctgcg tttggtcaat tagacattc agtaaacaat gctggaatta   5040
cgcgcgaccg ttcattcaag aagttaggtg aagaagattg gaaaaagta attgatgtaa   5100 acttacatag cgtatacaac acaacatcag ctgcgctaac gcacctttta gaatctgaag   5160
gtggtcgtgt tatcaatatt tcatcaatta ttggtcaagc gggcggattt ggtcaaacaa   5220
actactcagc tgctaaagca ggtatgctag gattcactaa atcattagct cttgaactag   5280
ctaagacagg cgtaacggtt aatgcaattt gcccaggatt tattgaaacg gaaatggtga   5340
```

```
tggcaattcc tgaagatgtt cgtgcaaaaa ttgttgcgaa aattccaact cgtcgcttag    5400
gtcacgctga agaaattgca cgtggagttg tttacttagc aaaagacggc gcgtacatta    5460
caggacaaca gttaaacatt aacggcggct tatacatgta ataaatgctg gccctgactt    5520 ttgtcgggc tgtgcttgtt aactaactac taatggaatg aaagggtgtg tatattcgtg     5580
gcaattcctt acgtgcaaga gtgggaaaaa ttaatcaaat caatgccaag tgaatataaa    5640
agttctgcaa gacgttttaa gcgtgcatat gaaattatga caacagaagc ggaaccggaa    5700
gttggattaa caccaaaaga ggttatttgg aaaaagaaca aagcgaaatt atatcgctat    5760
acgccagtaa aagataacct gcataaaaca ccaatcttac tcgtatatgc attgatcaat    5820
aaaccgtata ttttggattt aacacctgga acagccttg ttgaatactt attaaaccgc     5880
ggttttgacg tgtatttgct tgactgggga actcctgggc ttgaagacag caatatgaag    5940
ctagatgatt atattgtaga ttatattcca aaagcggcga aaaggtgct gcgcacttct      6000 aaatctcctg atttgtctgt tcttggttac tgcatgggcg gaactatgac atctattttt    6060
gctgcattaa atgaagactt gccgattaaa aacttaattt ttatgacaag tccatttgat    6120
ttttcggata caggtttata cggagcattc ctagatgatc gctactttaa tttagataaa    6180
gcagtagata cattcggaaa catccctcca gagatgattg actttggaaa caagatgtta    6240
aagccaatca cgaatttcta cggcccgtat gtaacgttgg tggaccgttc ggaaaatcag    6300
cggtttgttg aaagctggaa gctaatgcaa agtgggttg ctgacggaat cccatttgct     6360
ggcgaagctt atcgtcagtg gattcgtgac ttctatcaac aaaacaaact aatcaatggt    6420
gaacttgaag ttcgcggacg caaagtagat ttaaaaaata ttaaagctaa tattttaaac    6480
attgctgcta gccgtgatca tattgcgatg ccgcatcaag tggcagcttt aatggacgct    6540
gtttcaagtg aagataaaga gtataaattg ttgcaaacag gtcacgtatc tgttgtattt    6600
ggtccaaaag cagtgaagga acatatcct tcaatcggcg attggctaga aaacgctct      6660 aaataaaata aagacgaggc tgagacaaaa gtattttagc cgaagtgaaa acgaaccac     6720 tgatatcagt ggttcgtttt tttgtataaa cagacaatag cgagtgatga ttctttatct    6780
ggactgatgg gatttatgat atctaatgac aagtgagatg acttctttta tactaatgta    6840
gtcaccttct taaacatggg attttttaca tggatatagc tattcatgta acaatgagta    6900
tgctttgaga agaaagaaga aaactattag tattataatg aaaaaggaat gtcagattat    6960
gccacaacca tggaaacgac gagtaaggca gatgtcttca gctcaaatta ttgttacatt    7020
ttacatagtg gctgttacgc ttgggtttct attacttagt attccagaag ctttaaggcc    7080
aggagcaaag ttagcattta ttgatcgctt atttattgcc gttagtgcgg taagtgtaac    7140
agggctgaca cctgtctcga ctccagatac atttagtaca acgggctatt ttttactcgt    7200
ttttattttt caaatcggtg gtattggtgt aatgacactc agtacattta tttgatgat     7260 tttaggtaaa aaaatcggtc tgaaggaacg tcagctcatt atgacggacc ataatcaatc    7320
ccgtttatca ggattagttg atttgatgag aaatatttta tttattattt ttgccattga    7380
actagttggc gccattattt tagggttaca ttttctccgt tattattcga gctggacaga    7440
tgcgtttttg catggtttct ttgcttctgt cagtgctaca acaaatgctg gcttcgatat    7500
tacaggatct tcatttattc cgtatgccca tgattatttc gtacaagtgg taaccgttat    7560
tttaattacg cttggagcga ttggattccc tgtattaatt gaaatcaagc actattttt    7620 aacatttaaa gataagcgta aatttcaatt ttcgctattt acgaagctaa cgactattat    7680
```

-continued

```
gtttttttctg ctgttaggag ggggaacaat ctttgattctt gtgctagagc attcaggatt      7740
tctagcagat aagtcttggg atgaatcgtt tttttatgcg ttttttccaat ccgctgccac       7800 aaggagcgga ggagtggcga ccatgaatat taatgagttt tcacttccta cgttaattat       7860
gatgagcgcg atgatgttta tcggtgcttc accgagttca gtaggggag gaattc             7916
```

<210> SEQ ID NO 2
<211> LENGTH: 510
<212> TYPE: DNA
<213> ORGANISM: Bacillus megaterium

<400> SEQUENCE: 2

```
atgtcaacag taaagtatga tacagtaatt gatgcaatgt gggaacaatg gacaaagggg        60
ttacaaaaca ttgcagacgg aaacaaacaa attgagcaat ggacgttaaa agcacttgag       120
caacagcaag aatttgtaac aaaagcagtt gaacaacttc aagcaacaga caaacaatgg       180
aaagctgaat tggaagacct tcaacaaaaa acagttgaaa acttacgtaa aacagctgga       240
aacgctgttg ccgattctta tgaagaatgg acaaaccgca cgcatgaagc attaaataaa       300
ttacaagagc ttttttttaa ccaaagcaaa tcaagctatt ctttagtaaa gcaagcgcaa       360
gaacaatatc atcaagtagt aacacaatta gtagaagagc aaaagaaaac gcgccaagaa       420
ttccaacacg tatctgatgc atacgtagaa caagtaaaat ctcttcaaaa gtcatttgct       480
cagtctcttg agcaatatgc agttgtaaaa                                         510
```

<210> SEQ ID NO 3
<211> LENGTH: 170
<212> TYPE: PRT
<213> ORGANISM: Bacillus megaterium

<400> SEQUENCE: 3

```
Met Ser Thr Val Lys Tyr Asp Thr Val Ile Asp Ala Met Trp Glu Gln
  1               5                  10                  15

Trp Thr Lys Gly Leu Gln Asn Ile Ala Asp Gly Asn Lys Gln Ile Glu
             20                  25                  30

Gln Trp Thr Leu Lys Ala Leu Glu Gln Gln Glu Phe Val Thr Lys
         35                  40                  45

Ala Val Glu Gln Leu Gln Ala Thr Asp Lys Gln Trp Lys Ala Glu Leu
     50                  55                  60

Glu Asp Leu Gln Gln Lys Thr Val Glu Asn Leu Arg Lys Thr Ala Gly
 65                  70                  75                  80

Asn Ala Val Ala Asp Ser Tyr Glu Glu Trp Thr Asn Arg Thr His Glu
                 85                  90                  95

Ala Leu Asn Lys Leu Gln Glu Leu Phe Phe Asn Gln Ser Lys Ser Ser
            100                 105                 110

Tyr Ser Leu Val Lys Gln Ala Gln Glu Gln Tyr His Gln Val Val Thr
        115                 120                 125

Gln Leu Val Glu Glu Gln Lys Lys Thr Arg Gln Glu Phe Gln His Val
    130                 135                 140

Ser Asp Ala Tyr Val Glu Val Lys Ser Leu Gln Lys Ser Phe Ala
145                 150                 155                 160

Gln Ser Leu Glu Gln Tyr Ala Val Val Lys
                165                 170
```

<210> SEQ ID NO 4
<211> LENGTH: 438
<212> TYPE: DNA

<213> ORGANISM: Bacillus megaterium

<400> SEQUENCE: 4

| | | |
|---|---|---|
| ttgggatcaa gtgaaaaaga taacacctct aattcaaaca acttagaaaa atcgattagc | 60 |
| ggtgcaccaa aaaacttgat ggttcctttt cttcttttaa gtttaagagg gtggaatcta | 120 |
| catggttaca agctcattca gcaactaatg agctttggat tcacatcagt tgatcaggga | 180 |
| aatgtctacc gcacgctgag acagcttgaa aaagacaact tgattacatc gcaatgggat | 240 |
| acgtcagctg aaggacctgc acgccggatt tattcattaa cagatgccgg cgaacaatat | 300 |
| ttaagtatgt gggctaattc acttgaacag tatcaaaaca tgttagattc atttttttcac | 360 |
| atgtataccg acatgttgtt ccctttttagc tcttcttctt ctaaaaagtc aaaagaatca | 420 |
| aaagaggaag aaaacgat | 438 |

<210> SEQ ID NO 5
<211> LENGTH: 146
<212> TYPE: PRT
<213> ORGANISM: Bacillus megaterium

<400> SEQUENCE: 5

Met Gly Ser Ser Glu Lys Asp Asn Thr Ser Asn Ser Asn Asn Leu Glu
1               5                   10                  15

Lys Ser Ile Ser Gly Ala Pro Lys Asn Leu Met Val Pro Phe Leu Leu
            20                  25                  30

Leu Ser Leu Arg Gly Trp Asn Leu His Gly Tyr Lys Leu Ile Gln Gln
        35                  40                  45

Leu Met Ser Phe Gly Phe Thr Ser Val Asp Gln Gly Asn Val Tyr Arg
    50                  55                  60

Thr Leu Arg Gln Leu Glu Lys Asp Asn Leu Ile Thr Ser Gln Trp Asp
65                  70                  75                  80

Thr Ser Ala Glu Gly Pro Ala Arg Arg Ile Tyr Ser Leu Thr Asp Ala
                85                  90                  95

Gly Glu Gln Tyr Leu Ser Met Trp Ala Asn Ser Leu Glu Gln Tyr Gln
            100                 105                 110

Asn Met Leu Asp Ser Phe Phe His Met Tyr Thr Asp Met Leu Phe Pro
        115                 120                 125

Phe Ser Ser Ser Ser Lys Lys Ser Lys Glu Ser Lys Glu Glu
    130                 135                 140

Asn Asp
145

<210> SEQ ID NO 6
<211> LENGTH: 504
<212> TYPE: DNA
<213> ORGANISM: Bacillus megaterium

<400> SEQUENCE: 6

| | | |
|---|---|---|
| atgaatcgtg aagaattttc ccagctcatg ggaaatgtgc taaatatgaa ccttcaatat | 60 |
| caacaagcag taaatgaagt aacggggcgc tatctgcacc aagtaaatgt accaacaaaa | 120 |
| gaagatgtag caaacgttgc gtcattagtc atcaatgtgg aagaaaaagt agaattatta | 180 |
| gaagagcaat tgacgatcg ttttgatgaa ttagaagcac agcaagaaag tgcatctgct | 240 |
| ttgaaaaaag atgtcactaa gctgaaatct gatgtcaaat cgttagacaa aaaactcgat | 300 |
| aaagttttat ctcttcttga agggcagcaa aaaacacaag acgagttaaa agaaacgatt | 360 |
| caaaaacaaa ttaaaactca aggtgagcag cttcaggctc agctgttaga aaaacaagaa | 420 |

```
aaattagctg aaaagccaaa ggcagaagct aaatctgaag caaaaccatc aaacgctcaa      480
aaaactgagc agccggctcg caag                                             504
```

<210> SEQ ID NO 7
<211> LENGTH: 168
<212> TYPE: PRT
<213> ORGANISM: Bacillus megaterium

<400> SEQUENCE: 7

```
Met Asn Arg Glu Glu Phe Ser Gln Leu Met Gly Asn Val Leu Asn Met
 1               5                  10                  15

Asn Leu Gln Tyr Gln Gln Ala Val Asn Glu Val Thr Gly Arg Tyr Leu
            20                  25                  30

His Gln Val Asn Val Pro Thr Lys Glu Asp Val Ala Asn Val Ala Ser
        35                  40                  45

Leu Val Ile Asn Val Glu Glu Lys Val Glu Leu Leu Glu Glu Gln Phe
    50                  55                  60

Asp Asp Arg Phe Asp Glu Leu Glu Ala Gln Gln Glu Ser Ala Ser Ala
65                  70                  75                  80

Leu Lys Lys Asp Val Thr Lys Leu Lys Ser Asp Val Lys Ser Leu Asp
                85                  90                  95

Lys Lys Leu Asp Lys Val Leu Ser Leu Leu Glu Gly Gln Lys Thr
            100                 105                 110

Gln Asp Glu Leu Lys Glu Thr Ile Gln Lys Gln Ile Lys Thr Gln Gly
        115                 120                 125

Glu Gln Leu Gln Ala Gln Leu Leu Glu Lys Gln Glu Lys Leu Ala Glu
    130                 135                 140

Lys Pro Lys Ala Glu Ala Lys Ser Glu Ala Lys Pro Ser Asn Ala Gln
145                 150                 155                 160

Lys Thr Glu Gln Pro Ala Arg Lys
                165
```

<210> SEQ ID NO 8
<211> LENGTH: 741
<212> TYPE: DNA
<213> ORGANISM: Bacillus megaterium

<400> SEQUENCE: 8

```
atgacaacat tacaaggtaa agtagcaatc gtaacaggcg gatctaaagg tatcggggca      60
gcaattacac gtgagcttgc ttctaatgga gtaaaagtag cagtaaacta taacagcagt     120
aaagaatctg cagaagcaat tgtaaaagaa attaaagaca acggcggaga agctattgcg     180
gttcaagctg acgtgtctta tgtagatcaa gcaaacacc taatcgaaga aacaaaagct     240
gcgtttggtc aattagacat tctagtaaac aatgctggaa ttacgcgcga ccgttcattc     300
aagaagttag gtgaagaaga ttggaaaaaa gtaattgatg taaacttaca tagcgtatac     360
aacacaacat cagctgcgct aacgcacctt ttagaatctg aaggtggtcg tgttatcaat     420
atttcatcaa ttattggtca agcgggcgga tttggtcaaa caaactactc agctgctaaa     480
gcaggtatgc taggattcac taaatcatta gctcttgaac tagctaagac aggcgtaacg     540
gttaatgcaa tttgcccagg atttattgaa acggaaatgg tgatggcaat tcctgaagat     600
gttcgtgcaa aaattgttgc gaaaattcca actcgtcgct taggtcacgc tgaagaaatt     660
gcacgtggag ttgtttactt agcaaaagac ggcgcgtaca ttcaggaca acagttaaac     720 attaacggcg gcttatacat g                                               741
```

```
<210> SEQ ID NO 9
<211> LENGTH: 247
<212> TYPE: PRT
<213> ORGANISM: Bacillus megaterium

<400> SEQUENCE: 9

Met Thr Thr Leu Gln Gly Lys Val Ala Ile Val Thr Gly Gly Ser Lys
  1               5                  10                  15

Gly Ile Gly Ala Ala Ile Thr Arg Glu Leu Ala Ser Asn Gly Val Lys
             20                  25                  30

Val Ala Val Asn Tyr Asn Ser Ser Lys Glu Ser Ala Glu Ala Ile Val
         35                  40                  45

Lys Glu Ile Lys Asp Asn Gly Gly Glu Ala Ile Ala Val Gln Ala Asp
     50                  55                  60

Val Ser Tyr Val Asp Gln Ala Lys His Leu Ile Glu Glu Thr Lys Ala
 65                  70                  75                  80

Ala Phe Gly Gln Leu Asp Ile Leu Val Asn Asn Ala Gly Ile Thr Arg
                 85                  90                  95

Asp Arg Ser Phe Lys Lys Leu Gly Glu Glu Asp Trp Lys Lys Val Ile
            100                 105                 110

Asp Val Asn Leu His Ser Val Tyr Asn Thr Thr Ser Ala Ala Leu Thr
        115                 120                 125

His Leu Leu Glu Ser Glu Gly Gly Arg Val Ile Asn Ile Ser Ser Ile
    130                 135                 140

Ile Gly Gln Ala Gly Gly Phe Gly Gln Thr Asn Tyr Ser Ala Ala Lys
145                 150                 155                 160

Ala Gly Met Leu Gly Phe Thr Lys Ser Leu Ala Leu Glu Leu Ala Lys
                165                 170                 175

Thr Gly Val Thr Val Asn Ala Ile Cys Pro Gly Phe Ile Glu Thr Glu
            180                 185                 190

Met Val Met Ala Ile Pro Glu Asp Val Arg Ala Lys Ile Val Ala Lys
        195                 200                 205

Ile Pro Thr Arg Arg Leu Gly His Ala Glu Glu Ile Ala Arg Gly Val
    210                 215                 220

Val Tyr Leu Ala Lys Asp Gly Ala Tyr Ile Thr Gly Gln Gln Leu Asn
225                 230                 235                 240

Ile Asn Gly Gly Leu Tyr Met
                245

<210> SEQ ID NO 10
<211> LENGTH: 1086
<212> TYPE: DNA
<213> ORGANISM: Bacillus megaterium

<400> SEQUENCE: 10
gtggcaattc cttacgtgca agagtgggaa aaattaatca aatcaatgcc aagtgaatat      60
aaaagttctg caagacgttt taagcgtgca tatgaaatta tgacaacaga agcggaaccg     120
gaagttggat taacaccaaa agaggttatt tggaaaaaga acaaagcgaa attatatcgc     180
tatacgccag taaagataaa cctgcataaa acaccaatct tactcgtata tgcattgatc     240
aataaaccgt atattttgga tttaacacct ggaaacagcc ttgttgaata cttattaaac     300
cgcggttttg acgtgtattt gcttgactgg ggaactcctg gcttgaagag cagcaatatg     360
aagctagatg attatattgt agattatatt ccaaaagcgg cgaaaaaggt gctgcgcact     420
```

```
tctaaatctc ctgatttgtc tgttcttggt tactgcatgg gcggaactat gacatctatt    480
tttgctgcat taaatgaaga cttgccgatt aaaaacttaa ttttatgac aagtccattt     540 gatttttcgg atacaggttt atacggagca ttcctagatg atcgctactt taatttagat    600
aaagcagtag atacattcgg aaacatccct ccagagatga ttgactttgg aaacaagatg    660
ttaaagccaa tcacgaattt ctacggcccg tatgtaacgt tggtggaccg ttcggaaaat    720
cagcggtttg ttgaaagctg gaagctaatg caaaagtggg ttgctgacgg aatcccattt    780
gctggcgaag cttatcgtca gtggattcgt gacttctatc aacaaaacaa actaatcaat    840
ggtgaacttg aagttcgcgg acgcaaagta gatttaaaaa atattaaagc taatatttta    900
aacattgctg ctagccgtga tcatattgcg atgccgcatc aagtggcagc tttaatggac    960
gctgtttcaa gtgaagataa agagtataaa ttgttgcaaa caggtcacgt atctgttgta    1020
tttggtccaa aagcagtgaa ggaaacatat ccttcaatcg gcgattggct agaaaaacgc    1080
tctaaa                                                               1086

<210> SEQ ID NO 11
<211> LENGTH: 362
<212> TYPE: PRT
<213> ORGANISM: Bacillus megaterium

<400> SEQUENCE: 11

Met Ala Ile Pro Tyr Val Gln Glu Trp Glu Lys Leu Ile Lys Ser Met
 1               5                  10                  15

Pro Ser Glu Tyr Lys Ser Ser Ala Arg Arg Phe Lys Arg Ala Tyr Glu
                20                  25                  30

Ile Met Thr Thr Glu Ala Glu Pro Glu Val Gly Leu Thr Pro Lys Glu
            35                  40                  45

Val Ile Trp Lys Lys Asn Lys Ala Lys Leu Tyr Arg Tyr Thr Pro Val
        50                  55                  60

Lys Asp Asn Leu His Lys Thr Pro Ile Leu Leu Val Tyr Ala Leu Ile
 65                  70                  75                  80

Asn Lys Pro Tyr Ile Leu Asp Leu Thr Pro Gly Asn Ser Leu Val Glu
                85                  90                  95

Tyr Leu Leu Asn Arg Gly Phe Asp Val Tyr Leu Leu Asp Trp Gly Thr
           100                 105                 110

Pro Gly Leu Glu Asp Ser Asn Met Lys Leu Asp Asp Tyr Ile Val Asp
       115                 120                 125

Tyr Ile Pro Lys Ala Ala Lys Lys Val Leu Arg Thr Ser Lys Ser Pro
   130                 135                 140

Asp Leu Ser Val Leu Gly Tyr Cys Met Gly Gly Thr Met Thr Ser Ile
145                 150                 155                 160

Phe Ala Ala Leu Asn Glu Asp Leu Pro Ile Lys Asn Leu Ile Phe Met
                165                 170                 175

Thr Ser Pro Phe Asp Phe Ser Asp Thr Gly Leu Tyr Gly Ala Phe Leu
            180                 185                 190

Asp Asp Arg Tyr Phe Asn Leu Asp Lys Ala Val Asp Thr Phe Gly Asn
        195                 200                 205

Ile Pro Pro Glu Met Ile Asp Phe Gly Asn Lys Met Leu Lys Pro Ile
    210                 215                 220

Thr Asn Phe Tyr Gly Pro Tyr Val Thr Leu Val Asp Arg Ser Glu Asn
225                 230                 235                 240

Gln Arg Phe Val Glu Ser Trp Lys Leu Met Gln Lys Trp Val Ala Asp
                245                 250                 255
```

```
Gly Ile Pro Phe Ala Gly Glu Ala Tyr Arg Gln Trp Ile Arg Asp Phe
            260                 265                 270

Tyr Gln Gln Asn Lys Leu Ile Asn Gly Glu Leu Glu Val Arg Gly Arg
        275                 280                 285

Lys Val Asp Leu Lys Asn Ile Lys Ala Asn Ile Leu Asn Ile Ala Ala
290                 295                 300

Ser Arg Asp His Ile Ala Met Pro His Gln Val Ala Ala Leu Met Asp
305                 310                 315                 320

Ala Val Ser Ser Glu Asp Lys Glu Tyr Lys Leu Leu Gln Thr Gly His
                325                 330                 335

Val Ser Val Val Phe Gly Pro Lys Ala Val Lys Glu Thr Tyr Pro Ser
            340                 345                 350

Ile Gly Asp Trp Leu Glu Lys Arg Ser Lys
            355                 360

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence:Synthetic

<400> SEQUENCE: 12
aayacrgtna ataynnnac rgtnatynnn gcdatgatg                          39

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:Synthetic

<400> SEQUENCE: 13
gcdatyccdt aygtncarga agghttyaaa                                   30

<210> SEQ ID NO 14
<211> LENGTH: 19
<212> TYPE: DNA
<213> ORGANISM: SYNTHETIC

<400> SEQUENCE: 14
gcttcatgcg tgcggtttg                                               19

<210> SEQ ID NO 15
<211> LENGTH: 22
<212> TYPE: DNA
<213> ORGANISM: SYNTHETIC

<400> SEQUENCE: 15
ggaccgttcg gaaaatcagc gg                                           22

<210> SEQ ID NO 16
<211> LENGTH: 20
<212> TYPE: DNA
<213> ORGANISM: SYNTHETIC

<400> SEQUENCE: 16 ccoctttgtc cattgttccc                                              20

<210> SEQ ID NO 17
<211> LENGTH: 19
```

-continued

<210> SEQ ID NO 17
<211> LENGTH: 19
<212> TYPE: DNA
<213> ORGANISM: SYNTHETIC

<400> SEQUENCE: 17
ccatgtagat tccaccctc                                              19

<210> SEQ ID NO 18
<211> LENGTH: 19
<212> TYPE: DNA
<213> ORGANISM: SYNTHETIC

<400> SEQUENCE: 18
ctccatctcc tttcttgtg                                              19

<210> SEQ ID NO 19
<211> LENGTH: 17
<212> TYPE: PRT
<213> ORGANISM: Bacillus megaterium

<400> SEQUENCE: 19

Lys Val Phe Gly Arg Xaa Glu Leu Ala Ala Ala Met Lys Arg Xaa Gly
 1               5                  10                  15

Leu

<210> SEQ ID NO 20
<211> LENGTH: 15
<212> TYPE: PRT
<213> ORGANISM: Bacillus megaterium

<400> SEQUENCE: 20

Asn Thr Val Lys Tyr Xaa Thr Val Ile Xaa Ala Met Xaa Xaa Gln
 1               5                  10                  15

<210> SEQ ID NO 21
<211> LENGTH: 11
<212> TYPE: PRT
<213> ORGANISM: Bacillus megaterium

<400> SEQUENCE: 21

Ala Ile Pro Tyr Val Gln Glu Xaa Glu Lys Leu
 1               5                  10

<210> SEQ ID NO 22
<211> LENGTH: 813
<212> TYPE: DNA
<213> ORGANISM: Bacillus megaterium

<400> SEQUENCE: 22
atggatgcat cactttttgtt agagtatgga tgggtattgc agtgctggt tgcattagaa      60 ggaattttgg cggcggataa tgctcttgtg atggctatta tggtcaaaca tttaccggaa    120
gaaaaacgca agaaggcatt attttacgga ttagccggtg cctttatttt tagatttggt    180
tcgttgttct tgatttcatt tttagtcgac gtatggcagc ttcaagctat aggagccatt    240
tacttattgt tcatttccat taatcatatt gtgaagcgat atgtgaaaaa agacgatcat    300
gaaaaagtga agaagcaga cgagaaaaag ggctcaggtt tctggatgac ggttttaaaa    360
gtagaaatag cagacattgc ttttgccgtt gattcaattt tggccgctgt ggctctcgcc    420
gttacgttgc caacaacaaa tcttcctcaa attggcggac tcgacggcgg acaattcttg    480
gtgatcttcg ccggaggaat tatgggatta attattatgc gttttgctgc aacttggttc    540
gtcaagctat aaatacgcg cccaggccta gaaacggcgg cttttgctat tgtaggctgg    600

-continued

```
gtaggagtta agttagcggt ctataccctt gctcatccag agttaggtat tattaatgaa      660
catttccctg aatcaaaagt gtggaaaatt acgttttgga ttgtgttact tggcatagct      720
gcttcaggct ggtttctatc taaaaataaa gaacaaactg atcttgaagg ctcagagaaa      780
gaaaaagaat cgttaaaaaa aattgaaaat caa                                   813
```

<210> SEQ ID NO 23
<211> LENGTH: 271
<212> TYPE: PRT
<213> ORGANISM: Bacillus megaterium

<400> SEQUENCE: 23

```
Met Asp Ala Ser Leu Leu Glu Tyr Gly Trp Val Leu Leu Val Leu
 1               5                   10                  15

Val Ala Leu Glu Gly Ile Leu Ala Ala Asp Asn Ala Leu Val Met Ala
                20                  25                  30

Ile Met Val Lys His Leu Pro Glu Glu Lys Arg Lys Lys Ala Leu Phe
            35                  40                  45

Tyr Gly Leu Ala Gly Ala Phe Ile Phe Arg Phe Gly Ser Leu Phe Leu
        50                  55                  60

Ile Ser Phe Leu Val Asp Val Trp Gln Leu Gln Ala Ile Gly Ala Ile
 65                 70                  75                  80

Tyr Leu Leu Phe Ile Ser Ile Asn His Ile Val Lys Arg Tyr Val Lys
                85                  90                  95

Lys Asp Asp His Glu Lys Val Lys Glu Ala Asp Glu Lys Lys Gly Ser
            100                 105                 110

Gly Phe Trp Met Thr Val Leu Lys Val Glu Ile Ala Asp Ile Ala Phe
        115                 120                 125

Ala Val Asp Ser Ile Leu Ala Ala Val Ala Leu Ala Val Thr Leu Pro
    130                 135                 140

Thr Thr Asn Leu Pro Gln Ile Gly Gly Leu Asp Gly Gly Gln Phe Leu
145                 150                 155                 160

Val Ile Phe Ala Gly Gly Ile Met Gly Leu Ile Ile Met Arg Phe Ala
                165                 170                 175

Ala Thr Trp Phe Val Lys Leu Leu Asn Thr Arg Pro Gly Leu Glu Thr
            180                 185                 190

Ala Ala Phe Ala Ile Val Gly Trp Val Gly Val Lys Leu Ala Val Tyr
        195                 200                 205

Thr Leu Ala His Pro Glu Leu Gly Ile Ile Asn Glu His Phe Pro Glu
    210                 215                 220

Ser Lys Val Trp Lys Ile Thr Phe Trp Ile Val Leu Leu Gly Ile Ala
225                 230                 235                 240

Ala Ser Gly Trp Phe Leu Ser Lys Asn Lys Glu Gln Thr Asp Leu Glu
                245                 250                 255

Gly Ser Glu Lys Glu Lys Glu Ser Leu Lys Lys Ile Glu Asn Gln
            260                 265                 270
```

<210> SEQ ID NO 24
<211> LENGTH: 708
<212> TYPE: DNA
<213> ORGANISM: Bacillus megaterium

<400> SEQUENCE: 24

```
atgctcacaa aagttcaaac gcctccatcg cttgaaacgc ttgtactgac gattcagcaa       60
ggggataaac aattacataa tgaaatgatt caacaatata aaccgtttat tgctaaagtt      120
```

-continued

```
gtttcagctg tatgtaaacg ttatataagt gaagctgacg atgaatttag cattggtctg    180
attgcattta atgaagccat tgaaaattac acaatccaaa aaggacgatc tcttcttgca    240
tttgcggaac ttattattaa agaagagta atcgactata ttcgaaaaga aaagcgaaat     300
caaacgctgc tctataaccg aattgaaaat gaaggtttta ttcaaggtaa ggtagaaagg    360
gatatatcgc tttctaacta taaaaggcaa agtgaaactt catatattca agaggaaatg    420 acttatttt gtcaggcgct aaaattgttt aaattaactc ttgaagacat tattaacacg     480
tctcctaaac ataaggatgc aagggggaaat gcagtggaag ttgcatcttt tatcgtcaat   540
gaaaaagaat taaagataa gctgttttta agcggcagc ttcctattcg cttgattgaa      600
aaacatgtca agtaagccg gaaaacaatt gaaagaaacc gtaaatatat tatcgcgatg    660
gttattatat tagcggggga ctacgtgtat ttaaaagact atattatg                 708
```

<210> SEQ ID NO 25
<211> LENGTH: 236
<212> TYPE: PRT
<213> ORGANISM: Bacillus megaterium

<400> SEQUENCE: 25

```
Met Leu Thr Lys Val Gln Thr Pro Pro Ser Leu Glu Thr Leu Val Leu
  1               5                  10                  15

Thr Ile Gln Gln Gly Asp Lys Gln Leu His Asn Glu Met Ile Gln Gln
             20                  25                  30

Tyr Lys Pro Phe Ile Ala Lys Val Val Ser Ala Val Cys Lys Arg Tyr
         35                  40                  45

Ile Ser Glu Ala Asp Asp Glu Phe Ser Ile Gly Leu Ile Ala Phe Asn
     50                  55                  60

Glu Ala Ile Glu Asn Tyr Thr Ile Gln Lys Gly Arg Ser Leu Leu Ala
 65                  70                  75                  80

Phe Ala Glu Leu Ile Ile Lys Arg Arg Val Ile Asp Tyr Ile Arg Lys
                 85                  90                  95

Glu Lys Arg Asn Gln Thr Leu Leu Tyr Asn Arg Ile Glu Asn Glu Gly
            100                 105                 110

Phe Ile Gln Gly Lys Val Glu Arg Asp Ile Ser Leu Ser Asn Tyr Lys
        115                 120                 125

Arg Gln Ser Glu Thr Ser Tyr Ile Gln Glu Glu Met Thr Tyr Phe Cys
    130                 135                 140

Gln Ala Leu Lys Leu Phe Lys Leu Thr Leu Glu Asp Ile Ile Asn Thr
145                 150                 155                 160

Ser Pro Lys His Lys Asp Ala Arg Gly Asn Ala Val Glu Val Ala Ser
                165                 170                 175

Phe Ile Val Asn Glu Lys Glu Leu Lys Asp Lys Leu Phe Leu Lys Arg
            180                 185                 190

Gln Leu Pro Ile Arg Leu Ile Glu Lys His Val Lys Val Ser Arg Lys
        195                 200                 205

Thr Ile Glu Arg Asn Arg Lys Tyr Ile Ile Ala Met Val Ile Ile Leu
    210                 215                 220

Ala Gly Asp Tyr Val Tyr Leu Lys Asp Tyr Ile Met
225                 230                 235
```

<210> SEQ ID NO 26
<211> LENGTH: 957
<212> TYPE: DNA
<213> ORGANISM: Bacillus megaterium -continued

<400> SEQUENCE: 26

```
atgccacaac catggaaacg acgagtaagg cagatgtctt cagctcaaat tattgttaca    60
ttttacatag tggctgttac gcttgggttt ctattactta gtattccaga agctttaagg   120
ccaggagcaa agttagcatt tattgatcgc ttatttattg ccgttagtgc ggtaagtgta   180
acagggctga cacctgtctc gactccagat acatttagta caacgggcta ttttttactc   240
gttttatatt ttcaaatcgg tggtattggt gtaatgacac tcagtacatt tatttggatg   300
atttaggta aaaaaatcgg tctgaaggaa cgtcagctca ttatgacgga ccataatcaa   360
tcccgtttat caggattagt tgatttgatg agaaatattt tatttattat ttttgccatt   420
gaactagttg gcgccattat tttagggtta catttctcc gttattattc gagctggaca    480
gatgcgtttt tgcatggttt ctttgcttct gtcagtgcta caacaaatgc tggcttcgat   540
attacaggat cttcatttat tccgtatgcc catgattatt tcgtacaagt ggtaaccgtt   600
attttaatta cgcttggagc gattggattc cctgtattaa ttgaaatcaa gcactatttt   660
ttaacattta agataagcg taaatttcaa ttttcgctat ttacgaagct aacgactatt    720
atgttttttc tgctgttagg aggggaaca atcttgattc ttgtgctaga gcattcagga   780
tttctagcag ataagtcttg ggatgaatcg ttttttttatg cgttttttcca atccgctgcc   840
acaaggagcg gaggagtggc gaccatgaat attaatgagt tttcacttcc tacgttaatt   900
atgatgagcg cgatgatgtt tatcggtgct tcaccgagtt cagtagggggg aggaatt    957
```

<210> SEQ ID NO 27
<211> LENGTH: 319
<212> TYPE: PRT
<213> ORGANISM: Bacillus megaterium

<400> SEQUENCE: 27

```
Met Pro Gln Pro Trp Lys Arg Arg Val Arg Gln Met Ser Ser Ala Gln
  1               5                  10                  15

Ile Ile Val Thr Phe Tyr Ile Val Ala Val Thr Leu Gly Phe Leu Leu
             20                  25                  30

Leu Ser Ile Pro Glu Ala Leu Arg Pro Gly Ala Lys Leu Ala Phe Ile
         35                  40                  45

Asp Arg Leu Phe Ile Ala Val Ser Ala Val Ser Val Thr Gly Leu Thr
     50                  55                  60

Pro Val Ser Thr Pro Asp Thr Phe Ser Thr Thr Gly Tyr Phe Leu Leu
 65                  70                  75                  80

Val Phe Ile Phe Gln Ile Gly Gly Ile Gly Val Met Thr Leu Ser Thr
             85                  90                  95

Phe Ile Trp Met Ile Leu Gly Lys Lys Ile Gly Leu Lys Glu Arg Gln
            100                 105                 110

Leu Ile Met Thr Asp His Asn Gln Ser Arg Leu Ser Gly Leu Val Asp
        115                 120                 125

Leu Met Arg Asn Ile Leu Phe Ile Ile Phe Ala Ile Glu Leu Val Gly
    130                 135                 140

Ala Ile Ile Leu Gly Leu His Phe Leu Arg Tyr Tyr Ser Ser Trp Thr
145                 150                 155                 160

Asp Ala Phe Leu His Gly Phe Phe Ala Ser Val Ser Ala Thr Thr Asn
                165                 170                 175

Ala Gly Phe Asp Ile Thr Gly Ser Ser Phe Ile Pro Tyr Ala His Asp
            180                 185                 190
```

```
Tyr Phe Val Gln Val Val Thr Val Ile Leu Ile Thr Leu Gly Ala Ile
            195                 200                 205

Gly Phe Pro Val Leu Ile Glu Ile Lys His Tyr Phe Leu Thr Phe Lys
            210                 215                 220

Asp Lys Arg Lys Phe Gln Phe Ser Leu Phe Thr Lys Leu Thr Thr Ile
225                 230                 235                 240

Met Phe Phe Leu Leu Leu Gly Gly Thr Ile Leu Ile Leu Val Leu
            245                 250                 255

Glu His Ser Gly Phe Leu Ala Asp Lys Ser Trp Asp Glu Ser Phe Phe
            260                 265                 270

Tyr Ala Phe Phe Gln Ser Ala Ala Thr Arg Ser Gly Gly Val Ala Thr
            275                 280                 285

Met Asn Ile Asn Glu Phe Ser Leu Pro Thr Leu Ile Met Met Ser Ala
            290                 295                 300

Met Met Phe Ile Gly Ala Ser Pro Ser Ser Val Gly Gly Gly Ile
305                 310                 315

<210> SEQ ID NO 28
<211> LENGTH: 195
<212> TYPE: DNA
<213> ORGANISM: Bacillus megaterium

<400> SEQUENCE: 28
atggctagaa caaataaact attaacacca ggagtagaac aatttttaga tcaatataaa      60
tatgaaatcg ctcaagaatt tggggtaact ctaggttctg acactgctgc acgcagcaac     120
ggttcagtag gcggagaaat cacaaaacgc ttggtgcaac aagctcaagc tcacttaagc     180
ggcagcacac aaaaa                                                      195

<210> SEQ ID NO 29
<211> LENGTH: 65
<212> TYPE: PRT
<213> ORGANISM: Bacillus megaterium

<400> SEQUENCE: 29

Met Ala Arg Thr Asn Lys Leu Leu Thr Pro Gly Val Glu Gln Phe Leu
  1               5                  10                  15

Asp Gln Tyr Lys Tyr Glu Ile Ala Gln Glu Phe Gly Val Thr Leu Gly
             20                  25                  30

Ser Asp Thr Ala Ala Arg Ser Asn Gly Ser Val Gly Gly Glu Ile Thr
         35                  40                  45

Lys Arg Leu Val Gln Gln Ala Gln Ala His Leu Ser Gly Ser Thr Gln
     50                  55                  60

Lys
 65
```